US008778683B2

(12) United States Patent
Nano

(10) Patent No.: US 8,778,683 B2
(45) **Date of Patent: *Jul. 15, 2014**

(54) VACCINES COMPRISING HEAT-SENSITIVE TRANSGENES

(75) Inventor: Francis E. Nano, Victoria (CA)

(73) Assignee: UVic Industry Partnerships Inc., Victoria, BC (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/496,723

(22) PCT Filed: Oct. 7, 2010

(86) PCT No.: PCT/CA2010/001561
§ 371 (c)(1),
(2), (4) Date: Apr. 12, 2012

(87) PCT Pub. No.: WO2011/041886
PCT Pub. Date: Apr. 14, 2011

(65) Prior Publication Data

US 2012/0189661 A1 Jul. 26, 2012

Related U.S. Application Data

(60) Provisional application No. 61/249,385, filed on Oct. 7, 2009, provisional application No. 61/322,634, filed on Apr. 9, 2010.

(51) Int. Cl.
*C12N 15/74* (2006.01)
*C12N 1/20* (2006.01)
*C07H 21/02* (2006.01)
*C07K 1/00* (2006.01)

(52) U.S. Cl.
USPC ........ 435/471; 435/476; 435/488; 435/320.1; 435/252.3; 435/252.33; 536/23.1; 530/350; 424/93.2

(58) Field of Classification Search
None
See application file for complete search history.

(56) References Cited

FOREIGN PATENT DOCUMENTS

EP 1 245 679 A1 10/2002
WO WO 2005/035750 A2 4/2005

OTHER PUBLICATIONS

Duplantis et al., “Essential Genes from Arctic Bacteria Used to Construct Stable, Temperature-Sensitive Bacterial Vaccines,” *Proc. Natl. Acad. Sci. USA 107*:13456-13460, 2010.
Ferrer et al., “Functional Consequences of Single:Double Ring Transitions in Chaperonins: Life in the Cold,” *Mol. Microbiol.* 53:167-182, 2004.
GenBank Database Accession No. AAZ27221, Mar. 11, 2010. DNA ligase, NAD-dependent [Colwellia psychrerythraea 34H].
GenBank Database Accession No. CR954246, Jul. 26, 2005. *Pseudoalteromonas haloplanktis* str. TAC125 chromosome I, complete sequence.
GenBank Database Accession No. CAI86158, Jul. 22, 2008. NAD-dependent DNA ligase [*Pseudoalteromonas haloplanktis* TAC125].
GenBank Accession No. CP000447, Nov. 29, 2007. *Shewanella frigidimarina* NCIMB 400, complete genome.
Georlette et al., “A DNA Ligase from the Psychrophile *Pseudoalteromonas haloplanktis* Gives Insights into the Adaption of Proteins to Low Temperatures,” *Eur. J. Biochem.* 267:3502-3512, 2000.
Médigue et al., “Coping with Cold: The Genome of the Versatile Marine Antarctica Bacterium *Pseudoalteromonas haloplanktis* TAC125,” *Genome Res.* 15:1325-1335, 2005.
Methe et al., “The Psychrophilic Lifestyle as Revealed by the Genome Sequence of *Colwellia psychrerythraea* 34H Through Genomic and Proteomic Analysis,” *Proc. Natl. Acad. Sci. USA* 102:10913-10918, 2005.
Database Accession No. AF126866, Aug. 17, 1999.
Database Accession No. Q47YI0, Sep. 13, 2005.
Ellis, R.W., “New Technologies for Making Vaccines,” *Vaccine 17*:1596-1604, 1999.
Ferrer et al., “Chaperonins Govern Growth of *Escherichia coli* at Low Temperatures,” *Nature Biotechnol.* 21:1266-1267, 2003.
Margesin and Schinner, “Properties of Cold-Adapted Microorganisms and Their Potential Role in Biotechnology,” *J. Biotech.* 33:1-14, 1994.
Munier-Lehmann et al., “Relationship Between Bacterial Virulence and Nucleotide Metabolism: A Mutation in the Adenylate Kinase Gene Renders *Yersinia pestis* Avirulent,” *Biochem. J.* 373:515-522, 2003.
Olsen and Metcalf, “Conversion of Mesophilic to Psychrophilic Bacteria,” *Science 162*:1288-1289, 1968.

*Primary Examiner* — Oluwatosin Ogunbiyi
(74) *Attorney, Agent, or Firm* — Klarquist Sparkman, LLP

(57) ABSTRACT

The present disclosure provides temperature sensitive essential nucleic acid molecules from a psychrophilic bacterium, proteins encoded by the nucleic acid molecules, as well as recombinant cells into which have been introduced such nucleic acid molecules. The disclosed recombinant cells containing one or more essential nucleic acid molecules from a psychrophilic bacterium are thereby made temperature sensitive, and can be administered to a mammal to induce an immune response in the mammal.

13 Claims, 21 Drawing Sheets

*Francisella novicida* with
*Pseudoalteromonas haloplanktis ligA-2*

FIG. 11A

SEQ ID NO: 1

ATGACTCCAGTCGAAAAGAAAATTAGCCAACTGCAACAGCAGCTTAATCAATATAATCATGAATATTA
TGTATTAGACCAACCTAGTGTGCCTGATGCAGAATATGACCGATTAATGACAGCATTAATCGATTTAG
AAAAGACTAATCCTGAGCTTAAGACTATTGACTCACCTAGCCAAAAAGTTGGCGGTCAGGCATTAAAA
TCTTTCACTCAAGTAACTCATCAGCTGCCGATGCTTTCTCTTGATAATGTTTTTCTTTAGATGATTT
TCACGCATTTGTTAAACGCGTAAAAGATAGGTTAAATGACAATCAAGCGATAGTCTTTGTGCCGAGC
CTAAATTAGACGGTTTAGCAGTGAGTTTACGTTATGAGCACGGGCAGTTAATACAAGCGGCTACACGT
GGCGATGGTAGTGTAGGGGAGAATATTACGACTAACATTCGTACAATAAAATCTATTCCGCTTAAGTT
AATGGGCACACCAGGTAAAGATTTTCCTGATATCGTTGAAGTCCGCGGTGAAGTTTTATGCCTAAGG
CAAGTTTTGACGCATTAAATACATGGCTAAAAAACGTGGCGAGAAAGGTTTTGCAAATCCACGTAAT
GCAGCGGCGGGAAGTTTACGACAACTTGATTCTAAAATCACCGCTAAACGTAATTTAGCTTTTTACGC
TTATAGCCTTGGATTTGTAGGGAAACTGTCTGATGGAGGCGCTGAAAGTACCGATTTAACCAATGACT
TTTTTGCTAACTCTCATCATGAAAGACTATGTCAGCTTAAAAGGTTGGGTTTGCCTATGTGTCCAGAA
GTACGCTTACTTGAAAGTGAGCAAGCCTGTGATGCGTTTTATCAAGATATCTTAGCAAAGCGTAGTGC
CTTGAGTTATGAAATTGATGGCACTGTATTAAAAGTTGATGAAATCTCTTTGCAGAAACGTTTAGGGT
TTGTCGCACGTGCCCCACGTTGGGCTATTGCTTATAAATTCCCTGCGGAAGAAGAATTAACCTGTGTT
GAAGATGTCGAGTTTCAAGTAGGGCGTACCGGCGCGATTACTCCCGTAGCACGTTTGAAACCGGTATT
TGTTGGTGGCGTAACAGTTTCTAATGCCACATTACATAACCAAGATGAAATAACCCGATTAGGGCTGA
AAGTGAATGATTTCGTGGTTATCCGCCGTGCCGGTGATGTTATTCCTCAAATTGTTAGCGTAGTACTT
GATAAACGACCAGATAATGCCGTCGATATAGTCTTTCCTACCAGTTGCCCTGTTTGTGACTCTGCAGT
GGCTAAACCTGAAGGTGAAGCCGTACTGAGATGTACCGCCGGACTTTTCTGTGCGGCGCAAAGAAAAG
AAGCTATTAAACATTTTGCTTCTCGAAAAGCACATGATGTTGATGGTTTAGGTGACAAACTAGTAGAG
CAACTTGTAGATGAAAAGTTAATTAATACGCYCGCTGATTTATTCAAATTAACCGAAATACAAGTTAG
TACTATAGATCGTATGGGTAAAAAATCAGCGACCAATTTAATTAATGGACTTGAGCAGGCTAAAAGTA
CCACACTAGCAAAATTTATTTATGGTCTGGGCATACGCGAAGTCGGTGAAGCAACTGCTGCTAATCTA
GCAAATCATTTTTATACCTTAGCGGCAATTGAAAGTGCTTCTCTTGAAGACTTACAAAATGTTTCAGA
TGTTGGCGAAGTCGTTGCCAAAAATATTATTAATTTCTTTAAAGAAGAGCATAACTTAGCGATCGTTT
CTGGACTAAGTGAAGTAATGCACTGGCCAACTATTGAAATAAAGTCAGCTGAGGAGTTACCGCTTGCA
GAGCAGATATTTGTTTTAACAGGCACATTAACCCAAATGGGAAGAACTGAAGCTAAAACAGCCTTACA
GTCCTTGGGAGCTAAAGTATCAGGTAGTGTCTCGAAGAATACACACTTCGTTGTTGCAGGTGATAAAG
CGGGATCTAAACTGACTAAGGCTCAGGATTTAGGTATCTCAGTGCTTACCGAAGATGGGTTAGTAGCG
TTACTTGCCGAACATGGCATAACTATTTGA

SEQ ID NO: 2

MTPVEKKISQLQQQLNQYNHEYYVLDQPSVPDAEYDRLMTALIDLEKTNPELKTIDSPSQKVGGQALK
SFTQVTHQLPMLSLDNVFSLDDFHAFVKRVKDRLNDNQAIVFCAEPKLDGLAVSLRYEHGQLTQAATR
GDGSVGENITTNIRTIKSIPLKLMGTPGKDFPDIVEVRGEVFMPKASFDALNTXAKKRGEKGFANPRN
AAAGSLRQLDSKITAKRNLAFYAYSLGFVGKLSDGGAESTDLTNDFFANSHHERLCQLKRLGLPMCPE
VRLLESEQACDAFYQDILAKRSALSYEIDGTVLKVDEISLQKRLGFVARAPRWAIAYKFPAEEELTCV
EDVEFQVGRTGATTPVARLKPVFVGGVTVSNATLHNQDETTRLGLKVNDFVVIRRAGDVIPQIVSVVL
DKRPDNAVDIVFPTSCPVCDSAVAKPEGEAVLRCTAGLFCAAQRKEAIKHFASRKAHDVDGLGDKLVE
QLVDEKLINTXADLFKLTEIQVSTIDRMGKKSATNLINGLEQAKSTTLAKFIYGLGIREVGEATAANL
ANHFYTLAAIESASLEDLQNVSDVGEVVAKNIINFFKEEHNLAIVSGLSEVMHWPTIEIKSAEELPLA
EQIFVLTGTLTQMGRTEAKTALQSLGAKVSGSVSKNTHFVVAGDKAGSKLTKAQDLGISVLTEDGLVA
LLAEHGITI

FIG. 11B

SEQ ID NO: 3

ATGACTCCAAGCATTAGTGAGCAAATAAACCATCTTCGTAGTACGCTTGAACAGCACAGTTACAATTA
TTATGTACTTGATACCCCAGTATTCCTGATGCTGAATACGACCGTTTATTACAACAACTCAGCGCAC
TAGAAACTCAGCACCCAGAATTAATAACTGCCGACTCACCAACCCAAAAAGTGGGCGGTGCTGCGCTA
AGTAAATTTGAGCAAGTAGCGCACCAAGTGCCTATGTTATCGCTTGATAACGCCTTTAGCGAAGATGA
GTTTATTGCCTTTAATCGCCGTATAAAAGAGCGTTTAATGAGTACCGAAGAGCTTACTTTTTGTTGTG
AGCCAAAACTAGATGGCTTAGCTGTGTCGATTATTTATCGTGATGGCGTACTAGTGCAAGCCGCGACC
CGAGGTGATGGGTTGACGGGAGAAAATGTAACTCAAAACGTTAAAACAATTCGTAATGTGCCACTTAA
ATTACGAGGTAGCGATTATcCTGCTGAACTAGAAGTGCGCGGCGAAGTGTTTATGGATAATGCAGGCT
TTGAAAAGTTTAACATTGAAGCTGAAAAACGTGGTGAAAAAGTATTTGTAAACCCACGCAACGCCGCC
GCAGGTAGCCTGCGCCAGCTTGACTCTAAAATTACGGCTAAACGCCCACTGATGTTTTATGCCTACAG
CACAGGTCTTGTAGCCGACGGTAGCATTGCAGAGGATCATTATCAGCAATTAGAAAAATTGACTGATT
GGGGGTTACCACTTTGCCCTGAAACAAAATTAGTAGAAGGCCCACAAGCTGCACTGGCTTATTATACT
GACATTTTAACGCGCCGTGGCGAGCTTAAATATGAAATAGATGGCGTGGTAATaAAATaAATCAAAA
AGCCTTACAAGAGCGTTTAGGCTTTGTAGCACGCGCTCCGCGTTGGGCTATTGCTTATAAGTTCCCGG
CCCAAGAAGAAATAACCAAATTACTCGATGTAGAGTTTCAGGTGGGCGTACGGGAGCAATTACACCG
GTTGCACGCTTAGAGCCGGTATTTGTTGGTGGTGTTACTGTATCAAACGCTACCTTGCACAATGGCGA
TGAAATAGCGCGCTTAGGCGTAAAAGTGGGCGACACGGTAATTATTCGCCGTGCAGGGGACGTAATTC
CACAAATAACGCAAGTAGTACTTGAGCGCCGCCCTGATGATGCCCGCGATATTGAGTTtCCGGTaACT
TGCCCAATTTGTGACTCCCATGTAGAAAAAGTAGAAGGTGAAGCCGTAGCGCGTTGTACTGGTGGTTT
AGTGTGCCCGGCGCAACGTAAACAAGCGATtAAACACTTtGCATCGCGCAAAGCACTCGATATTGACG
GCCtTGGCGATAAAATTGTTGATCaACTCGTCGACAGAGAGCTGATTAAAACCCCTGCAGATTTGTTT
ATTTTAAAGCAAGGACATTTTGAATCGCTTGAGCGTATGGGGCCAAAGTCGGCTAAAAATTTGGTTAC
TGCGCTTCAAGACGCTAAAGCAACAACTTTGGCTAAGTTTTTATACTCATTGGGTATTCGTGAAGCGG
GTGAGGCAACCACACAAAATTTAGCTAATCATTTCTTAACCCTTGAAAACGTAATAAATGCCAGCATT
GATAGTTTAACTCAAGTAAGTGATGTGGGCGAAATAGTAGCAACCCATGTACGTAGCTTTTTTGCCGA
ACAGCATAATTTAGATGTTGTAAATGCGCTGGTAGAGCAAGGTATTAATTGGCCTGAACTTACTCCAC
CTTCAGCGCAAGAGCAGCCATTAGCTGGCCTTGTTTATGTGCTTACCGGTACCTTAAACACATTAAAC
CGTAATGACGCCAAAGCACGTTTGCAACAGTTAGGTGCTAAAGTGTCGGGTAGTGTGTCGGCTAAAAC
CGATGCGTTAGTAGCAGGCGAAAAGGCCGGCTCTAAACTAACTAAGGCACAAGACTTAGGTATAGATG
TACTGACAGAAGAAGATTTAATTAATTTATTAGAGCAACATAATGGCTGA

SEQ ID NO: 4

MTPSISEQINHLRSTLEQHSYNYYVLDTPSIPDAEYDRLLQQLSALETQHPELITADSPTQKVGGAAL
SKFEQVAHQVPMLSLDNAFSEDEFIAFNRRIKERLMSTEELTFCCEPKLDGLAVSIIYRDGVLQAAT
RGDGLTGENVTQNVKTIRNVPLKLRGSDYPAELEVRGEVFMDNAGFEKFNIEAEKRGEKVFVNPRNAA
AGSLRQLDSKITAKRPLMFYAYSTGLVADGSIAEDHYQQLEKLTDWGLPLCPETKLVEGPQAALAYYT
DILTRRGELKYEIDGVVIKINQKALQERLGFVARAPRWAIAYKFPAQEEITKLLDVEFQVGRTGAITP
VARLEPVFVGGVTVSNATLHNGDEIARLGVKVGDTVIIRRAGDVIPQITQVVLERRPDDARDIEFPVT
CPICDSHVEKVEGEAVARCTGGLVCPAQRKQAIKHFASRKALDIDGLGDKIVDQLVDRELIKTPADLF
ILKQGHFESLERMGPKSAKNLVTALQDAKATTLAKFLYSLGIREAGEATTQNLANHFLTLENVINASI
DSLTQVSDVGEIVATHVRSFFAEQHNLDVVNALVEQGINWPELTPPSAQEQPLAGLVYVLTGTLNTLN
RNDAKARLQQLGAKVSGSVSAKTDALVAEKAGSKLTKAQDLGIDVLTEEDLINLLEQHNG

FIG. 11C

SEQ ID NO: 5

ATGACTCCAAGCATTAGTGAGCAAATAAACCATCTTCGTAGTACGCTTGAACAGCACAGTTACAATTA
TTATGTACTTGATACCCCCAGTATTCCTGATGCTGAATACGACCGTTTATTACAACAACTCAGCGCAC
TAGAAAACTCAGCACCCAGAATTAATAACTGCCGACTCACCAACCCAAAAAGTGGGCGGTGCTGCGCTA
AGTAAATTTGAGCAAGTAGCGCACCAAGTGCCTATGTTATCGCTTGATAACGCCTTTAGCGAAGATGA
GTTTATTGCCTTTAATCGCCGTATAAAAGAGCGTTTAATGAGTACCGAAGAGCTTACTTTTTCTTGTG
AGCCAAAACTAGATGGCTTAGCTGTGTCGATTATTTATCGTGATGGCGTACTAGTGCAAGCCGCGACC
CGAGGTGATGGGTTGACGGGAGAAAATGTAACTCAAAAAGTTAAAACAATTCGTAATGTGCCACTTAA
ATTACGAGGTAGCGATTATCCTGCTGAACTAGAAGTGCGCGGCGAAGTGTTTATGGATAATGCAGGCT
TTGAAAAGTTTAACATTGAAGCTGAAAAACGTGGTGAAAAAGTATTTGTAAACCCACGCAACGCCGCC
GCAGGTAGCCTGCGCCAGCTTGACTCTAAAATTACGGCTAAACGCCCACTGATGTTTTATGCCTACAG
CACAGGTCTTGTAGCCGACGGTAGCATTGCAGAGGATCATTATCAGCAATTAGAAAAATTGACTGATT
GGGGGTTACCACTTTGCCCTGAAACAAAATTAGTAGAAGGCCCACAAGCTGCACTGGCTTATTATACT
GACATTTTAACGCGCCGTGGCGAGCTTAAATATGAAATAGATGGCGTGGTAATAAAAATAAATCAAAA
AGCCTTACAAGAGCGTTTAGGCTTTGTAGCACGCGCTCCGCGTTGGGCTATTGCTTATAAGTTCCCGG
CCCAAGAAGAAATAACCAAATTACTCGATGTAGAGTTTCAGGTGGGGCGTACGGGAGCAATTACACCG
GTTGCACGCTTAGAGCCGGTATTTGTTGGTGGTGTTACTGTATCAAACGCTACCTTGCACAATGGCGA
TGAAATAGCGCGCTTAGGCGTAAAAGTGGGCGACACGGTAATTATTCGCCGTGCAGGGGACCTAATTC
CACAAATAACGCAAGTAGTACTTGAGCGCCGCCCTGATGATGCCCGCGATATTGAGTTTCCGGTAACT
TGCCCAATTTGTGACTCCCATGTAGAAAAAGTAGAAGGTGAAGCCGTAGCGCGTTGTACTGGTGGTTT
AGTGTGCCCGGCGCAACGTAAACAAGCGATTAAACACTTTGCATCGCGCAAAGCACTCGATATTGACG
GCCTTGGCGATAAAATTGTTGATCAACTCGTCGACAGAGAGCTGATTAAAACCCCTGCAGATTTGTTT
ATTTTAAAGCAAGGACATTTTGAATCGCTTGAGCGTATGGGGCCAAAGTCGGCTAAAAATTTGGTTAC
TGCGCTTCAAGACGCTAAAGCAACAACTTTGGCTAAGTTTTTATACTCATTCGGTATTCGTGAAGCGG
GTGAGGCAACCACACAAAATTTAGCTAATCATTTCTTAACCCTTGAAAACGTAATAAATGCCAGCATT
GATAGTTTAACTCAAGTAAGTGATGTGGGCGAAATAGTAGCAACCCATGTACGTAGCTTTTTTGCCGA
ACAGCATAATTTAGATGTTGTAAATGCGCTGGTAGAGCAAGGTATTAATTGGCCTGAACTTACTCCAC
CTTCAGCGCAAGAGCAGCCATTAGCTGGCCTTGTTTATGTGCTTACCGGTACCTTAAACACATTAAAC
CGTAATGACGCCAAAGCACGTTTGCAACAGTTAGGTGCTAAAGTGTCGGGTAGTGTGTCGGCTAAAAC
CGATGCGTTAGTAGCAGGCGAAAAGGCCGGCTCTAAACTAACTAAGGCACAAGACTTAGGTATAGATG
TACTGACAGAAGAAGATTTAATTAATTTATTAGAGCAACATAATGGCTGA

SEQ ID NO: 6

MTPSISEQINHLRSTLEQHSYNYYVLDTPSIPDAEYDRLLQQLSALETQHPELITADSPTQKVGGAAL
SKFEQVAHQVPMLSLDNAFSEDEFIAFNRRIKERLMSTEELTFCCEPKLDGLAVSIIYRDGVLVQAAT
RGDGLTGENVTQKVKTIRNVPLKLRGSDYPAELEVRGEVFMDNAGFEKFNIEAEKRGEKVFVNPRNAA
AGSLRQLDSKITAKRPLMFYAYSTGLVADGSIAEDHYQQLEKLTDWGLPLCPETKLVEGPQAALAYYT
DILTRRGELKYEIDGVVIKINQKALQERLGFVARAPRWAIAYKFPAQEEITKLLDVEFQVGRTGAITP
VARLEPVFVGGVTVSNATLHNGDEIARLGVKVGDTVIIRRAGDVIPQITQVVLERRPDDARDIEFPVT
CPICDSHVEKVEGEAVARCTGGLVCPAQRKQAIKHFASRKALDIDGLGDKIVDQLVDRELIKTPADLF
ILKQGHFESLERMGPKSAKNLVTALQDAKATTLAKFLYSLGIREAGEATTQNLANHFLTLENVINASI
DSLTQVSDVGEIVATHVRSFFAEQHNLDVVNALVEQGINWPELTPPSAQEQPLAGLVYVLTGTLNTLN
RNDAKARLQQLGAKVSGSVSAKTDALVAGEKAGSKLTKAQDLGIDVLTEEDLINLLEQHNG

FIG. 11D

SEQ ID NO: 7

ATGACTCCAATTCAAACTGAAATGGATCAACTTACTCACACCATTAACCAACATAATATTCGTTATTA
CGTTGATGATGCTCCGTCAATACCCGATGCTGAATACGACAGATTAATTAAGCGCTTAACTGAGTTAG
AACGTGACTATCCGCAATTTAAATCGGTAGATTCACCGACACAACGCGTCGGTGGTATAGCATTACAA
AAATTTGCTCAAATTACCCACCTTAAACCGATGTTAAGTCTCGACAATGCGTTTGAACAAGCCGATTT
TGCAGCATTTAATAAGCGTATAACTGATAAAGTCGATAGCGTCGATTATGTTTGCGAACCAAAACTAG
ACGGATTGGCCGTGAGTATTACTTATCGTTTTGGCGTTCTTGAACGCGCCGCAACGCGAGGTGATGGC
AGTGTCGGCGAAGATATTACCGCTAATGTGCGTACTATTCGTTCAATTCCTCTTAAGTTACGCGGTGA
AGGATTTCCAGATTTAGTTGAAGTACGTGGCGAAGTGTTTATGCCTAAAGCGGCATTTGAGGCATTAA
ACCAGCGTCAAATCAGCAAAGGTGACAAAGTCTTTGTTAATCCTCGCAACGCAGCTGCCGGCAGTTTG
CGCCAATTAGACAGTAAAATTACCGCTTCAAGGGCTCTTGGTTTTATGCTTATGCATTAGGTGTAGT
CGAAGGCGAGTCACAACCGATGCAAACAAGCCACTATGGCCAACTAACACAGCTGCAACAATGGGTA
TTCCCGTTAGTAGTGAAGTGAAAGTGACTGATTTATTAGAAAAAGTCTATGCATATTACGCCGATATT
ATGGCCAGACGAAGTGCGCTTGAATATGAAATTGACGGCGTCGTCATAAAGGTTAATGACATTGCCAA
GCAACAAACACTTGGTTTTGTGGCTAAAGCTCCTCGATGGGCCATAGCCTATAAATTTCCAGCCCAGG
AAGAAATGACCTTGTTAGAGTCTGTTGACTTTCAGGTTGGCCGAACGGGTGCTGTTACCCCTGTCGCT
CGCCTCAAACCGATATTTGTCGGTGGCGTGACTGTGTCGAATGCGACCTTGCACAATGCTGATGAAAT
TGCCCGTCTTGGGGTGAAAATAGGCGATACAGTGATTATTCGCCGCGCAGGTGACGTTATCCCGCAAA
TTGTTGCTATCGTGCCAGAAAAGCGCCCTGATGATGCACAAGATATTATCTTTCCACTGCATTGTCCT
GTGTGCCAAAGCATTGTTGAGCGTTTAGAAGGTGAAGCTGTAGCGCGTTGTAGTGGTGGACTTTTTTG
TGAAGCGCAACGTAAAGAGGCGATTAAACATTTTGCATCCCGTAAAGCATTAAATATTGATGGCATGG
GCGATAAAATCGTTGAGCAATTAATTGATAAAGAACTAGTCAAAACGCCAGCAGACTTGTTTTCCCTT
ACCGCTTCTAGCATCACGATGTTAGATCGCATGGCGATGAAGTCAGCCACAAATATTGTCGCGGCGAT
TAAACACGCTAAAGCCACTACATTAGCGCGTTTTTTATATAGTCTTGGGATCCGCGAAGTCGGCGAAG
CTACCGCCGCTAATTTAGCCCAACACTTTGCCGAATTTGAGCGTATTCGAACTGCTAGCGTTGAACAA
CTGCTCGAAGTCGCTGATGTTGGTGACATTGTAGCAAAACACATTCGACAATTTTTTGCACAGCCACA
TAACATTGAAGTAATAGAGCAATTGCTTGAAGCCGGCATTACTTGGCCTGTTATTGAACAAGCTGACG
AATCGCAGCTTAGTCTTAAAGGCAAACGTGGTGTTAACTGGTACGCTAACTCAACTTAATCGTAAC
GATGCCAAAGCCCAATTACAGGCTTTGGGCCCCAAAGTGGCTGGCAGTGTTTCGAAAAATACTGATTG
CCTTGTTGCTGGTGAAGCAGCGGGTTCTAAATTAGCAAAAGCTGAAGAATTGGCGTTAAGGTCATAG
ATGAACAAGCTCTGATGGATTTATTGAATGCGGCTAAC<u>TGA</u>

SEQ ID NO: 8

<u>M</u>TPIQTEMDQLTHTINQHNIRYYVDDAPSIPDAEYDRLIKRLTELERDYPQFKSVDSPTQRVGGIALQ
KFAQITHLKPMLSLDNAFEQADFAAFNKRITDKVDSVDYVCEPKLDGLAVSITYRFGVLERAATRGDG
SVGEDITANVRTIRSIPLKLRGEGFPDLVEVRGEVFMPKAAFEALNQRQISKGDKVFVNPRNAAAGSL
RQLDSKITASRALGFYAYALGVVEGESQPMQTSHYGQLTQLQQWGIPVSSEVKVTDLLEKVYAYYADI
MARRSALEYEIDGVVIKVNDIAKQQTLGFVAKAPRWAIAYKFPAQEEMTLLESVDFQVGRTGAVTPVA
RLKPIFVGGVTVSNATLHNADEIARLGVKIGDTVIIRRAGDVIPQIVAIVPEKRPDDAQDIIFPLHCP
VCQSIVERLEGEAVARCSGGLFCEAQRKEAIKHFASRKALNIDGMGDKIVEQLIDKELVKTPADLFSL
TASSITMLDRMAMKSATNIVAAIKHAKATTLARFLYSLGIREVGEATAANLAQHFAEFERIRTASVEQ
LLEVADVGDIVAKHIRQFFAQPHNIEVIEQLLEAGITWPVIEQADESQLSLKGQTWVLTGTLTQLNRN
DAKAQLQALGAKVAGSVSKNTDCLVAGEAAGSKLAKAEELGVKVIDEQALMDLLNAAN

FIG. 11E

SEQ ID NO: 9

ATGAATTCTAACACTAAAATTATTTTCGTCACAGGTGGGGTAGTATCATCACTTGGTAAGGGTGTAAC
TGCGGCATCTTTGGCTACTCTCTTAGAAAGTCGTGGTCTTAATGTAACAATGATGAAGCTTGATCCAT
ACATCAATGTTGATCCAGGGACTATGAGTCCATTGCAACATGGTGAAGTTTTTGTAACCGAAGATGGC
GCAGAGACTGATCTTGATTTAGGTCATTATGAGCGCTTTATCCGCAATAAGATGACTCAAGCAAATAA
CTTCACAACCGGTAAAGTATACCAGAGTGTGTTAAGAAGAGAGCGTAAGGGTGATTATCTAGGTGCTA
CTATCCAGGTGATTCCACATATCATTGATGAGATCAAAAGGCGTATTTGTAGTGGTATTGCTGATGAT
GTTGATGTTGCGATTGTTGAGATTGGTGGTACTGTTGGTGATATCGAGTCACAACCATTTTTAGAAGC
TATTCGTCAATTGGCATTAGAGGTAGGTCGTGATCGTGCTATGTTTATGCATTTGACCTTAGTGCCAT
ATTTAGCACCAGCAGGTGAAATCAAAACTAAACCAACACACCACTCACTAAAAGATTTACGCTCTATC
GGTATTTTTCCTGACATTTTAGTATGTCGTTCAGACCGCGCTATTCCTAACGCCAACGCGCTAAAAT
ATCTCTCTTCACTAATGTTGAAGAGAAAGCGGTTGTATCAATGCGTGATGTAGACAGTATTTATAAGA
TTCCTGCTTTATTAAAAGCTCAAGGTACCGATGAAATAGTTGTTAAGCGATTTGGTTTAGATGTACCT
GAAGCCGACTTAACTGAATGGGAAGAAGTGCTTTACCATGAAGCAAATCCTATCGGTGAAGTGACTAT
TGGTATGGTTGGTAAATACACTGAATTACCTGATGCGTACAAATCAGTAAACGAAGCGTTAAAACATG
CAGGTCTTAAAAACCAAGTCACTGTAAATATTAAATACATTGACTCGCAAGATGTAGAAGTCAAACGT
GTTGAAATCTTAGCTAACTTGGATGCTATTTTAGTTCCTGGTGGTTTCGGTGAACGTGGTGTTGAAGG
TAAAATTTTAACGGCACAATATGCGCGTGAAAACAAAGTACCTTATTTAGGTATTTGTTTAGGTATGC
AAGTAGCCTTAATTGAATTTGCTCGTAATGTTGCCGGTTTAACTGATGCGCACAGTACTGAATTTAAT
AGCGAAACTCCACACCCAGTGGTTGGTTTAATCAGTGAATGGTTAGACGAAGAAGGCCAAGTTGAGTA
CCGAAATGAGCAATCAGATTTACGTGGCTACTATCCGTTTACGTTCACAATTGTGCCACTTGCTGAAAG
GTACCAAGGCTTGCGACGTATATGGTAGTGAAACAATCAATGAGAGACACCGTCATCGTTTTGAGGTA
AATAATAACTACCGAGAACAATTAAGCAAAGCAGGTTTGATTTTCTCGGGTTTATCGTCAGATAAAAG
TTTAGTTGAGGTGATTGAAATAGCGGATCATCCATGGTTTATTGCGGGTCAATTCCATCCTGAGTTTA
ATTCTACTCCACGTGATGGTCACCCGTTATTCGAAAGCTTTGTTGCAGCGAGTTTTAAACTGCAAAAT
AATTAG

SEQ ID NO: 10

MNSNTKIIFVTGGVVSSLGKGVTAASLATLLESRGLNVTMMKLDPYINVDPGTMSPLQHGEVFVTEDG
AETDLDLGHYERFIRNKMTQANNFTTGKVYQSVLRRERKGDYLGATIQVIPHIIDEIKRRICSGIADD
VDVAIVEIGGTVGDIESQPFLEAIRQLALEVGRDRAMFMHLTLVPYLAAAGEIKTKPTQHSVKDLRSI
GIFPDILVCRSDRAIPNAERAKISLFTNVEEKAVVSMRDVDSIYKIPALLKAQGTDEIVVKRFGLDVP
EADLTEWEEVLYHEANPIGEVTIGMVGKYTELPDAYKSVNEALKHAGLKNQVTVNIKYIDSQDVEVKG
VEILANLDAILVPGGFGERGVEGKILTAQYARENKVPYLGICLGMQVALIEFARNVAGLTDAHSTEFN
SETPHPVVGLISEWLDEEGQVEYRNEQSDLGGTMRLGSQLCHLVKGTKACDVYGSETINERHRHRFEV
NNNYREQLSKAGLIFSGLSSDKSLVEVIEIADHPWFIAGQFHPEFNSTPRDGHPLFESFVAASFKLQN
N

FIG. 11F

SEQ ID NO: 11

ATGAAACAAACTACAGTACGAATTGCCACGCGTAAAAGCGCCCTCGCCTTATGGCAAGCAGAATATGT
TAAAGCGCAACTTGAGCATTTTCATGACGGTATTAATGTTGAATTAGTGCCTATGACAACGAAAGGCG
ACATCATTTTAGACACGCCTTTAGCCAAAGTCGGCGGTAAAGGTTTATTTGTTAAAGAGCTTGAAGTA
GCAATGCTTGAAGACCGTGCTGATATTGCTGTTCATTCAATGAAAGATGTTCCTGTCGATTTTCCAGA
AGGCTTAGGATTAGAAGTCATTTGTCCTCGTGAAGATCCCCGTGATGCTTTTGTTCTAATACCATCA
AATCATTAAGTGATTTACCACAAGGCTCTATTGTTGGCACCTCAAGCTTACGCCGTCAGTGTCAATTA
AAAGCAAGCCGCCCTGATTTAGATATTCGTGATTTACGTGGCAATGTAAATACCCGCCTAAGAAAATT
AGATGAAGGTCAGTACGACGCTATTATATTAGCCGCTGCAGGCCTAATTCGCTTAGAAATGAGCGAGC
GTATTGCACAGTTTATCGAACCAGAAGAAATGCTTCCTGCAAATGGCCAAGGCGCTGTTGGCATTGAA
TGTCGTAATGATGATGCGACAATTAAAGCCTTATTAGCACCATTAGAATGTGCTACCACCCGTATTCG
TGTTCTTGCAGAACGTGCAATGAATAGAGCATTACAAGGCGGTTGCCAGGTTCCTATCGGTAGCTATG
GTGTTATTTCTGCTGATGGTAAAAATATCCACTTACGTGGCTTAGTTGGCTCTGTCGATGGTAGTGAA
ATGATAGAAAGTGAAATCACCGGCCCTGTTGAAGAAGGTGAAGCGCTCGGCAATAAACTCGCGCAAGA
GTTACTAAGCCGAGGTGCAGATAAAATTTTACAGCAAGTTTATTCAGAAAATGATATCAAAGAGAGTT
AA

SEQ ID NO: 12

MKQTTVRIATRKSALALWQAEYVKAQLEHFHDGINVELVPMTTKGDIILDTPLAKVGGKGLFVKELEV
AMLEDRADIAVHSMKDVPVDFPEGLGLEVICPREDPRDAFVSNTIKSLSDLPQGSIVGTSSLRRQCQL
KASRPDLDIRDLRGNVNTRLRKLDEGQYDAIILAAAGLIRLEMSERIAQFIEPEEMLPANGQGAVGIE
CRNDDATIKALLAPLECATTRIRVLAERAMNRALQGGCQVPIGSYGVISADGKNIHLRGLVGSVDGSE
MIESEITGPVEEGEALGNKLAQELLSRGADKILQQVYSENDIKES

SEQ ID NO: 13

ATGAAAAAACCACTAAATATCATTTTTGCAGGTACTCCTGAATTCGCTGCCCAACATTTAGCAGCGTT
AATTAATTCTGAACATAATATTGTCGCCGTTTATTGTCCCCCTGATAAACCAGCTGGCCGCGGTAAAA
AACTAACAGCTTGTGCAACAAAGTTACTCGCAATAGAGCACGACATTATTGTTGAGCAACCTATTAAC
TTTAAAAATGAGGAAGACCAACAACAATTAGCGAAATATAACGCTGATATCATGGTTGTTGTTGCTTA
TGGTCTGCTATTACCTGAAGTCATTTTAAACTCTCCACGTTTAGGCTGCATTAACGTACATGGCTCAA
TTCTACCAAAATGGCGTGGTGCAGCACCTATTCAACGTTCTCTTGAAGCTGGAGATAAGAAAACCGGT
GTCACCATTATGCAAATGGATAAAGCCTTAGACACGGGAGACATGATTCTATCCGCTGACTGCCAAAT
AGAAAATACAGATACCAGTGCAAGTCTTTATGAAAAACTTGCCAACTTAGGGCCAACTGCCTTAGTTA
ATACATTAACTATTATGGCTGAACCTGATTATCAAGCCAGTAATCATAATATCGCTCAAGATGATGAA
TTAGCGACTTATGCCAAGAAACTTGATAAAACTGAAGCAGAGCTTAACTGGCAATTCAGTGCTGATGA
ACTACATCGAAAAATTCGTGCTTATATTCCTTGGCCAGTTGCTCAATTTACCTTTACAGAATCTGAAG
GTAAGCAGCATAGGTTACGCATATGGCAAGCATCCGTGCAAGAATATCGAGGCAATGCTGATCCAGGC
ACGATAATAAAGGCAGACAAAGAAGGGATAGAAGTAGCAACAACCAGTGGTTCGTTACGACTAGAAGT
CATTCAACTTCCAGGGAAAAAAGCATTAGCCGTAAAAGACATCCTAAATGGTCGCAGCGATTGGTTCG
TTGTTGGCAGCACTATTAACAAGCTAGGATAA

SEQ ID NO: 14

MKKPLNIIFAGTPEFAAQHLAALINSEHNIVAVYCPPDKPAGRGKKLTACATKLLAIEHDIIVEQPIN
FKNEEDQQQLAKYNADIMVVVAYGLLLPEVILNSPRLGCINVHGSILPKWRGAAPIQRSLEAGDKKTG
VTIMQMDKGLDTGDMILSAECEIENTDTSASLYEKLANLGPTALVNTLTIMAEPDYQASNHNIAQDDE
LATYAKKLDKTEAELNWQFSADELHRKIRAYIPWPVAQFTFTESEGKQHRLRIWQASVQEYRGNADPG
TIIKADKEGIEVATTSGSLRLEVIQLPGKKALAVKDILNGRSDWFVVGSTINKLG

FIG. 11G

SEQ ID NO: 15

ATGAGTCTAAATCATGGCCAAGGTAATAAAGATTTAGCAAAAACTTTGTTAGTCATGGCTGGTGGCAC
CGGTGGACATATATTCCCTGGTATTGCGGTCGCCGATGAGCTGAAAGCGCAAGGATGGAAAATCCATT
GGTTGGGAACTGCCGATCGTATGGAAGCTCAAATTGTACCTATGCATGGTTATGATATTTCGTTTATC
AATATAAGTGGTCTGCGTGGTAAAAATCTATTAACAACGCTTGTTATGCCTTTTAAATTGTTAAGGTC
GCTTTTTCAAGCGAGACGCGTGATTAAAACAGTGAAACCTGATGTTGTTATAGGCATGGGTGGCTATG
CAAGTGCTCCGGGTGGTTTGGCCGCTTGGCTAAGTAAAATACCGCTAATCGTTCATGAACAAAATGCT
GCTGCCGGATTAAGTAATCGCTTGTTAGCGCGTATCGCCAATAAAGTATGCTGCGCCTTTCCTAATGC
ATTTGTTAGCGGAATTGATGTTGAAGTGGTTGGTAATCCTTTACGCGCGTCAATCGGTCAGCAAGCAC
TGGTTTCAGAAAATATAGATCAAAGCCACGAAGGTAGTAAAAATATTCTAGTGGTAGGTGGTAGTTTA
GGCGCTCAAGTCTTAAATAAGGTGATGCCGGATAGCTTTAAGGATTTATCAGAAAGTGATGAGAAATA
TTGTATATGGCACCAAACGGGCGACAATAACCAAGCACTAGTCACCGCATCTTATAAACAGGAATATA
TTGATACTGGAAAAGTGAGAGTTACCGAATTTATTACTGATATTGCTGCTGCATATCAGTGGGCTGAT
ATAGTGATTTGTCGTGCGGGAGCGCTAACCGTTTCAGAATTAGCCATGGCAGCAACACCAGCCATTTT
TGTACCACTACCGCATGCAGTAGATGATCATCAAACAAAAAATGCGTTGTACCTCGTAAAGCGAGATG
CAGCAAAGTTATTGCCACAGGCAGAACTAAATAATGAGAGTATCACGTCGTTAATAATCGAGCTGTTT
GATCAGCCTCAAACTTTAGCTGACATGGCTAAAGCTTCTTTGAGTGCTGCAACTAGTGATGCAAGTCA
GAAAGTAGCAAAATTGTGCCAACAGCTTTCAATATCGAATGGCGCAAAACTTAGAAATAATGAAGAGA
ACAAATAA

SEQ ID NO: 16

MSLNHGQGNKDLAKTLLVMAGGTGGHIFPGIAVADELKAQGWKIHWLGTADRMEAQIVPMHGYDISFI
NISGLRGKNLLTTLVMPFKLLRSLFQARRVIKTVKPDVVIGMGGYASAPGGLAAWLSKIPLIVHEQNA
AAGLSNRLLARIANKVCCAFPNAFVSGIDVEVVGNPLRASIGQQALVSENIDQSHEGSKNILVVGGSL
GAQVLNKVMPDSFKDLSESDEKYCIWHQTGDNNQALVTASYKQFYIDTGKVRVTEFITDIAAAYQWAD
IVICRAGALTVSELAMAATPAIFVPLPHAVDDHQTKNALYLVKRDAAKLLPQAELNNESITSLIIELF
DQPQTLADMAKASLSAATSDASQKVAKLCQQLSISNGAKLRNNEENK

FIG. 11H

SEQ ID NO: 17

GTGAGCGAGAAGGAGAAGAAAATATCCCAGCTGCAACAGCAACTGAACCAATATAACCATGAGTACTA
TGTCCTCGACCAGCCATCGGTCCCCGATGCGGAGTACGATCGCCTGATGACCGCGTTAATCGATCTGG
AAAAGACCAACCCCGGAGTTGAAGACGATCGACAGTCCGTCGCAGAAGGTGGGCGGTCAGGCCCTGAAG
AGCTTCACCCAAGTGACGCATCAGCTGCCCATGCTCTCGCTTGACAACGTCTTTTCCCTGGATGACTT
CCACGCCTTCGTCAAGAGGGTCAAAGACCGTCTCAATGACAACCAGGCGATCGTGTTCTGTGCCGAGC
CGAAGCTGGACGGCCTCGCGGTATCGCTCCGCTACGAGCATGGCCAGCTCATCCAGGCGGCCACGCGG
GGCGACGGCTCAGTCGGGGAGAATATCACCACGAACATCCGGACGATCAAGTCCATCCCCCTGAAGCT
CATGGGCACTCCCGGCAAAGACTTTCCAGACATTGTGGAAGTCCGGGGCGAAGTGTTCATGCCGAAGG
CCTCGTTCGACGCGCTGAACACCCTGGCTAAGAAACGGGGGGAGAAGGGCTTCGCTAACCCGCGGAAC
GCGGCAGCCGGCAGTCTGCGTCAGCTGGACAGCAAGATCACGGCCAAGCGCAACCTGGCGTTCTATGC
CTACAGCCTAGGTTTCGTGGGGAAACTGAGCGACGCGGGCGCGGAAAGCACCGACTTGACGAACGACT
TTTTCGCGAACTCGCACCATGAGCGATTGTGTCAATTGAAGCGACTGGGTTTGCCGATGTGTCCGGAG
GTGCGGCTGCTAGAATCGGAGCAGGCTTGCGACGCGTTCTACCAGGACATCCTCGCGAAGCGCTCGGC
TCTTTCATACGAAATCGACGGTACCGTTTTGAAGGTTGACGAGATCTCCCTCCAGAAGCGCCTGGGTT
TCGTGGCGCGGGCACCGCGCTGGGCCATCGCCTACAAGTTCCCAGCAGAGGAAGAGCTGACCTGCGTG
GAGGACGTAGAATTTCAAGTGGGCCGCACCGGTGCCATCACCCCGGTTGCCCGCCTGAAGCCTGTCTT
CGTGGGCGGTGTCACCGTGAGCAACGCTACCCTTCATAACCAGGACGAGATCACACGTCTGGGGCTGA
AGGTCAACGATTTCGTCGTGATTCGCCGCGCAGGCCACGTTATTCCGCAGATCGTGTCGGTGGTCCTG
GACAAAAGGCCGGATAACGCCGTCGATATCGTCTTCCCCACGTCGTGCCCGGTGTGCGACTCGGCCGT
GGCCAAGCCCGAAGGCGAGGCAGTCCTGCGGTGCACAGCCGGCTCTTCTGTGCGGCCCAGCGCAAGG
AAGCCATCAAGCACTTCGCCTCCCGCAAGGCCCACGACGTCGACGGACTGGGCGACAAGCTCGTCGAG
CAGCTTGTAGACGAGAAGCTGATCAACACCCCCGCGGATCTGTTCAAGCTCACCGAAATCCAGGTGAG
TACCATTGACAGAATGGGAAAGAAGTCTGCCACCAACCTGATAAATGGTCTGGAGCAGGCGAAGAGCA
CTACGCTGGCGAAGTTCATTTACGGCCTGGGGATCCGGGAAGTGGGAGAGGCCACGGCCGCGAACCTG
GCCAACCCACTTCTACACCCTCGCCGCGATCGAGAGCGCCAGCTTGGAGGATCTGCAGAACGTATCCGA
CGTGGGTGAGGTCGTGGCAAAGAACATCATTAATTTCTTCAAGGAAGAGCACAACCTGGCGATCGTCA
GCGGTTTGAGCGAAGTGATGCACTGGCCCACCATCGAGATCAAGTCGGCCGAGGAGCTTCCTCTGGCG
GAGCAGATCTTCGTCCTCACCGGAACTCTCACCCAGATGGGCCGCACGGAGGCGAAGACCGCCTTGCA
ATCCCTGGGCGCTAAGGTCTCGGGCTCCGTCTCCAAGAACACCCACTTCGTGGTTGCGGGCGACAAGG
CTGGCAGCAAGCTGACGAAGGCGCAGGACCTCGGCATCTCAGTCCTGACAGAGGATGGCCTGGTCGCC
CTGCTGGCAGAGCACGGCATCACCATT

SEQ ID NO: 18

MSEKEKKISQLQQQLNQYNHEYYVLDQPSVPDAEYDRLMTALIDLEKTNPELKTIDSPSQKVGGQALK
SFTQVTHQLPMLSLDNVFSLDDFHAFVKRVKDRLNDNQAIVFCAEPKLDGLAVSLRYEHGQLIQAATR
GDGSVGENITTNIRTIKSIPLKLMGTPGKDFPDIVEVRGEVFMPKASFDALNTLAKKRGEKGFANPRN
AAAGSLRQLDSKITAKRNLAFYAYSLGFVGKLSDGGAESTDLTNDFFANSHHERLCQLKRLGLPMCPE
VRLLESEQACDAFYQDILAKRSALSYEIDGTVLKVDEISLQKRLGFVARAPRWAIAYKFPAEEELTCV
EDVEFQVGRTGAITPVARLKPVFVGGVTVSNATLHNQDEITRLGLKVNDFVVIRRAGDVIPQISVVL
DKRPDNAVDIVFPTSCPVCDSAVAKPEGEAVLRCTAGLFCAAQRKEAIKHFASRKAHDVDGLGDKLVE
QLVDEKLINTPADLFKLTEIQVSTIDRMGKKSATNLINGLEQAKSTTLAKFIYGLGIREVGEATAANL
ANHFYTLAAIESASLEDLQNVSDVGEVVAKNIINFFKEEHNLAIVSGLSEVMHWPTIEIKSAEELPLA
EQIFVLTGTLTQMGRTEAKTALQSLGAKVSGSVSKNTHFVVAGDKAGSKLTKAQDLGISVLTEDGLVA
LLAEHGITI

FIG. 11I

SEQ ID NO: 19

ATGGGAAAAATTATTGGTATTGACCTAGGAACAACTAACTCATGTGTTGCTGTTTTAGATGGCGACAG
TGTACGTGTTATTGAAAATGCAGAAGGCGATCGTACAACTCCTTCTATTATTGGTTATACAGCCGAAG
GCGAAACATTAGTAGGTCAACCTGCTAAGCGTCAATCTGTAACTAACCCAGAAAACACTTTATATGCA
ATTAAACGCTTAATCGGTCGTCGTTTCGAAGATAAAGAAACACAACGTGACATCGATATTATGCCATT
TGGTATTGTTAAAGCGGATAACGGTGATGCTTGGGTTCAAGTAAAAGGCGAGAAAATTGCTCCGCCAC
AAGTTTCAGCTGAAGTTCTTAAGAAAATGAAAAAGACTGCTGAAGACTTCTTAGGTGAAACCGTAACT
GAAGCTGTTATTACTGTACCTGCTTACTTTAACGATTCACAACGCCAAGCAACGAAAGATGCTGGTCG
TATTGCTGGTCTTGAAGTCAAACGTATtAtCAACGAACCTACTGCTGCTGCCCTTGCTTACGGCATGG
ACAAACAAGAASGTGACAAAGTTGTTGCAGTTTACGATTTAGGTGGTGGTACATTCGATATTTCAATC
ATTGAAATTGATGAAATGGATGGCGAACACACTTTTGAAGTATTAGCGACTAACGGTGATACTCACTT
AGGTGGTGAAGATTTTGATAACCGTTTAATCAACTACCTTGTAGCTGAATTCAAAAAAGACCAAGGCA
TGGACTTAACGTCTGATCCTTTAGCAATGCAGCGTTTAAAAGAAGCAGCAGAAAAAGCTAAATGTGAA
CTTTCTTCAGCACAACAAACAGATGTAAACTTACCTTACATCACTGCTGATGGTTCAGGTCCTAAGCA
CATGAACATCAAAGTGACTCGTGCTAAGTTAGAATCACTAGTTGAAGATATGGTTAAAGCAACATTAG
AGCCGCTTAAACAAGCGCTTAAAGATGCAGACTTATCAGTAAGCAAGATtGATGAtGTTATTTTAGTT
GGTGGTCAATCTCGTATGCCACTAGTTCAAAAAACTGTTACTGATTTCTTCGGTAAAGAGCCACGTAA
AGATGTTAACCCTGATGAAGCAGTAGCTTCTGGTGCGGCGATTCAAGCGGGTGTTCTTTCTGGTGATG
TGACTGACGTTCTTTTATTAGACGTTACACCACTATCATTAGGTATCGAAACTATGGGCGGTGTGATG
ACTAAGGttAtCGaCAAAaaCaCTACTATcCCAACTAAGCAATCACAAACTTTCTCTACAGCTGATGA
TAACCAAGCTGCAGTAACTGTTCATGTTTGTCAGGGTCAGCGTAAGCAAGCTTCAGCAAACAAATCTT
TAGGTCAATTTAACCTTGAAGGTATTGAACCAGCACAACGTGGTACACCACAAATCGAAGTAACTTTT
GATATTGATGCTGATGGTATCTTGCACGTTACGGCTAAAGATAAGAATACTGGTAAAGAGCAAAAAaT
CACTATCAAAGCCTCTTCTGGTTTATCTGATGAAGAAGTAGAGCAGATGGTACGTGATGCAGAAGCTA
ACGCTGATGCTGATGCTAAATTTGAAGAGCTAGTAACTGCACGTAATCAAGCTGATGGCATGATTCAC
GCGACTCGCAAGCAAGTTGAAGAAGCAGGCGAAGAGTTACCAAGCGAAGATAAAGAAAAAATTGAAGC
AGCATTAACTGAGCTTGAAGAAGCAGTTAAAGGTGATGATAAAGAAGTAATTGAAGCTAAAACTCAAG
CACTTATGGAAGCATCAGCTAAGTTAATGGAAATTGCTCAAGCTAAAGAACAAGCTCAAAGCGCTCCT
GAAGGTGCTCAAGAAGCTGACGCAGCTCCTGCAGACGATGTTGTTGATGCTGAGTTTGAAGAAGTTAA
AGACAAAAAATAA

SEQ ID NO: 20

MGKIIGIDLGTTNSCVAVLDGDSVRVIENAEGDRTTPSIIGYTAEGETLVGQPAKRQSVTNPENTLYA
IKRLIGRRFEDKETQRDIDIMPFGIVKADNGDAWVQVKGEKIAPPQVSAEVLKKMKKTAEDFLGETVT
EAVITVPAYFNDSQRQATKDAGRIAGLEVKRIINEPTAAALAYGMDKQEXDKVVAVYDLGGGTFDISI
IEIDEMDGEHTFEVLATNGDTHLGGEDFDNRLINYLVAEFKKDQGMDLTSDPLAMQRLKEAAEKAKCE
LSSAQQTDVNLPYITADGSGPKHMNIKVTRAKLESLVEDMVKATLEPLKQALKDADLSVSKIDDVILV
GGQSRMPLVQKTVTDFFGKEPRKDVNPDEAVASGAAIQAGVLSGDVTDVLLLDVTPLSLGIETMGGVM
TKVIDKNTTIPTKQSQTFSTADDNQAAVTVIIVCQGERKQASANKSLGQFNLEGIEPAQRGTPQIEVTF
DIDADGILHVTAKDKNTGKEQKITIKASSGLSDEEVEQMVRDAEANADADAKFEELVTARNQADGMIH
ATRKQVEEAGEELPSEDKEKIEAALTELEEAVKGDDKEVIEAKTQALMEASAKLMEIAQAKEQAQSAP
EGAQFADAAPADDVVDAEFEEVKDKK

FIG. 11J

SEQ ID NO: 21 Uppercase Coding sequence; underlined Francisella; normal font Colwellia)

tataaatataATGTCGAGCTTTAACCAAGCATTCGCCGAACTAAAACGCGGAGCAGAAGAAATATTAG
TAGAAGAAGAATTATTAACAAAGCTTAAGACAGGTAAGCCGCTAAAAATCAAAGCGGGTTTTGATCCT
ACTGCGCCTGACTTACATTTAGGCCACACGGTATTAATTAACAAGCTTCGTCAATTCCAACAATTAGG
TCATGAAGTTATTTTCTTGATTGGTGACTTCACCGGAATGATTGGTGATCCAACGGGTAAAAATGTGA
CGCGTAAGGCACTCACTAAAGAAGACGTATTAGCCAATGCTGAAACGTATAAAGAGCAAGTCTTTAAA
ATATTAGATCCCGCTAAAACAACCGTTGCCTTTAACTCTACTTGGATGGATAAATTAGGCGCGGCAGG
TATGTTACAACTTGCCTCTCGTCAAACGGTTGCCCGTATGATGGAGCGTGACGACTTTAAAAAACGTT
ATGCTAACGGCCAGGCCATTGCTATTCATGAGTTTATGTACCCTTTAGTACAAGGTTGGGATTCAGTT
GCGCTTGAGGCTGATGTTGAGCTGGGTGGTACCGACCAAAAGTTTAATTTATTAATGGGTCGTGAGTT
ACAAAAATCTGAAGGCCAGCGTCCACAAACAGTATTAATGATGCCATTACTTGAAGGCCTAGATGGCG
TTCAGAAAATGTCTAAGTCATTAGGCAACTACATTGGCATTACTGATACGCCTACCGACATGTTTGGC
AAAATAATGTCAATTTCAGATGTATTAATGTGGCGTTACTACGAGTTACTTAGCTTTAAACCGCTTGA
AGAAATTGAAGGTTATAAAACCGAGATAGAAAATGGCAAAAATCCTCGTGATGTTAAAATTGATTTAG
CCAAAGAATTGATTGCTCGTTTTCATGATGAAGCTGCTGCACAAGCTGCCCATGATGAATTCATCAAT
CGTTTCCAAAAAGGTGCGTTACCTGATGATATGCCGGAATTAACGATTACCACTGAAAATGGTGAAAT
AGCCATTGCTAACTTGCTTAAAGATGCAGGATTAGTCGGTAGTACTTCTGATGCCTTTAGAATGATCA
AACAAGGGGCGGCTAAAATTGATAGCGAAAAAGTAACTGACCGTAGCTTAGTTATTAGCGCTGGCACG
ACGGCAGTTTATCAAGTCGGCAAACGTAAATTTGCTCGTATTACCATAAAATAAggggttgtaa

SEQ ID NO: 22

MSSFNQAFAELKRGAEEILVEEELLTKLKTGKPLKIKAGFDPTAPDLHLGHTVLINKLRQFQQLGHEV
IFLIGDFTGMIGDPTGKNVTRKALTKEDVLANAETYKEQVFKILDPAKTTVAFNSTWMDKLGAAGMLQ
LASRQTVARMMERDDFKKRYANGQAIAIHEFMYPLVQGWDSVALEADVELGGTDQKFNLLMGRELQKS
EGQRPQTVLMMPLLEGLDGVQKMSKSLGNYIGITDTPTDMFGKIMSISDVLMWRYYELLSFKPLEEIE
GYKTEIENGKNPRDVKIDLAKELIARFHDEAAAQAAHDEFINRFQKGALPDDMPELTITTENGEIAIA
NLLKDAGLVGSTSDAFRMIKQGAAKIDSEKVTDRSLVISAGTTAVYQVGKRKFARITIK

SEQ ID NO: 23 (Uppercase Coding sequence; underlined Francisella; normal font Colwellia)

aagtctagaagATGTCGAAAAACTTGTACAGTTTATGCAGGAATTTGAGAATGAACAATAGCACACCA
GTTATAACCATTGATGGCCCAAGTGGGGCTGGTAAAGGAACCGTTGCAAGGATAGTTGCGGACCAATT
AGGTTGGCACCTTCTTGACAGTGGGGCTATTTACCGCGTCTTAGCTGTTGCCATTCAACATCACCAAC
TTTCATTAGATGATGAAGAGCCTCTTATCCCTATGGCTGCACATTTAGATGTTCAATTTGAAATTAAT
AGTCAAGGTGAAGCTAAAGTTATTTTAGAAGGTGAAAATGTTACTGAAATTATTCGTACTGAAGAAGT
TGGCGGATTAGCATCGAAAGTAGCAGCATTTCCACGTGTTAGAGAAGCGCTATTACGAAGACAACGTG
CATTTAGCGTTAGCCCTGGCTTAATTGCAGATGGTCGCGACATGGGAACCGTTGTTTTTCCGAAAGCT
CCAGTAAAAATATTTTTAACTGCTAGTGCTGAAGAACGAGCTGACCGAAGATTTAATCAGTTGAAAGA
AAAAGGAATTGATGTTAACATCGGGCGCCTTTTGGATGACATACGTCAACGAGATGAGCGAGATCAAA
ACCGCAAGGTAGCTCCTCTTATCCCGGCAGAAGGAGCGTTAACTATTGATTCTACTGATATTTCTATT
ACAGAAGTCGTCAATAAAATCCTTATGTTTGCCAATGGCAAATTAACGTAGatattttagc

SEQ ID NO: 24

MNNSTPVITIDGPSGAGKGTVARIVADQLGWHLLDSGAIYRVLAVAIQHHQLSLDDEEPLIPMAAHLD
VQFEINSQGEAKVILEGENVTEIIRTEEVGGLASKVAAFPRVREALLRRQRAFSVSPGLIADGRDMGT
VVFPKAPVKIFLTASAEERADRRFNQLKEKGIDVNIGRLLDDIRQRDERDQNRKVAPLIPAEGALTID
STDISITEVVNKILMFANGKLT

FIG. 11K

SEQ ID NO: 25(Uppercase Coding sequence; underlined Francisella; normal font Colwellia)

ggagaatcaaATGGGAAAAATTATTGGTATCGATTTAGGCACAACAAACTCGTGTGTAGCAGTCCTTG
ATGGCGGCAAAGCACGCGTAATTGAAAACGCAGAGGGTGATCGCACAACCCCATCAATTATCGCTTAT
ACCGATGATGAAATTATTGTAGGCCAGCCAGCAAAGCGTCAGGCTGTAACCAACCCAACAAACACATT
CTTTGCCATCAAGCGTTTAATCGGTCGTCGTTTTAAAGATGACGAAGTTCAACGTGATGTGAACATCA
TGCCATTCAAAATTATCGCAGCTGATAATGGTGATGCATGGGTTGAGTCACGTGGTAACAAAATGGCA
CCACCACAAGTTTCAGCTGAAATCTTGAAAAAGATGAAAAAGACTGCTGAAGACTTTTTAGGTGAAGA
AGTGACTGAAGCGGTTATTACCGTTCCTGCTTACTTTAACGATTCACAACGTCAAGCCACTAAAGATG
CTGGTCGTATCGCAGGTCTTGATGTTAAGCGTATTATCAACGAACCTACTGCTGCTGCACTTGCATAC
GGTATCGACAAGAAACAAGGCGACAACATTGTTGCTGTATACGATTTAGGTGGTGGTACATTCGATAT
CTCTATCATCGAAATTGACAGCAACGATGGTGACCAAACATTTGAAGTACTAGCAACCAATGGTGATA
CTCACTTAGGTGGTGAAGACTTTGATAACCGTATGATTAACTATTTAGCTGATGAATTCAAAAAAGAC
CAAGGCTTAGATCTTCGTAGAGATCCTTTAGCAATGCAACGTTTGAAAGAAGCCGCTGAAAAAGCAAA
AATCGAGCTTTCAAGCACTAACCACACTGAAGTTAACTTGCCTTACATCACTGCTGATGCATCAGGTC
CTAAGCATTTAGTGGTTAAAATTACTCGTGCTAAGTTAGAGTCATTAGTTGAAGATTTAATTCAACGT
ACTCTAGAGCCGCTTAAAGTTGCACTAGCTGATGCTGATTTATCAATATCAGATATCAATGAAGTGAT
TCTTGTGGGTGGTCAGACTCGTATGCCTAAAGTACAAGAAGCAGTCACTAACTTCTTTGGCAAAGAGC
CTCGTAAAGATGTTAACCCTGATGAAGCGGTTGCTGTTGGTGCGGCGATTCAGGCTGGCGTACTTTCT
GGTGAAGTGAAAGACGTACTTCTACTTGACGTTACCCCACTATCTCTTGGTATTGAAACCATGGGCAG
TGTGATGACAAAGCTTATCGAGAAGAACACCACTATCCCGACTAAAGCTCAGCAAGTATTCTCAACAG
CTGACGACAACCAAAGTGCCGTGACTATTCACGTACTTCAAGGTGAACGTAAGCAAGCGAGTGCTAAC
AAGTCATTAGGTCAATTTAACCTTGAAGGTATTGAGCCAGCACCACGTGGCCAACCACAGGTTGAAGT
GATGTTCGACATTGATGCTGATGGTATCTTACATGTGTCTGCAACAGACAAGAAAACAGGTAAGAAAC
AAAACATTACTATCAAAGCCTCTTCAGGTTTATCTGATGAAGAAGTTGAACAAATGGTACGTGATGCA
GAAGCTCATGCTGATGAAGATGCTAAATTTGAAGAGTTAGTTAAAGCGCGTAATCAAGCAGATGGTTT
AGCTCATTCAACTAAAAAACAAGTTGAAGAAGCTGGCGATGCACTAGCTAGTGACGAAAAAGAAAAGA
TTGAAGCAGCAATCGCAACTTTAGAAACTGCCATAAAAGGCAAAGATAAAGAAGCCATTGATACAGCA
ACTCAAGCGCTAATCGAAGCGTCTGCTAAGTTAATGGAAATTGCTCAAGCTAAAGCTCAAGGTGAAGC
AGAAGGTCAAGCGCACGATGCTGGCCAAGAAAAGCCTGCTGATGATGTTGTTGATGCTGAGTTCGAAG
AAGTTAAAGACGACAAAAAATAAataatctttt

SEQ ID NO: 26

MGKIIGIDLGTTNSCVAVLDGGKARVIENAEGDRTTPSIIAYTDDEIIVGQPAKRQAVTNPTNTFFAI
KRLIGRRFKDDEVQRDVNIMPFKIIAADNGDAWVESRGNKMAPPQVSAEILKKMKKTAEDFLGEEVTE
AVITVPAYFNDSQRQATKDAGRIAGLDVKRIINEPTAAALAYGIDKKQGDNIVAVYDLGGGTFDISII
EIDSNDGDQTFEVLATNGDTHLGGEDFDNRMINYLADEFKKDQGLDLRRDPLAMQRLKEAAEKAKIEL
SSTNHTEVNLPYITADASGPKHLVVKITRAKLESLVEDLIQRTLEPLKVALADADLSISDINEVILVG
GQTRMPKVQEAVTNFFGKEPRKDVNPDEAVAVGAAIQAGVLSGEVKDVLLLDVTPLSLGIETMGSVMT
KLIEKNTTIPTKAQQVFSTADDNQSAVTIHVLQGERKQASANKSLGQFNLEGIEPAPRGQPQVEVMFD
IDADGILHVSATDKKTGKKQNITIKASSGLSDEEVEQMVRDAEAHADEDAKFEELVKARNQADGLAHS
TKKQVEEAGDALASDEKEKIEAAIATLETAIKGKDKEAIDTATQALIEASAKLMEIAQAKAQGEAEGQ
AHDAGQEKPADDVVDAEFEEVKDDKK

FIG. 11L

SEQ ID NO: 27(Uppercase Coding sequence; underlined Francisella; normal font Colwellia)

ATGTTTGATTTTAACGATTCAATGGTTTCAAATGCCATAATTAAAGTTGTCGGTGTTGGTGGCGGTGG
CGGTAATGCTGTACAACATATGTGTGAAGAAGTTTCTGATGTTGAGTTTTTTGCCCTAAATACAGATG
GTCAAGCATTATCAAAATCAAAAGTTCAAAATATATTACAAATTGGTACAAACCTAACAAAAGGTTTA
GGTGCTGGTGCGAATCCTGAAATTGGTAAGAGAGCTGCAACTGAAGATAGAGCGAAAATCGAGCAACT
TTTAGAGGGTGCTGATATGGTTTTCATCACTGCTGGTATGGGTGGTGGTACAGGTACAGGTGGAGCTC
CTGTAGTTGCAGAAGTTGCAAAAGAGATGGGTATACTTACAGTAGCTGTAGTTACTAAGCCTTTCCCT
TTTGAAGGACCAAGAAGAATGAAAGCAGCAGAGCAAGGTATTGAGTTTTTATCTAAAAGTGTTGATTC
ACTGATTACTATTCCTAACGAAAAGTTACTGAAAGTACTTGGCCCTGGAACAAGCTTATTAGATGCCT
TTAAAGCAGCAAATAACGTGCTACTTGGCGCCGTTCAGGGTATTGCAGAATTAATTACTCGTCCTGGT
TTGATAAATGTCGATTTTGCTGATGTACGTACCGTTATGTCTGAGATGGGTACTGCCATGATGGGTTC
TGGTACTGCTTCTGGCGATGATAGAGCACAAGAAGCTGCTGATGCTGCTATTTCAAGTCCTTTATTAG
AGGATGTGGATTTAGCTGGTGCACGCGGGATCTTAGTTAATATTACCGCAGGTATGGATATTAGTATC
GATGAGTTTGAAACTGTTGGTAATGCCGTTAAAGCTTTCGCTTCTGAAAATGCGACTGTTGTTGTTGG
TGCTGTTATTGATATGGATATGACAGATGAGCTTCGTGTGACTGTTGTTGCTACGGGTATTGGCGCTG
AAAGTAAGCCTGATATTACGTTAGTAAATCCTATGCCAATGGCTGAAGCAAAAGTTGTCGGTGGGGAT
TATACACCAGCTGCACCACAGGCAAATTTAGCGACTGAAGCAATAGCTATGACTGATAGCAATGCGCA
GAAAGCAGCAGCAACCGACTTAGATACTTATTTAGATATTCCTGCTTTTTTACGTAAGCAAGCGGAT<u>T</u>
<u>AAtaaaaaccaaaattaag</u>

SEQ ID NO: 28

<u>MFDFNDSMVSNAIIKVVGVGGGGGNAVQHMCEEVSDVEFFALNTDGQALSKSKVQNILQIGTNLTKGL
GAGANPEIGKRAATEDRAKIEQLLEGADMVFITAGMGGGTGTGGAPVVAEVAKEMGILTVAVVTKPFP
FEGPRRMKAAEQGIEFLSKSVDSLITIPNEKLLKVLGPGTSLLDAFKAANNVLLGAVQGIAELITRPG</u>
LINVDFADVRTVMSEMGTAMMGSGTASGDDRAQEAADAAISSPLLEDVDLAGARGILVNITAGMDISI
DEFETVGNAVKAFASENATVVVGAVIDMDMTDELRVTVVATGIGAESKPDITLVNPMPMAEAKVVGGD
YTPAAPQANLATEAIAMTDSNAQKAAATDLDTYLDIPAFLRKQAD

VACCINES COMPRISING HEAT-SENSITIVE TRANSGENES

CROSS REFERENCE TO RELATED APPLICATIONS

This is the U.S. National Stage of International Application No. PCT/CA2010/001561, filed Oct. 7, 2010, which was published in English under PCT Article 21(2), which in turn claims the benefit of U.S. Provisional Application No. 61/249,385 filed Oct. 7, 2009, and U.S. Provisional Application No. 61/322,634 filed on Apr. 9, 2010, both herein incorporated by reference.

FIELD

The technology relates to genes derived from psychrophilic bacteria, for use in the development of heat-sensitive vaccines. In one example, the technology relates to recombinant pathogens harboring the heat-sensitive gene ligA from *Colwellia psychrerythraea*, *Pseudoalteromonas haloplanktis*, and *Shewanella frigidimarina* and to genes ligA, pyrG, hemC, ftsZ, cmk, murG, fmt, and dnaK from *C. psychrerythraea*.

BACKGROUND

Vaccines against bacterial and viral diseases have played an important role in reducing infectious diseases in humans; however, there is still a need for innovative vaccines to reduce the current global burden of infectious diseases. Cold-adapted viruses have been used for decades as vaccines against human viral diseases. The best known example of such a vaccine is the Sabin polio virus vaccine. An alternate example is a cold adapted influenza vaccine called FluMist® (Medimmune LLC, Gaithersburg, Md., USA), which was introduced in the U.S. in 2003. FluMist® has been shown to be considerably more effective in certain demographic groups than influenza vaccines that practice the more common vaccination strategy of using inactivated virus to stimulate an immune response. Typically cold-adapted or "temperature-sensitive" (TS) viral strains have been developed by passing the virus repeatedly in eggs or cell culture at low temperatures and then testing the progeny for their inability to grow above about 37° C., generally thought of as the "normal" human body temperature.

The concept of a "normal" human body temperature takes into consideration anatomical sites, individual variations, gender, physiological conditions and ambient temperature. Despite the number of variables, the human body can function only in a very narrow temperature range, which is generally about 36° C.-39° C. If the human body core temperature falls to about 35° C., the body must be warmed or death will ensue. The skin temperature is always cooler than the body core regardless of the ambient temperature and clothing worn. At moderate temperatures (e.g., 21° C.), the temperature of the skin is about 32° C.-35° C.

Those skilled in these arts are of the view that bacteria generally have a set of about 100 to 150 genes, called "essential genes" that are absolutely required for maintenance of bacterial viability. Identifying essential genes is difficult due to their nature, as knockouts of these genes results in death of the organism. Essential genes encode proteins composed of amino acid sequences that are highly conserved among almost all bacterial genera and species. This conservation presumably reflects their common function and structure among the different species. A select number of essential genes have been shown to be competent in substituting for a homologue in another bacterial species and in some cases these substitutions were from distantly related bacterial species. The conservation of amino acid sequences is widespread among bacteria, the deduced amino acid sequences of essential genes from psychrophiles and thermophiles shows high identity with their mesophilic counterparts. Microbiologists have generally used conditional lethal mutations, such as TS mutations, to identify essential genes.

Many bacterial species play significant roles in the global burden of infectious diseases. However, the causative agent of tuberculosis is probably the most significant contributor to human morbidity and mortality caused by an infectious bacterial disease. Although the Bacille Calmette-Guérin (BCG) vaccine has been used for several decades to protect against tuberculosis, its low efficacy has failed to lower the incidence of tuberculosis to acceptable levels.

SUMMARY

The present disclosure provides methods for engineering, producing and using heat-sensitive host microbial cells. In one example, recombinant pathogens contain heat-sensitive essential genes, for example inserted using homologous recombination. "Psychrophile" is a term that is applied to organisms that function optimally at cold temperatures e.g., <20° C. Bacteria that live in cold ocean water, especially the Arctic and Antarctic oceans, are examples of psychrophilic bacteria. Enzymes and other proteins in psychrophilic bacteria function better in the cold than their homologous counterparts in mesophilic bacteria. Many of the enzymes from psychrophilic bacteria are also prone to denaturation at temperatures much lower than those that would affect their mesophilic counterpart. Presumably the pattern of temperature-sensitivity of psychrophilic enzymes extends to the products of essential genes.

Methods of identifying and manipulating psychrophilic essential genes with desired TS properties are provided. in vitro and in vivo recombinant technologies can be used. *Francisella tularensis* is the etiologic agent of the zoonotic disease, tularaemia. It can infect numerous animals by a variety of routes, and typically infects and grows in monocyte-derived cells in organs of the reticuloendothelial system. A closely related bacterium, *Francisella novicida*, has many of the properties of *F. tularensis*, and, in addition, is highly amenable to many genetic manipulations, including gene substitutions. The pathophysiology and genetic properties of *F. novicida* make it ideal for studying the effects of gene substitutions on a pathogenic bacterium. *F. novicida* is a mesophile with a maximal growth temperature of about 45° C.

This disclosure also provides methods to determine maximal growth temperature of both bacterial strains and their growth properties at restrictive temperatures. The recombinant bacterial strains tested grew below the restrictive temperature but not above the restrictive temperature. When a psychrophilic essential allele encoding an essential gene is inserted into an area of a mammalian body that is colder than the human body core, e.g., the skin, the recombinant pathogenic bacteria will have the ability to thrive thereby inducing an immune response. When the pathogenic recombinant bacteria migrate to organs in the human body core where the temperature is higher, they die and are unable to harm the host.

The present disclosure provides isolated temperature-sensitive essential nucleic acid molecules from a psychrophilic bacterium comprising at least 80%, at least 90%, or at least 95% sequence identity to the nucleotide sequence shown in SEQ ID NO: 1, 3, 5, 7, 9, 11, 13, 15, 17, 19, 21, 22, 23, or 24. In some examples, the psychrophilic bacteria are operable at a temperature of about −10° C. to about 30° C., but inoperable at a temperature greater than about 30° C. Vectors and recombinant host cells (such as a recombinant bacterial host cell) that include such temperature-sensitive essential nucleic acid molecules from a psychrophilic bacterium are also provided. Immunogenic compositions that include such recombinant host bacteria (such as live or killed cells) are also disclosed. The disclosure also provides isolated proteins encoded by the disclosed isolated temperature-sensitive essential nucleic acid molecules, such as proteins having at least 80%, at least 90%, or at least 95% sequence identity to the amino acid sequence shown in SEQ ID NO: 2, 4, 6, 8, 10, 12, 14, 16, 18, 20, 22, 26, 27, or 28.

Methods of making a temperature-sensitive microbial host cell, such as a recombinant host cell, are provided. In one example the method includes introducing (for example by inserting, substituting or replacing) a nucleic acid construct into the genome of a mesophilic bacterial strain, wherein the nucleic acid construct includes a temperature-sensitive essential nucleic acid molecule from a psychrophilic bacterial strain and one or more control sequences operably linked to the temperature-sensitive essential nucleic acid molecule, wherein the temperature-sensitive essential peptide encoded by the introduced temperature-sensitive essential nucleic acid molecule is operable (e.g., functional) at a temperature less than about 30° C. and inoperable (e.g., non-functional) at a temperature greater than about 30° C. In some examples the method also includes culturing the temperature-sensitive microbial host cell at a temperature wherein the temperature-sensitive peptide is operable, whereby said microbial host cell produces a plurality of peptides; increasing the culturing temperature to a temperature at which the temperature-sensitive peptide is inoperable; maintaining said culturing for a period of time sufficient to kill the temperature-sensitive microbial host cell; and harvesting the killed temperature-sensitive microbial host cells.

Methods for producing an immune response to a bacterium in a subject using the disclosed nucleic acid molecules, proteins, and recombinant host cells are provided. In one example the method includes administering to the subject a therapeutically effective amount of a temperature-sensitive bacterium, wherein the temperature-sensitive bacterium expresses a temperature-sensitive essential nucleic acid molecule from a psychrophilic bacterial strain, thereby inducing an immune response to the bacterium. Such methods can be used to prevent or treat a bacterial infection (such as a *M. tuberculosis, Salmonella* or *Francisella* infection).

The foregoing and other features of the disclosure will become more apparent from the following detailed description of a several embodiments which proceeds with reference to the accompanying figures.

BRIEF DESCRIPTION OF THE DRAWINGS

Figure 1:
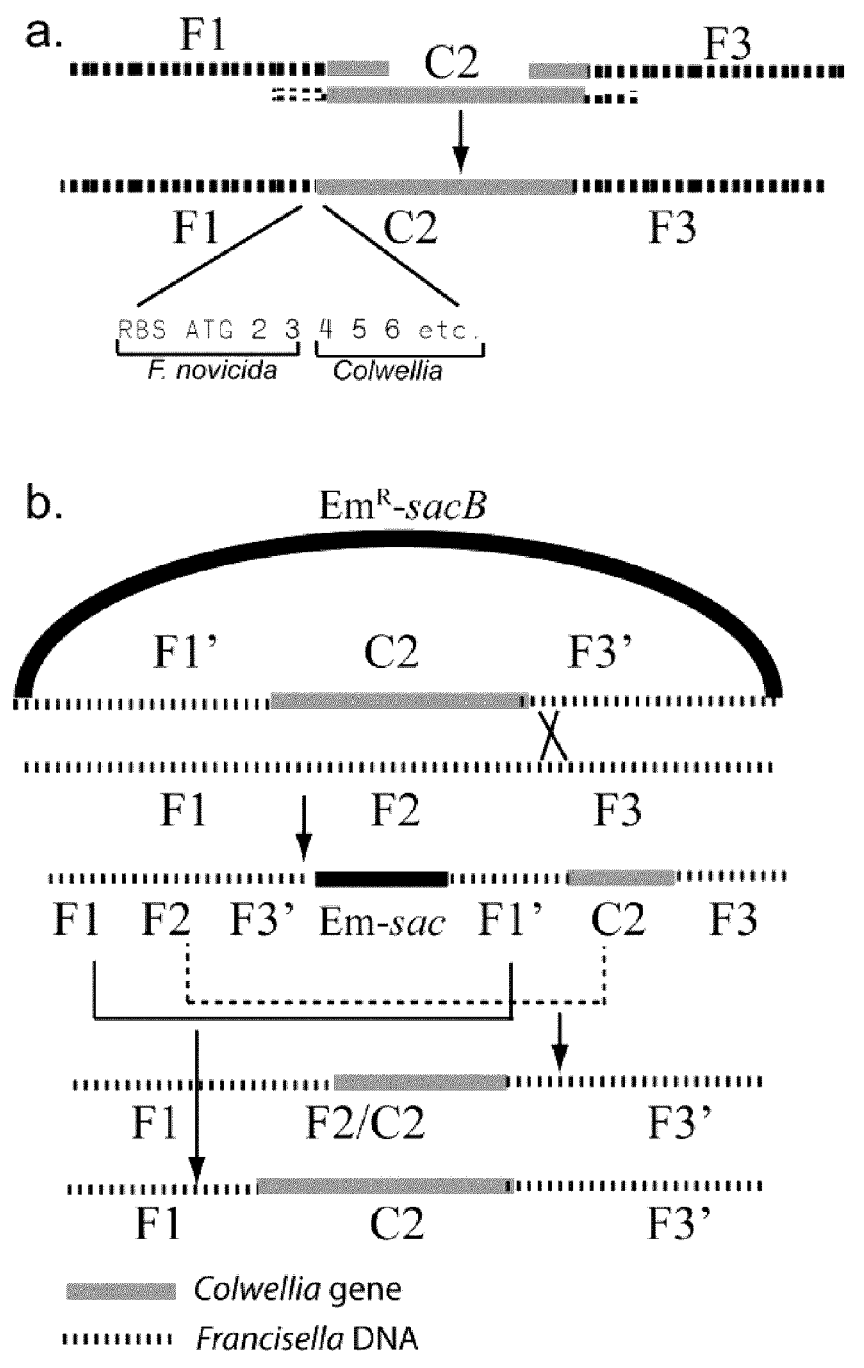

FIG. 1a is a flowchart illustrating an exemplary method using polymerase chain reaction (PCR), FIG. 1b is a schematic chart illustrating an exemplary method showing DNA integration-excision events that result in a gene substitution.

FIG. 6a is a graph illustrating the growth curve of wt *F. novicida* and *F. novicida* with the *P. haloplanktis* ligA$_{Ph2}$ gene substituted for the *F. novicida* homologue at 21° C., FIG. 6b is a graph illustrating the growth curve of *F. novicida* with the *P. haloplanktis* ligA$_{Ph2}$ gene substituted for the *F. novicida* homologue and wt *F. novicida* with a temperature shift from 21° C. to 26° C. after 2 hours, FIG. 6c is a graph illustrating the growth curve of *F. novicida* with the *P. haloplanktis* ligA$_{Ph2}$ gene substituted for the *F. novicida* homologue and wt *F. novicida* with a temperature shift from 21° C. to 28° C. after 2 hours, FIG. 6d is a graph illustrating the growth curve of *F. novicida* with the *P. haloplanktis* ligA$_{Ph2}$ gene substituted for the *F. novicida* homologue and wt *F. novicida* with a temperature shift from 21° C. to 30° C. after 2 hours.

FIGS. 11A-11L show sequences disclosed herein, with underlined portions being *F. novicida* sequence.

SEQUENCE LISTING

Figure 2:
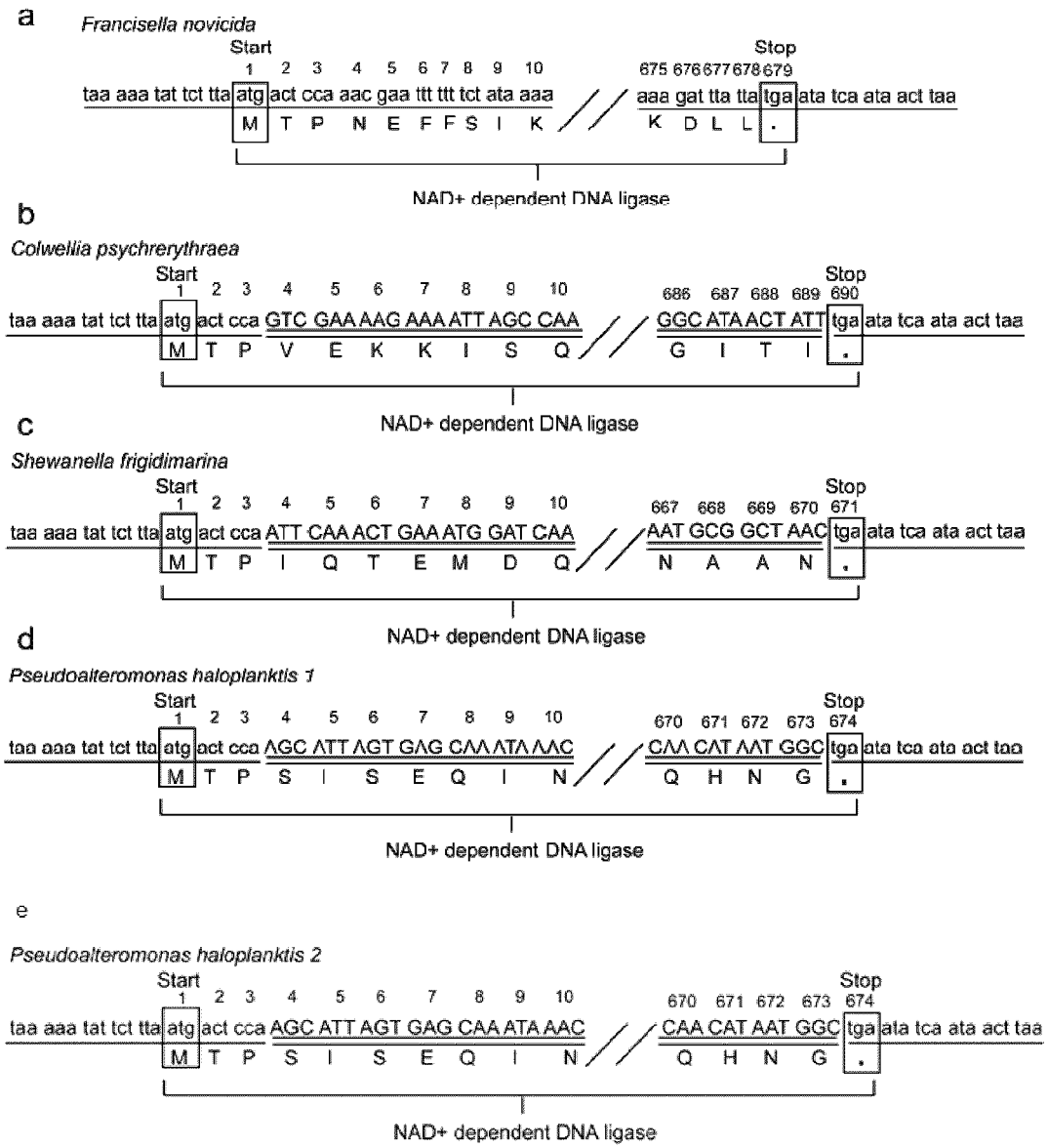
FIG. 2a is a schematic illustrating the sequence of the wild type (wt) *F. novicida* ligA gene as it exists normally in a chromosome.
FIG. 2b is a schematic illustrating ligA$_{Cp}$ gene substitutions into the *F. novicida* chromosome according to an exemplary method of the present disclosure.
FIG. 2c is a schematic illustrating ligA$_{Sf}$ gene substitution into the *F. novi-cida* chromosome according to an exemplary method of the present disclosure.
FIG. 2d is a schematic illustrating ligA$_{Ph}$ gene substitutions into the *F. novicida* chromosome according to an exemplary method of the present disclosure.
FIG. 2e is a schematic illustrating ligA$_{Ph2}$ gene substitutions into the *F. novicida* chromosome according to an exemplary method of the present disclosure.
Figure 3:
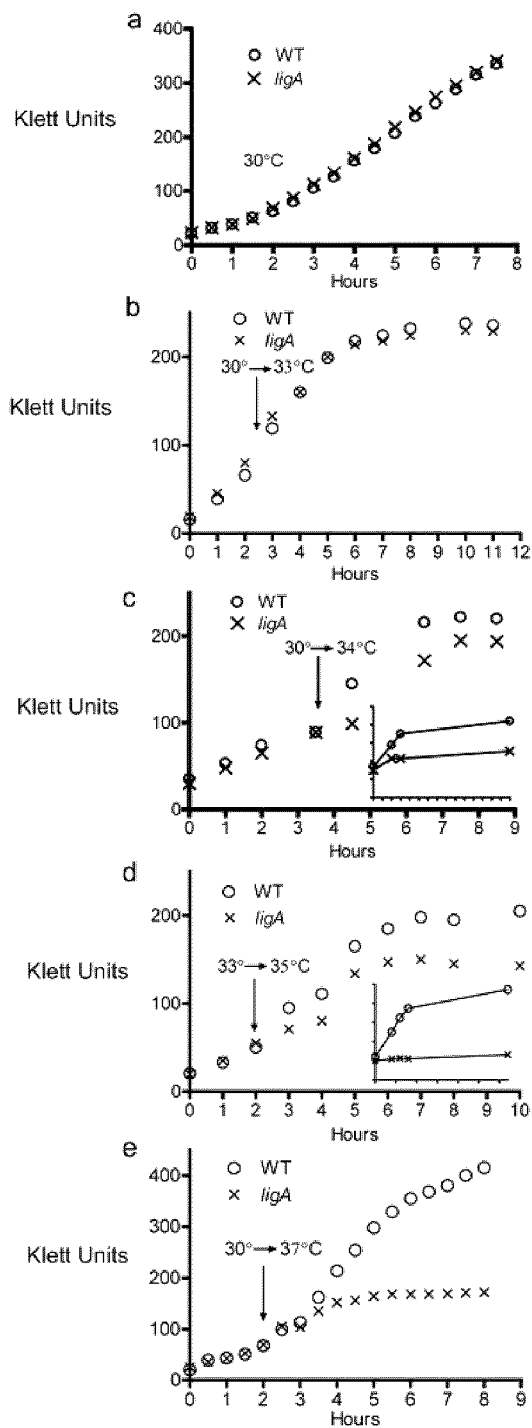
FIG. 3a is a graph illustrating the growth curve of wt *F. novicida* and *F. novicida* with the *C. psychrerythraea* ligA$_{Cp}$ gene substituted for the *F. novicida* homologue at 30° C.
FIG. 3b is a graph illustrating the growth curve of *F. novicida* with the *C. psychrerythraea* ligA$_{Cp}$ gene substituted for the *F. novicida* homologue and wt *F. novicida* with a temperature shift from 30° C. to 33° C. after 2 hours.
FIG. 3c is a graph illustrating the growth curve of *F. novicida* with the *C. psychrerythraea* ligA$_{Cp}$ gene substituted for the *F. novicida* homologue and wt *F. novicida* with a temperature shift from 30° C. to 34° C. after 3.5 hours.
FIG. 3d is a graph illustrating the growth curve of *F. novicida* with the *C. psychrerythraea* ligA$_{Cp}$ gene substituted for the *F. novicida* homologue and wt *F. novicida* with a temperature shift from 30° C. to 35° C. after 2 hours.
FIG. 3e is a graph illustrating the growth curve of *F. novicida* with the *C. psychrerythraea* ligA$_{Cp}$ gene substituted for the *F. novicida* homologue and wt *F. novicida* with a temperature shift from 30° C. to 37° C. after 2 hours.
Figure 4:
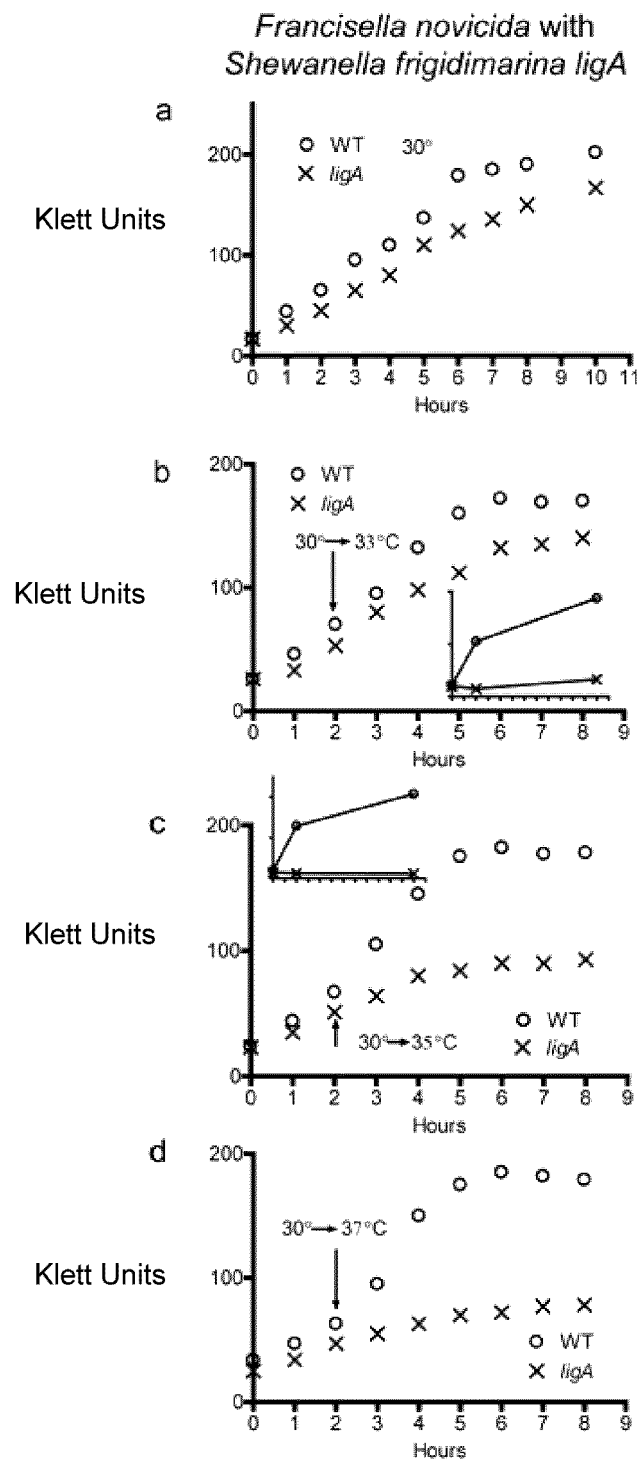
FIG. 4a is a graph illustrating the growth curve of wt *F. novicida* and *F. novicida* with the *S. frigidimarina* ligA$_{Sf}$ gene substituted for the *F. novicida* homologue at 30° C.
FIG. 4b is a graph illustrating the growth curve of *F. novicida* with the *S. frigidimarina* ligA$_{Sf}$ gene substituted for the *F. novicida* homologue and wt *F. novicida* with a temperature shift from 30° C. to 33° C. after 2 hours.
FIG. 4c is a graph illustrating the growth curve of *F. novicida* with the *S. frigidimarina* ligA$_{Sf}$ gene substituted for the *F. novicida* homologue and wt *F. novicida* with a temperature shift from 30° C. to 35° C. after 2 hours.
FIG. 4d is a graph illustrating the growth curve of *F. novicida* with the *S. frigidimarina* ligA$_{Sf}$ gene substituted for the *F. novicida* homologue and wt *F. novicida* with a temperature shift from 30° C. to 37° C. after 2 hours.
Figure 5:
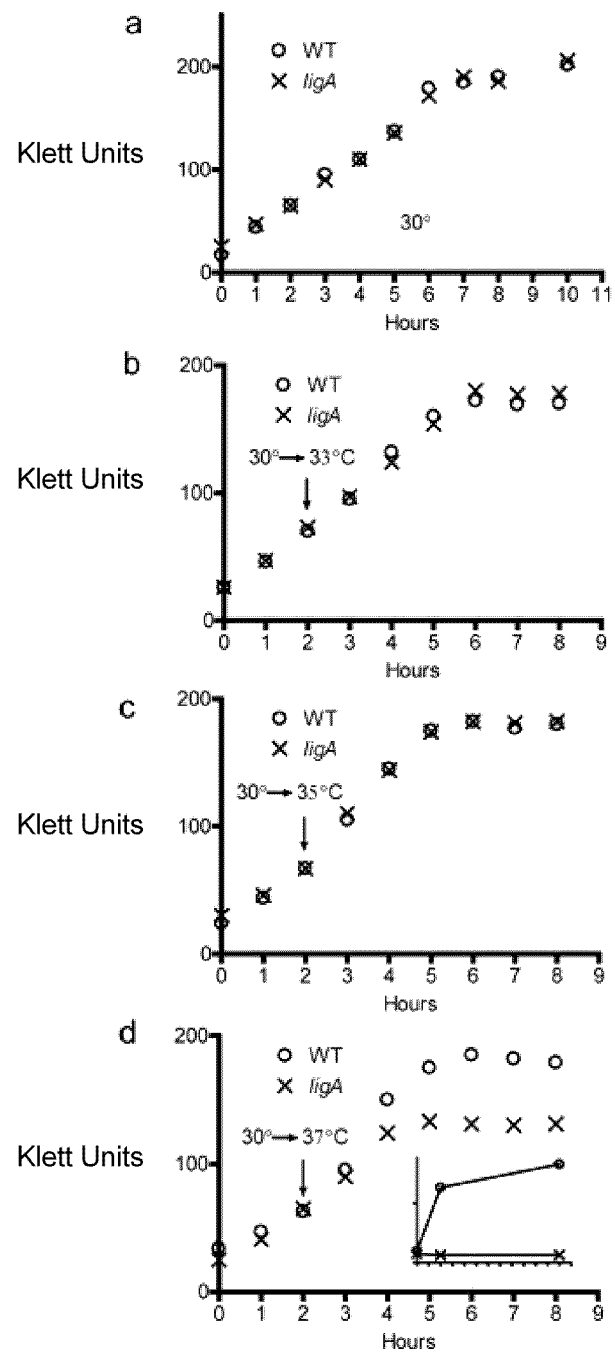
FIG. 5a is a graph illustrating the growth curve of wt *F. novicida* and *F. novicida* with the *P. haloplanktis* ligA$_{Ph}$ gene substituted for the *F. novicida* homologue at 30° C.
FIG. 5b is a graph illustrating the growth curve of *F. novicida* with the *P. haloplanktis* ligA$_{Ph}$ gene substituted for the *F. novicida* homologue and wt *F. novicida* with a temperature shift from 30° C. to 33° C. after 2 hours.
FIG. 5c is a graph illustrating the growth curve of *F. novicida* with the *P. haloplanktis* ligA$_{Ph}$ gene substituted for the *F. novicida* homologue and wt *F. novicida* with a temperature shift from 30° C. to 35° C. after 2 hours.
FIG. 5d is a graph illustrating the growth curve of *F. novicida* with the *P. haloplanktis* ligA$_{Ph}$ gene substituted for the *F. novicida* homologue and wt *F. novicida* with a temperature shift from 30° C. to 37° C. after 2 hours.
Figure 7:
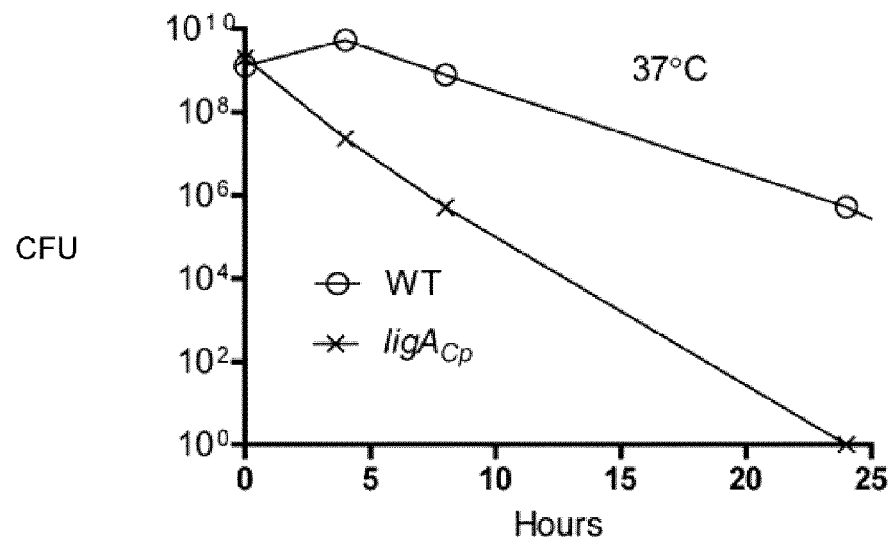
FIG. 7 is a graph illustrating the decline in viability of wt *F. novicida* and *F. novicida*-ligA$_{Cp}$ cultures at 37° C. after being grown to late exponential phase at 33° C.

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood to be included by any reference to the displayed strand.

SEQ ID NO: 1 is a full length nucleic acid coding sequence of the ligA$_{Cp}$ hybrid gene.

SEQ ID NO: 2 is the deduced 689 amino acid sequence of LigA$_{Cp}$ hybrid protein.

SEQ ID NO: 3 is a full length nucleic acid coding sequence of the ligA$_{Ph}$ hybrid gene.

SEQ ID NO: 4 is the deduced 673 amino acid sequence of LigA$_{Ph}$ hybrid protein.

SEQ ID NO: 5 is a full length nucleic acid coding sequence of the ligA$_{Ph2}$ hybrid gene.

SEQ ID NO: 6 is the deduced 673 amino acid sequence of LigA$_{Ph2}$ hybrid protein.

SEQ ID NO: 7 is a full length nucleic acid coding sequence of the ligA$_{Sf}$ hybrid gene.

SEQ ID NO: 8 is the deduced 670 amino acid sequence of LigA$_{Sf}$ hybrid protein.

SEQ ID NO: 9 is a full length nucleic acid coding sequence of the pyrG$_{Cp}$ hybrid gene.

SEQ ID NO: 10 is the deduced 545 amino acid sequence of PyrG$_{Cp}$ hybrid protein.

SEQ ID NO: 11 is a full length nucleic acid coding sequence of the hemC$_{Cp}$ hybrid gene.

SEQ ID NO: 12 is the deduced 317 amino acid sequence of HemC$_{Cp}$ hybrid protein.

SEQ ID NO: 13 is a full length nucleic acid coding sequence of the fmt$_{Cp}$ hybrid gene.

SEQ ID NO: 14 is the deduced 327 amino acid sequence of Fmt$_{Cp}$ hybrid protein.

SEQ ID NO: 15 is a full length nucleic acid coding sequence of the murG$_{Cp}$ hybrid gene.

SEQ ID NO: 16 is the deduced 387 amino acid sequence of MurG$_{Cp}$ hybrid protein.

SEQ ID NO: 17 is a full length nucleic acid coding sequence of codon optimized ligA$_{Cp}$ optimized for *M. tuberculosis*.

SEQ ID NO: 18 is the deduced 689 amino acid coding sequence of codon optimized LigA$_{Cp}$ hybrid protein with the first four codons changed to the *M. tuberculosis* form.

SEQ ID NO: 19 is a full length nucleic acid coding sequence of the dnaK$_{Cp}$ hybrid gene.

SEQ ID NO: 20 is the deduced 638 amino acid coding sequence of DnaK$_{Cp}$ hybrid protein.

SEQ ID NOS: 21 and 22 are a full length nucleic acid coding sequence of the essential gene tyrS from *Colwellia psychrerythraea*, and the corresponding amino acid sequence, respectively.

SEQ ID NO: 23 and 24 are a full length nucleic acid coding sequence of the essential gene cmk from *Colwellia psychrerythraea* and the corresponding amino acid sequence, respectively. As shown in FIG. 11J, *F. novicida* sequence is underlined. The underlined regions correspond to the *F. novicida* sequence in both the nucleotide and amino acid sequence. The "non-underlined" is *Colwellia psychrerythraea* sequence. In the amino acid sequence there is no underlined amino acids at the end since the *F. novicida* sequence starts at the stop codon.

SEQ ID NO: 25 and 26 are a full length nucleic acid coding sequence of the essential gene dnaKsf from *Shewanella frigidimarina* and the corresponding amino acid sequence, respectively. As shown in FIG. 11K, *Francisella novicida* sequence is underlined. The underlined regions correspond to the *F. novicida* sequence in both the nucleotide and amino acid sequence. The "non-underlined" shows the *Shewanella frigidimarina* sequence. In the amino acid sequence at the beginning (MGK) is identical between *Shewanella* and *Francisella*, so it is double underlined. The single underline at the end of the amino sequence corresponds to the *F. novicida* sequence.

SEQ ID NO: 27 and 28 are a full length nucleic acid coding sequence of the essential geneftsZ from *Colwellia psychrerythraea* and the corresponding amino acid sequence, respectively. As shown in FIG. 11L, *Francisella novicida* sequence is underlined. The underlined regions correspond to the *F. novicida* sequence in both the nucleotide and amino acid sequence. The "non-underlined" regions are *Colwellia psychrerythraea* sequence. There is extensive *F. novicida* region at the 5'-end (N-terminus).

DETAILED DESCRIPTION

The following explanations of terms and methods are provided to better describe the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which a disclosed invention pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short*

*Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

The references cited herein are incorporated by reference.

In order to facilitate review of the various embodiments of the disclosure, the following explanations of specific terms are provided. Unless otherwise noted, technical terms are used according to conventional usage by those skilled in the arts Adjuvant:

A vehicle used to enhance antigenicity, for example antigenicity of a recombinant host bacterium containing a TS essential psychrophilic bacteria sequence disclosed herein. Adjuvants include a suspension of minerals (e.g., alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants (for example see U.S. Pat. No. 6,194,388; U.S. Pat. No. 6,207,646; U.S. Pat. No. 6,214,806; U.S. Pat. No. 6,218,371; U.S. Pat. No. 6,239,116; U.S. Pat. No. 6,339,068; U.S. Pat. No. 6,406,705; and U.S. Pat. No. 6,429,199). Adjuvants include biological molecules (a "biological adjuvant"), such as costimulatory molecules. Exemplary adjuvants include IL-2, RANTES, GM-CSF, TNF-$\alpha$, IFN-$\gamma$, G-CSF, LFA-3, CD72, B7-1, B7-2, OX-40L and 41 BBL.

Administration:

The introduction of a composition (such as an immunogenic composition) into a subject (such as a mammal, for example a human) by a selected route. Exemplary routes of administration include, but are not limited to, topical, injection (such as subcutaneous, intramuscular, intradermal, intraperitoneal, intratumoral, and intravenous), oral, sublingual, rectal, transdermal, intranasal, vaginal and inhalation routes.

Ameliorate:

The improvement of a disease or pathological condition (such as a bacterial infection) with respect to the effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known to those skilled in the arts specific to the particular disease.

Animal:

Living multi-cellular vertebrate organisms, a category that includes mammals and birds. The term "mammal" includes both human and non-human mammals. Similarly, the term "subject" includes both human and veterinary subjects (such as mice, rats, rabbits, dogs, cats, horses, and cattle).

Antibody:

A polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains.

Typically, a naturally occurring immunoglobulin has heavy (H) chains and light (L) chains interconnected by disulfide bonds. There are two types of light chain, lambda ($\lambda$) and kappa (k). There are five main heavy chain classes (or isotypes) which determine the functional activity of an antibody molecule: IgM, IgD, IgG, IgA and IgE.

"Specifically binds" refers to the ability of individual antibodies to specifically immunoreact with an antigen, such as a bacterial antigen, relative to binding to unrelated proteins, such as non-bacterial proteins. The binding is a non-random binding reaction between an antibody molecule and an antigenic determinant of the T cell surface molecule. The desired binding specificity is typically determined from the reference point of the ability of the antibody to differentially bind the T cell surface molecule and an unrelated antigen, and therefore distinguish between two different antigens, particularly where the two antigens have unique epitopes. An antibody that specifically binds to a particular epitope is referred to as a "specific antibody".

In some examples, an antibody specifically binds to a target (such as a bacterial protein) with a binding constant that is at least $10^3$ $M^{-1}$ greater, $10^4 M^{-1}$ greater or $10^5$ $M^{-1}$ greater than a binding constant for other molecules in a sample or subject. In some examples, an antibody or fragments thereof, has an equilibrium constant (Kd) of 1 nM or less. For example, an antibody binds to a target, such as a bacterial protein with a binding affinity of at least about $0.1 \times 10^{-8}$ M, at least about $0.3 \times 10^{-8}$ M, at least about $0.5 \times 10^{-8}$ M, at least about $0.75 \times 10^{-8}$ M, at least about $1.0 \times 10^{-8}$ M, at least about $1.3 \times 10^{-8}$ M at least about $1.5 \times 10^{-8}$ M, or at least about $2.0 \times 10^{-8}$ M. Kd values can, for example, be determined by competitive ELISA (enzyme-linked immunosorbent assay) or using a surface-plasmon resonance device such as the Biacore T100, which is available from Biacore, Inc., Piscataway, N.J.

Antigen:

A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Generally, T cells recognize epitopes of continuous amino acids. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance.

Examples of antigens include, but are not limited to, peptides, lipids, polysaccharides, and nucleic acids containing antigenic determinants, such as those recognized by an immune cell. An antigen can be a tissue-specific antigen, or a disease-specific antigen. These terms are not exclusive, as a tissue-specific antigen can also be a disease specific antigen. A tissue-specific antigen is expressed in a limited number of tissues, such as a single tissue. A tissue specific antigen may be expressed by more than one related type of tissue, such as alveolar and bronchial tissue. A disease-specific antigen is expressed coincidentally with a disease process. Specific non-limiting examples of a disease-specific antigen are an antigen whose expression correlates with, or is predictive of, a bacterial infection, such as tuberculosis. A disease-specific antigen can be an antigen recognized by T cells or B cells.

CD4:

Cluster of differentiation factor 4, a T cell surface protein that mediates interaction with the MHC Class II molecule. CD4 also serves as the primary receptor site for HIV on T cells during HIV infection. Cells that express CD4 are often helper T cells.

CD8:

Cluster of differentiation factor 8, a T cell surface protein that mediates interaction with the MHC Class I molecule. Cells that express CD8 are often cytotoxic T cells. "CD8+ T cell mediated immunity" is an immune response implemented by presentation of antigens to CD8+ T cells.

Contacting:

The process of incubating one agent in the presence of another. Thus, when a cell is contacted with an agent (such as an immunogenic composition), the cell is incubated with the agent for a sufficient period of time for the agent and the cell to interact.

Cool Parts of the Body:

Regions of a human or other mammalian body that generally have a lower temperature than other parts of the body. The concept of natural human (or other mammal) body temperature variation due to anatomical sites, gender, physiological and ambient temperature. Despite the number of variables, the human (or other mammalian) body can function only in a very narrow temperature range, hence, for example the human body core remains at about 36° C.-39° C. Cool parts of the body include skin, mouth and rectum. Skin temperature, for example, is about 32° C.-35° C. Thus, in some examples, cool parts of the body have temperatures that are at least 1° C. less, at least 2° C. less, at least 3° C. less, at least 4° C. less, at least 4° C. less, or at least 6° C. less, such as 1° C. to 8° C. less, 1° C. to 6° C. less, 2° C. to 6° C. less, or 2° C. to 4° C. less, than other parts of the body, such as the core.

Cytokine:

Proteins made by cells that affect the behavior of other cells, such as lymphocytes. In one embodiment, a cytokine is a chemokine, a molecule that affects cellular trafficking. Specific, non-limiting examples of cytokines include the interleukins (IL-2, IL-4, IL-6, IL-10, IL-21, etc.), and IFN-γ.

Degenerate Variant:

A TS essential psychrophilic bacteria nucleic acid sequence that encodes a TS essential psychrophilic bacteria protein that includes a nucleic acid sequence that is degenerate as a result of the genetic code. There are 20 natural amino acids, most of which are specified by more than one codon. Therefore, all degenerate nucleotide sequences are included in this disclosure as long as the amino acid sequence of the TS essential psychrophilic bacteria peptide encoded by the nucleotide sequence is unchanged.

$Em^R$:

Erythromycin resistance.

Essential Gene:

A gene that is necessary for the growth of the organism (such as a mesophilic bacterium) under all culturing conditions.

Expression Control Sequences:

Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences. In one embodiment, the promoter is a cytomegalovirus promoter.

Heat-Sensitive:

An inability to perform an essential biological function at temperatures above about 28° C. Similarly, the term "heat-sensitive protein or polypeptide" refers to a non-functional mature protein resulting from heat-induced deactivation. An enzyme that does not catalyze its known reaction efficiently enough to support growth, development or life of the organism above about 28° C. is an example of such a protein.

Heat-Sensitive Allele:

An allele comprising a gene encoding a heat-sensitive protein. Similarly the term, "heat-sensitive gene" refers to a gene encoding a heat-sensitive protein.

Host Cells:

Cells into which a heterologous nucleic acid molecule has been introduced. For example, such cells may include a nucleic acid vector that is propagated and its DNA expressed. The cell may be prokaryotic or eukaryotic. The cell can be prokaryotic, such as a bacterial cell. The term also includes any progeny of the subject host cell. It is understood that all progeny may not be identical to the parental cell since there may be mutations that occur during replication. However, such progeny are included when the term "host cell" is used.

Immune Response:

A response of a cell of the immune system, such as a B cell, T cell, or monocyte, to a stimulus. In one embodiment, the response is specific for a particular antigen or a particular TS recombinant microbial cell, such as mesophilic bacteria containing a psychrophile essential nucleic acid molecule provided herein. In one embodiment, an immune response is a T cell response, such as a CD4+ response or a CD8+ response. In another embodiment, the response is a B cell response, and results in the production of specific antibodies. The development of an immune response following administration of mesophilic bacteria containing a psychrophile TS essential nucleic acid molecule can be measured using routine methods known in the art, for example by measuring cytokine production as an indication of a protective immune response.

Immunogenic Composition:

Compositions that include recombinant mesophilic bacteria containing a psychrophile TS essential nucleic acid molecule that induces a measurable CTL response against a recombinant mesophilic bacteria protein, or induces a measurable B cell response (such as production of antibodies that specifically bind a recombinant mesophilic bacteria-specific protein) against a recombinant mesophilic bacteria protein. For example, the immunogenic polypeptide or a nucleic acid encoding the immunogenic polypeptide can be present in a heat-sensitive mesophilic bacteria generated using the methods provided herein, wherein the bacteria is art of an immunogenic composition that can further include pharmaceutically acceptable carriers, and/or other therapeutic agents. An immunogenic composition can optionally include an adjuvant, a PD-1 antagonist, a co-stimulatory molecule, or a nucleic acid encoding a costimulatory molecule. An immunogenic composition can be readily tested for its ability to induce a CTL by art-recognized assays.

Immunogenic Peptide:

A peptide which comprises an allele-specific motif or other sequence such that the peptide will bind an MHC molecule and induce a cytotoxic T lymphocyte ("CTL") response, or a B cell response (e.g. antibody production) against the antigen from which the immunogenic peptide is derived. Immunogenic peptides can also be identified by measuring their binding to a specific MHC protein and by their ability to stimulate CD4 and/or CD8 when presented in the context of the MHC protein.

Generally, immunogenic polypeptides can be used to induce an immune response in a subject, such as a B cell response or a T cell response. In one example, an immunogenic polypeptide, when bound to a MHC Class I molecule, activates cytotoxic T lymphocytes (CTLs) against the polypeptide. Induction of CTLs using synthetic peptides and CTL cytotoxicity assays are known in the art, see U.S. Pat. No. 5,662,907. In one example, an immunogenic peptide includes an allele-specific motif or other sequence such that the peptide will bind an MHC molecule and induce a cytotoxic T lymphocyte ("CTL") response against the antigen from which the immunogenic peptide is derived.

Immunologically Reactive Conditions:

Conditions that allow an antibody specific for a particular epitope to bind to that epitope to a greater degree than, and/or to the substantial exclusion of, binding to substantially all other epitopes. These conditions are dependent upon the format of the antibody binding reaction and typically are those utilized in immunoassay protocols or those conditions encountered in vivo. The immunologically reactive conditions employed in the disclosed methods are "physiological conditions" which include reference to conditions (e.g., temperature, osmolarity, pH) that are typical inside a living mammal or a mammalian cell. While it is recognized that some organs are subject to extreme conditions, the intra-organ and intracellular environment is generally about pH 7 (e.g., from pH 6.0 to pH 8.0, or pH 6.5 to pH 7.5, such as pH 7.2), contains water as the predominant solvent, and exists at a temperature above 0° C. and below 50° C. Osmolarity is within the range that is supportive of cell viability and proliferation. These conditions are well known to those skilled in these arts.

Interferon Gamma (IFN-γ):

IFN-γ is a dimeric protein with subunits of 146 amino acids. The protein is glycosylated at two sites, and the pI is 8.3-8.5. IFN-γ is synthesized as a precursor protein of 166 amino acids including a secretory signal sequence of 23 amino acids. Two molecular forms of the biologically active protein of 20 and 25 kDa have been described. Both of them are glycosylated at position 25. The 25 kDa form is also glycosylated at position 97. The observed differences of natural IFN-γ with respect to molecular mass and charge are due to variable glycosylation patterns. 40-60 kDa forms observed under non-denaturing conditions are dimers and tetramers of IFN-γ. The human gene has a length of approximately 6 kb. It contains four exons and maps to chromosome 12q24.1.

IFN-γ can be detected by sensitive immunoassays, such as an ELISPOT test that allows detection of individual cells producing IFN-γ. Minute amounts of IFN-γ can be detected indirectly by measuring IFN-induced proteins such as Mx protein. The induction of the synthesis of IP-10 has been used also to measure IFN-γ concentrations. In addition, bioassays can be used to detect IFN-γ, such as an assay that employs induction of indoleamine 2,3-dioxygenase activity in 2D9 cells. The production of IFN-γ can be used to assess T cell activation, such as activation of a T cell by bacterial antigen.

Isolated:

A biological component (such as a nucleic acid molecule, protein or organelle) that has been substantially separated or purified away from other biological components in the cell of the organism in which the component naturally occurs, e.g., other chromosomal and extra-chromosomal DNA and RNA, proteins and organelles. Nucleic acid molecules and proteins that have been "isolated" include nucleic acid molecules and proteins purified by standard purification methods. In another embodiment, "isolated" refers to nucleic acid molecules and proteins prepared by recombinant expression in a host cell as well as chemically synthesized nucleic acids.

ligA:

A wt allele of the gene encoding NAD-dependent DNA ligase found in mesophilic bacteria such as F. novicida, M. smegmatis or E. coli. Furthermore, ligA with a subscript, such as $ligA_{Cp}$, $ligA_{Sf}$ or $ligA_{Ph}$, refers to a wt allele of the gene encoding NAD-dependent DNA ligase found in psychrophilic bacteria. For example $ligA_{Cp}$ refers to the wt allele of ligA found in the Arctic bacterium C. psychrerythraea strain 34H which has a maximal growth temperature below 18° C. The ligA sequences from psychrophilic bacteria can be introduced into mesophilic bacteria, to confer temperature sensitivity to the mesophilic bacteria.

Mesophile:

An organism naturally found in environments at temperatures between about 20° C. and 50° C. A bacterial mesophile refers to a bacterium that is normally associated with a mammal and thus is normally functioning at temperatures between about 32° C. and 45° C.

Psychrophile:

An organism naturally found in environments that are permanently below 20° C., often permanently below 10° C. and sometimes below 0° C. Such permanently cold environments include most ocean environments, permafrost soils, Arctic and Antarctic environments. Those skilled in these arts will understand that "psychrophile" and "psychrotroph" are commonly used to describe bacteria that grow in cold environments.

Psychrophilic:

Features found in psychrophiles. For example, a "psychrophilic enzyme" is an enzyme isolated from a psychrophile.

Peptide Modifications:

Analogs (non-peptide organic molecules), derivatives (chemically functionalized peptide molecules obtained starting with the disclosed peptide sequences) and variants (homologs) of proteins that can be used in the methods and compositions provided herein. Peptides are comprised of amino acids, which may be either L- and/or D-amino acids, naturally occurring and otherwise. The peptides can be modified by a variety of chemical techniques to produce derivatives having essentially the same activity as the unmodified peptides, and optionally having other desirable properties. Modifications are well known to those skilled in these arts.

Pharmaceutically Acceptable Carriers:

The pharmaceutically acceptable carriers (vehicles) useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of one or more therapeutic composition, such as an immunogenic composition.

The disclosed purified active compositions can be administered alone or combined with an acceptable carrier. Preparations can contain one type of therapeutic molecule, or can be composed of a combination of several types of therapeutic molecules. The nature of the carrier will depend on the particular mode of administration being utilized.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing or Treating a Disease:

"Preventing" a disease refers to inhibiting the full development of a disease, for example in a person who is known to be at risk of infection with *M. tuberculosis*, or *M. leprae*. An example of a person with a known predisposition is someone living with a person diagnosed with tuberculosis, health care professionals, or someone otherwise known to have been exposed to *M. tuberculosis*. "Treatment" refers to a therapeutic intervention that ameliorates a sign or symptom of a disease or pathological condition, such as tuberculosis, after it has begun to develop.

Purified:

The term purified does not require absolute purity; rather, it is intended as a relative term. Thus, for example, a purified protein preparation is one in which the protein is more pure than the protein in its originating environment within a cell. A preparation of a protein is typically purified such that the protein represents at least 50% of the total protein content of the preparation. However, more highly purified preparations may be required for certain applications. For example, for such applications, preparations in which the protein includes at least 75% or at least 90% of the total protein content may be employed.

Recombinant:

A nucleic acid molecule that has a sequence not naturally occurring or a sequence that is made by an artificial combination of two naturally separated segments of sequence. This artificial combination is often accomplished by chemical synthesis or by the artificial manipulation of isolated segments of nucleic acids, by genetic engineering techniques, for example. Also refers to cells into which a non-native nucleic acid molecule has been introduced.

Resistant to Infection:

Animals (e.g., mammals) that demonstrate decreased symptoms of infection compared to non-resistant animals. Evidence of resistance to infection can appear as, for example, lower rates of mortality, increased life spans measured after exposure to the infective agent, fewer or less intense physiological symptoms, such as fewer lesions, or decreased cellular or tissue concentrations of the infective agent. In one embodiment, resistance to infection is demonstrated by a heightened immune response.

Restrictive Temperature:

The lowest temperature at which an organism is unable to grow. For example, in Table 1 "restrictive temperature" specifically refers to the lowest temperature at which the *F. novicida* strain with a psychrophilic gene integrated is unable to form an isolated colony on agar media. Due to the variation in the temperature of incubators, these temperatures are interpreted as being about ±1° C.

sacB Cassette:

A modular DNA sequence encoding the enzyme levansucrase from *Bacillus subtilus*. Expression of this gene is lethal in the presence of sucrose to many bacteria and can thus be used as a counter-selection agent to help select for the loss of gene sequences.

Selective Hybridization:

Hybridization under moderately or highly stringent conditions that exclude non-related nucleotide sequences, the techniques of hybridization are known to those skilled in these arts.

Sequence Identity:

The identity/similarity between two or more nucleic acid sequences, or two or more amino acid sequences, expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 15-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 30% sequence identity or more counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity with a protein disclosed herein. Thus in one example, a protein that can be used in the disclosed methods and compositions has at least 60%, at least 70%, at least 80%, at least 90%, at least 95%, at least 98%, or at least 99% sequence identity to SEQ ID NO: 2, 4, 6, 8, 10, 12, 14, 16, 18, 20, 22, 24, 26 and 28 and retains the ability to confer TS (such as heat-sensitivity) to a mesophilic bacteria.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least about 60%, 70%, 80%, 90%, 95%, 98%, or 99% sequence identity with a disclosed nucleic acid sequence as determined by this method. Thus in one example, a nucleic acid sequence that can be used in disclosed methods and compositions has at least 60%, at least 70%, at least 80%, at least 90%, at least 95%, at least 98%, or at least 99% sequence identity to SEQ ID NO: 1, 3, 5, 7, 9, 11, 13, 15, 17, 19, 21, 23, 25, and 27 and retains the ability to encode a protein that can confer TS (such as heat-sensitivity) to a mesophilic bacteria. An alternative (and not necessarily cumulative) indication that two nucleic acid sequences are substantially identical is that the peptide which the first nucleic acid encodes is immunologically cross reactive with the peptide encoded by the second nucleic acid.

Temperature-Sensitive (TS)" or "Heat-Sensitive (HS):
A bacterial component (such as a protein) or bacterium that is active up to about 30° C. and inactivated at a temperature that is normally found in the human body, e.g., above about 30° C.

Tester Strain:
A mesophilic bacterium that is amenable to gene replacement allowing the substitution of a psychrophilic essential gene for the homologue naturally found in the tester strain.

Therapeutically Effective Amount:
An amount of a composition that alone, or together with an additional therapeutic agent(s) sufficient to achieve a desired effect in a subject, or in a cell, being treated with the agent. The effective amount of the agent (such as an immunogenic composition provided herein) can be dependent on several factors, including, but not limited to the subject or cells being treated, the particular therapeutic agent, and the manner of administration of the therapeutic composition. In one example, a therapeutically effective amount or concentration is one that is sufficient to prevent advancement, delay progression, or to cause regression of a disease, or which is capable of reducing symptoms caused by the disease, such as a bacterial infection (e.g., tuberculosis).

In one example, a desired response is to reduce or inhibit one or more symptoms associated with a bacterial infection. The one or more symptoms do not have to be completely eliminated for the composition to be effective. The effective amount of an agent that includes one of the disclosed immunogenic compositions that is administered to a human or veterinary subject will vary depending upon a number of factors associated with that subject, for example the overall health of the subject. An effective amount of an agent can be determined by varying the dosage of the product and measuring the resulting therapeutic response, such as the prevention of bacterial infection. Effective amounts also can be determined through various in vitro, in vivo or in situ immunoassays. The disclosed agents can be administered in a single dose, or in several doses, as needed to obtain the desired response.

In particular examples, a therapeutically effective dose of an immunogenic composition includes at least $10^2$ colony forming units (CFU), such as at least $10^3$, at least $10^4$, at least $10^5$, at least $10^6$, at least $10^7$, or at least $10^8$ CFU, for example $10^2$ to $10^8$ CFU. In one example, $10^2$ to $10^8$ CFU of live bacteria are administered intradermally or intranasally. However, one skilled in the art will recognize that higher or lower dosages also could be used, for example depending on the particular immunogenic composition. In particular examples, such daily dosages are administered in one or more divided doses (such as 2, 3, or 4 doses) or in a single formulation. The disclosed immunogenic composition can be administered alone, in the presence of a pharmaceutically acceptable carrier, in the presence of other therapeutic agents.

Treatment:

A therapeutic intervention that ameliorates a sign or symptom of a disease or pathological condition after it has begun to develop. In one example, the immunogenic compositions disclosed herein following administration to a mammal achieves a reduction in one or more signs of a bacterial infection.

Vector:

A nucleic acid molecule as introduced into a host cell, thereby producing a transduced or transformed host cell, referred to herein as a recombinant cell. A vector may include nucleic acid sequences that permit it to replicate in a host cell, such as an origin of replication. A vector may also include one or more selectable marker gene and other genetic elements known in the art. Vectors include plasmid vectors, including plasmids for expression in gram negative and gram positive bacterial cells. Exemplary vectors include those for expression in *E. coli* and *Salmonella*. Vectors also include viral vectors, such as, but are not limited to, retrovirus, orthopox, avipox, fowlpox, capripox, suipox, adenoviral, herpes virus, alpha virus, baculovirus, Sindbis virus, vaccinia virus and poliovirus vectors.

Temperature-Sensitive Essential Genes from Psychrophilic Bacteria

It is disclosed herein that several nucleic acid molecules, and their corresponding peptides, can be introduced into a bacteria to confer temperature sensitivity (TS), such as heat-sensitivity, to the host bacteria. The resulting bacteria can be used to induce an immune response to the temperature-sensitive bacteria, such as a T cell response. Exemplary psychrophilic essential genes with desired temperature sensitivity, and their corresponding peptides, are provided herein. For example, host mesophilic bacteria can be transformed with one or more psychrophile TS essential nucleic acid molecules, thereby conferring TS to the mesophilic bacteria. The resulting recombinant mesophilic bacteria can be formulated into an immunogenic composition, to treat or prevent infection by the meosophilic bacteria. For example, recombinant mesophilic *M. tuburculosis* bacterium containing one or more psychrophile TS essential nucleic acid molecules can be used to treat or prevent tuberculosis. The same approach can be used to make TS forms of *Bacillus anthracis, Brucella abortus, Burkholderia pseudomallei, Haemophilus influenzae, Mycobacterium bovis, Salmonella typhi, Shigella dysenteriae, Staphylococcus aureus, Streptococcus pneumoniae*, and *Yersinia pestis* which cause anthrax, brucellosis, melioidosis, meningitis, bovine tuberculosis, typhoid fever, dysentery, numerous types of nosocomial infections, pneumonia, and plague. Thus, such TS bacteria can be used to treat or prevent such conditions.

Temperature-sensitive essential proteins from a psychrophilic bacterium are provided herein, such as those from *Corwellia* sp., *Psuedoalteromonas* sp., or *Shewanella* sp. Exemplarily proteins include ligA, pyrG, hemC, ftsZ, cmk, murG, fmt, and dnaK. Exemplary sequences are provided in the amino acid sequence shown in SEQ ID NO: 2, 4, 6, 8, 10, 12, 14, 16, 18, 20, 22, 24, 26, and 28. However, one skilled in the art will appreciate that variant sequences can also be used. For example, a peptide having a sequence that is at least 75%, at least 80%, at least 85%, at least 90%, at least 95%, at least 96%, at least 97%, at least 98% or at least 99% identical to the amino acid sequence set forth in one of SEQ ID NOs: 2, 4, 6, 8, 10, 12, 14, 16, 18, 20, 22, 24, 26, and 28 is encompassed by the present disclosure, and can be used in the methods provided herein. Variant sequences retain the biological activity of the native temperature-sensitive essential protein from a psychrophilic bacterium, such as conferring the ability to make a bacterium TS (such as heat sensitivity), for example operable at a temperature of −10° C. to about 30° C. (such as 0° C. to 30° C.), but inoperable at a temperature greater than about 30° C. (for example 4° C. to 30° C.), such as greater than 35° C. Exemplary sequences can be obtained using computer programs that are readily available on the internet and the amino acid sequences set forth herein. In one example, the variant peptide retains a function of the native protein, such as the ability to confer temperature sensitivity to a bacterium.

A specific, non-limiting example of a variant protein is a conservative variant of the native protein (e.g., SEQ ID NOs: 2, 4, 6, 8, 10, 12, 14, 16, 18, 20, 22, 24, 26, and 28). Substitutions of the amino acids sequence shown in SEQ ID NOs: 2, 4, 6, 8, 10, 12, 14, 16, 18, 20, 22, 24, and 28 can be made based on this table, as long as the pathogenic mesophilic bacteria are rendered TS and are able to initiate an immune response to its pathogenic antigens. For example, protein sequences can be altered without significantly altering their biological properties, for example by introducing one or more conservative amino acid substitutions. Therefore, any of SEQ ID NOS: 2, 4, 6, 8, 10, 12, 14, 16, 18, 20, 22 24, 26, or 28 can be modified by making 1 to 20, 1 to 15, 1 to 12, 1 to 10, or 1 to 5 conservative amino acid substitutions, such as 1, 2, 3, 4, 5, 6, 7, 8, 9, 10, 11, 12 13, 14, 15, 16, 17, 18 19 20 or 50 conservative amino acid substitutions, while retaining the ability to render a mesophilic bacteria temperature sensitive (TS). Examples of conservative substitutions are shown below:

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Minor modifications to the disclosed protein sequences can result in peptides which have substantially equivalent activity as compared to the unmodified counterpart protein described herein. Such modifications may be deliberate, as by site-directed mutagenesis, or may be spontaneous. All of the proteins produced by these modifications are included herein.

Temperature-sensitive essential proteins (and nucleic acid molecules) from a psychrophilic bacterium are disclosed herein that can be used to induce temperature sensitivity in a desired bacterial host, wherein the resulting recombinant bacteria can be used to induce an immune response (for example in a mammal). These peptides can include fragments of the full-length native protein, as long as the ability to confer temperature sensitivity in the host cell is retained. In these examples, the peptide does not include the full-length amino acid sequences set forth as 2, 4, 6, 8, 10, 12, 14, 16, 18, 20, 22, 24, 26, and 28. For example no more than 10%, no more than 5%, or no more than 1% of the amino acids can be deleted, such as 1% to 5% of the amino acids.

The isolated temperature-sensitive essential proteins can be part of a fusion protein. Thus, the fusion protein can include the temperature-sensitive essential protein (see above) and a second heterologous moiety, such as a myc protein, an enzyme or a carrier (such as a hepatitis carrier protein or bovine serum albumin) covalently linked to the temperature-sensitive essential protein. In additional examples, the temperature-sensitive essential protein includes six sequential histidine residues, a β-galactosidase amino acid sequence, or an immunoglobulin amino acid sequence, for example at the C- or N-terminus of the temperature-sensitive essential protein. The temperature-sensitive essential protein can also be covalently linked to a carrier. Suitable carriers include, but are not limited to, a hepatitis B small envelope protein HBsAg.

The temperature-sensitive essential proteins disclosed herein can be chemically synthesized by standard methods, or can be produced recombinantly. An exemplary process for polypeptide production is described in Lu et al., *Federation of European Biochemical Societies Letters*. 429:31-35, 1998. Proteins can also be produced using molecular genetic techniques, such as by inserting a nucleic acid encoding a temperature-sensitive essential protein into an expression vector, introducing the expression vector into a host cell. They can also be isolated by methods including preparative chromatography and immunological separations.

Temperature-sensitive essential nucleic acid molecules from a psychrophilic bacterium are provided herein. Exemplary sequences are provided in the nucleic acid sequence shown in SEQ ID NO: 1, 3, 5, 7, 9, 11, 13, 15, 17, 19, 21, 23, 25, and 27. However, one skilled in the art will appreciate that variant sequences can also be used. For example, a nucleic acid molecule having a sequence that is at least 75%, at least 80%, at least 85%, at least 90%, at least 95%, at least 96%, at least 97%, at least 98% or at least 99% identical to the nucleic acid sequence set forth in one of SEQ ID NOs: 1, 3, 5, 7, 9, 11, 13, 15, 17, 19, 21, 23, 25 and 27 (such as at least 75%, at least 80%, at least 85%, at least 90%, at least 95%, at least 96%, at least 97%, at least 98% or at least 99% identical to the nucleic acid sequence set forth in nucleotides 10-2067 of SEQ ID NO: 1, nucleotides 10-2019 of SEQ ID NO: 3, nucleotides 10-2019 of SEQ ID NO: 5, nucleotides 10-2010 of SEQ ID NO: 7) is encompassed by the present disclosure, and can be used in the methods provided herein. In some examples, the codons of a nucleic acid molecule are optimized for the bacterium into which it is introduced. In some examples, such optimization does not alter the amino acid sequence encoded thereby. For example, the psychrophilic bacterium TS essential nucleic acid can be modified to optimize codon usage for the mesophilic bacterium (e.g., *M. tuberculosis* or *F. novicida*) into which the psychrophilic bacterium TS essential nucleic acid is introduced. Exemplary sequences can be obtained using computer programs that are readily available on the internet and the nucleic acid sequences set forth herein. In one example, the variant nucleic acid sequence retains the ability to encode a protein having the function of the native protein, such as the ability to confer temperature sensitivity (e.g., heat sensitivity) to a mesophilic bacterium.

The disclosed temperature-sensitive essential nucleic acid molecules from a psychrophilic bacterium include DNA, cDNA and RNA sequences which encode the temperature-sensitive essential peptide. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Shyer, 1988, Biochemistry, 3.sup.rd Edition, W.H. 5 Freeman and Co., NY).

A nucleic acid molecule encoding a temperature-sensitive essential peptide from a psychrophilic bacterium can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, NY, 1989). Polynucleotides also can be isolated by screening genomic or cDNA libraries with probes selected from the sequences of the desired polynucleotide under stringent hybridization conditions.

The nucleic acid molecules encoding a temperature-sensitive essential peptide from a psychrophilic bacterium include a recombinant DNA which is incorporated into a vector, into an autonomously replicating plasmid or virus, or into the genomic DNA of a prokaryote or eukaryote, or which exists as a separate molecule (such as a cDNA) independent of other sequences. The nucleic acid molecules disclosed herein can be ribonucleotides, deoxyribonucleotides, or modified forms of either nucleotide. The term includes single and double forms of DNA.

The nucleic acid molecules encoding a temperature-sensitive essential peptide from a psychrophilic bacterium can be part of a vector, such as a plasmid or viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like. Other viral vectors that can be used include other DNA viruses such as herpes virus and adenoviruses, and RNA viruses such as retroviruses and polio.

The nucleic acid molecules encoding a temperature-sensitive essential peptide from a psychrophilic bacterium can be operably linked to at least one expression control element. The expression control elements are inserted in the vector or plasmid to control and regulate the expression of the nucleic acid sequence. For example, an expression control sequence operatively linked to a temperature-sensitive essential peptide coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. Specific examples of expression control elements include, but are not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the temperature-sensitive essential peptide from a psychrophilic bacterium in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology," John Wiley and Sons, New York, N.Y.) and are commercially available.

In one example, vector introduced into a host bacterium includes one or more of the following elements: (i) a prokaryotic origin of replication, so that the vector may be amplified in a prokaryotic host: (ii) a gene encoding a marker which allows selection of prokaryotic host cells that contain the vector (e.g., a gene encoding antibiotic resistance); (iii) at least one DNA sequence encoding one or more temperature-sensitive essential peptides from a psychrophilic bacterium located adjacent to a transcriptional promoter capable of directing the expression of the sequence; and (iv) DNA sequences homologous to the region of the parent virus genome where the foreign gene(s) will be inserted, flanking the construct of element (iii).

The vector can contain an additional gene that encodes a marker that will allow identification of recombinant cells containing inserted foreign DNA. These include genes that encode antibiotic or chemical resistance (e.g., see Spyropoulos et al., 1988, *J. Virol.* 62:1046: Falkner and Moss, 1988, *J. Virol.* 62:1849: Franke et al., 1985, *Mol. Cell. Biol.* 5:1918), as well as genes such as the *E. coli* lacZ gene, that permits identification of recombinant plaques by colorimetric assay.

Methods of introducing nucleic acid molecules, such as those that encode a temperature-sensitive essential peptide from a psychrophilic bacterium, are well known to those skilled in the art. Where the host is prokaryotic, such as, a bacterium, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation. Hosts cells can include bacterial cells, such as bacteria that cause disease. Examples of such bacteria that can be used as host cells for temperature-sensitive essential nucleic acids/peptides from a psychrophilic bacterium include without limitation any one or more of (or any combination of) *Acinetobacter baumanii, Actinobacillus* sp., *Actinomycetes, Actinomyces* sp. (such as *Actinomyces israelii* and *Actinomyces naeslundii*), *Aeromonas* sp. (such as *Aeromonas hydrophila, Aeromonas veronii* biovar *sobria* (*Aeromonas sobria*), and *Aeromonas caviae*), *Anaplasma phagocytophilum, Alcaligenes xylosoxidans, Acinetobacter baumanii, Actinobacillus actinomycetemcomitans, Bacillus* sp. (such as *Bacillus anthracis, Bacillus cereus, Bacillus subtilis, Bacillus thuringiensis,* and *Bacillus stearothermophilus*), *Bacteroides* sp. (such as *Bacteroides fragilis*), *Bartonella* sp. (such as *Bartonella bacilliformis* and *Bartonella henselae, Bifidobacterium* sp., *Bordetella* sp. (such as *Bordetella pertussis, Bordetella parapertussis,* and *Bordetella bronchiseptica*), *Borrelia* sp. (such as *Borrelia recurrentis,* and *Borrelia burgdorferi*), *Brucella* sp. (such as *Brucella abortus, Brucella canis, Brucella melintensis* and *Brucella suis*), *Burkholderia* sp. (such as *Burkholderia pseudomallei* and *Burkholderia cepacia*), *Campylobacter* sp. (such as *Campylobacter jejuni, Campylobacter coli, Campylobacter lari* and *Campylobacter fetus*), *Capnocytophaga* sp., *Cardiobacterium hominis, Chlamydia trachomatis, Chlamydophila pneumoniae, Chlamydophila psittaci, Citrobacter* sp. *Coxiella burnetii, Cognebacterium* sp. (such as, *Corynebacterium diphtherias, Corynebacterium jeikeum* and *Corynebacterium*), *Clostridium* sp. (such as *Clostridium perfringens, Clostridium difficile, Clostridium botulinum* and *Clostridium tetani*), *Eikenella corrodens, Enterobacter* sp. (such as *Enterobacter aerogenes, Enterobacter agglomerans, Enterobacter cloacae* and *Escherichia coli,* including opportunistic *Escherichia coli,* such as enterotoxigenic *E. coli,* enteroinvasive *E. coli,* enteropathogenic *E. coli,* enterohemorrhagic *E. coli,* enteroaggregative *E. coli* and uropathogenic *E. coli*) *Enterococcus* sp. (such as *Enterococcus faecalis* and *Enterococcus faecium*)*Ehrlichia* sp. (such as *Ehrlichia chafeensia* and *Ehrlichia canis*), *Erysipelothrix rhusiopathiae, Eubacterium* sp., *Francisella tularensis, Fusobacterium nucleatum, Gardnerella vaginalis, Gemella morbillorum, Haemophilus* sp. (such as *Haemophilus influenzae, Haemophilus ducreyi, Haemophilus aegyptius, Haemophilus parainfluenzae, Haemophilus haemolyticus* and *Haemophilus parahaemolyticus, Helicobacter* sp. (such as *Helicobacter pylori, Helicobacter cinaedi* and *Helicobacter fennelliae*), *Kingella kingii, Klebsiella* sp. (such as *Klebsiella pneumoniae, Klebsiella granulomatis* and *Klebsiella oxytoca*), *Lactobacillus* sp., *Listeria monocytogenes, Leptospira interrogans, Legionella pneumophila, Leptospira interrogans, Peptostreptococcus* sp., *Moraxella catarrhalis, Morganella* sp., *Mobiluncus* sp., *Micrococcus* sp., *Mycobacterium* sp. (such as *Mycobacterium leprae, Mycobacterium tuberculosis, Mycobacterium intracellulare, Mycobacterium avium, Mycobacterium bovis,* and *Mycobacterium marinum*), *Mycoplasm* sp. (such as *Mycoplasma pneumoniae, Mycoplasma hominis,* and *Mycoplasma genitalium*), *Nocardia* sp. (such as *Nocardia asteroides, Nocardia cyriacigeorgica* and *Nocardia brasiliensis*), *Neisseria* sp. (such as *Neisseria gonorrhoeae* and *Neisseria meningitidis*), *Pasteurella multocida, Plesiomonas shigelloides. Prevotella* sp., *Polphyromonas* sp., *Prevotella melaminogenica, Proteus* sp. (such as *Proteus vulgaris* and *Proteus mirabilis*), *Providencia* sp. (such as *Providencia alcalifaciens, Providencia rettgeri* and *Providencia stuartii*), *Pseudomonas aeruginosa, Propionibacterium acnes, Rhodococcus equi, Rickettsia* sp. (such as *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* sp., *Serratia marcescens, Stenotrophomonas maltophilia, Salmonella* sp. (such as *Salmonella enterica, Salmonella typhi, Salmonella paratyphi, Salmonella enteritidis, Salmonella cholerasuis* and *Salmonella typhimurium*), *Serratia* sp. (such as *Serratia marcesans* and *Serratia Shigella* sp. (such as *Shigella dysenteriae, Shigella flexneri, Shigella boydii* and *Shigella sonnei*), *Staphylococcus* sp. (such as *Staphylococcus aureus, Staphylococcus epidermidis, Staphylococcus hemolyticus, Staphylococcus saprophyticus*), *Streptococcus* sp. (such as *Streptococcus pneumoniae* (for example chloramphenicol-resistant serotype 4 *Streptococcus pneumoniae,* spectinomycin-resistant serotype 6B *Streptococcus pneumoniae,* streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae*, *Streptococcus mutans*, *Streptococcus pyogenes*, Group A streptococci, *Streptococcus pyogenes*, Group B streptococci, *Streptococcus agalactiae*, Group C streptococci, *Streptococcus anginosus*, *Streptococcus equismilis*, Group D streptococci, *Streptococcus bovis*, Group F streptococci, and *Streptococcus anginosus* Group G streptococci), *Spirillum minus*, *Streptobacillus moniliformi*, *Treponema* sp. (such as *Treponema carateum*, *Treponema petenue*, *Treponema pallidum* and *Treponema endemicum*, *Tropheryma whippelii*, *Ureaplasma urealyticum*, *Veillonella* sp., *Vibrio* sp. (such as *Vibrio cholerae*, *Vibrio parahemolyticus*, *Vibrio vulnificus*, *Vibrio parahaemolyticus*, *Vibrio vulnificus*, *Vibrio alginolyticus*, *Vibrio mimicus*, *Vibrio hollisae*, *Vibrio fluvialis*, *Vibrio metchnikovii*, *Vibrio damsela* and *Vibrio furnisii*), *Yersinia* sp. (such as *Yersinia enterocolitica*, *Yersinia pestis*, and *Yersinia pseudotuberculosis*) and *Xanthomonas maltophilia* among others.

Following transformation of bacterial cells, recombinant host cells can be identified by one of several techniques. For example, expression of a gene encoding a marker or indicator gene with the temperature-sensitive gene, as described above, can be used to identify recombinant progeny. One specific non-limiting example of an indicator gene is the *E. coli* lacZ gene. Recombinant bacterial cells expressing beta-galactosidase can be selected using a chromogenic substrate for the enzyme. Once a recombinant bacterium has been identified, it can be selected and amplified for use in an immunogenic composition provided herein.

Methods of Making Temperature-Sensitive Bacterial Strains

The exemplary embodiments relate to methods for generating recombinant TS bacteria for use in stimulating an immune response to the TS bacteria. In one aspect, an exemplary TS immunogenic composition is suitable for immunoprophylaxis to prevent infectious disease or alternatively immunotherapy to treat an infectious disease. Such TS bacteria are generated by the introduction of one or more TS essential genes from psychrophilic bacteria into a target bacteria (such as a mesophilic bacteria that causes a disease that one wants to treat or prevent). Thus, the disclosure provides safe immunogenic compositions based on live genetically altered bacterial microorganisms. This was accomplished by taking advantage of essential genes from psychrophilic bacteria, by creating a fusion of the psychrophilic structural genes with the transcriptional and translational control elements of the "host" genome or by making fusions between the host gene and the psychrophilic gene. The exemplary embodiments provide live vaccines and immunogenic compositions that mimic a number of cold adapted viral vaccines and are unable to grow at the normal body temperature.

According to another exemplary embodiment it is suitable for mass production purposes, specifically of antigen; due to the TS strain's non-virulent nature the aerosols produced are rendered harmless and therefore, this methods and compositions disclosed herein can significantly reduce or eliminate human risk of infection.

Another aspect, the methods and compositions provided herein has value as a research diagnostic, or as a research/educational tool because it allows for experimentation to be performed on organisms that are normally highly pathogenic in their viable state without posing threats to the researcher.

The methods and compositions provided herein can be employed to stimulate the immune system with TS organisms with the intention of prevention or treatment of a disease.

A large number of psychrophilic bacteria contain TS genes, which can be used to generate TS mesophilic bacteria of the present disclosure. For example, one or more TS essential genes from psychrophilic bacteria can be introduced into a mesophilic bacterium (for example into a chromosome of a mesophilic bacteria), thereby generating a TS strain that can be used to induce an immune response in a subject into whom it is administered. Recombinant methods for introducing a nucleic acid into bacteria are routine in the art. Appropriate TS essential genes from psychrophilic bacteria can be identified using the methods provided herein. As shown in Tables 1 and 2, nine of the twenty one essential genes from the psychrophilic *C. psychrerhraea* were introduced into *F. novicida* and substituted for an essential host gene to generate TS strains of *F. novicida* ("Group I"). Group I genes generated a range of TS phenotypes with the restrictive temperatures of about 33° C. to 44° C. Thus, the genes of Group I can be used to generate TS strains of the present disclosure. Group II in Table 1 consists of the *C. psychrerhraea* genes that either functioned poorly or not at all in the exemplary bacterial strain *F. novicida*. *F. novicida* strains carrying an integrate with the psychrophilic essential gene resolve the integrate under counter selection pressure generated by the presence of sacB and sucrose. However, the resolved strains retain copies of both the psychrophilic gene and the *F. novicida* homologue and the strains are not TS ("Group III" in Table 1); indicating that these psychrophilic essential genes do not function in the mesophilic host. Alleles of the same gene from different psychrophilic bacteria can be selected to identify those that generate hybrid strains with the same TS properties when substituted into the chromosomes of mesophilic bacteria. The ligA alleles from three different psychrophilic bacteria generated three different TS phenotypes when substituted into the mesophile *F. novicida*. The pyrG$_{Cp}$ allele from *C. psychrerhraea* created a TS strain when substituted into *F. novicida* but the pyrG$_{Sf}$ allele from *S. frigidimarina* (SF) did not. PH refers to *P. haloplanktis*.

TABLE 1

| Gene symbol | Restrictive Temp. (° C.) Source | Product Function | Group |
| --- | --- | --- | --- |
| ligA$_{Ph2}$ | 28/PH | NAD-dependent DNA ligase | I |
| ligA$_{Sf}$ | 33/SF | NAD-dependent DNA ligase | I |
| ligA$_{Cp}$ | 34/CP | NAD-dependent DNA ligase | I |
| ligA$_{Ph}$ | 36.8/PH | NAD-dependent DNA ligase | I |
| hemC$_{Cp}$ | 36.8/CP | Porphobilinogen deaminase (Hydroxymethylbilane synthase) | I |
| pyrG$_{Cp}$ | 37.2/CP | CTP synthetase | I |
| dnaK$_{Cp}$ | 38.2/CP | Molecular chaperone DnaK | I |

TABLE 1-continued

| Gene symbol | Restrictive Temp. (° C.) Source | Product Function | Group |
|---|---|---|---|
| murG$_{Cp}$ | 38.2/CP | UDP-N-acetylglucosamine-N-acetylmuramyl-(pentapeptide) pyrophosphoryl-undecaprenol N-acetylglucosamine transferase | I |
| fmt$_{Cp}$ | 41/CP | Methionyl-tRNA formyltransferase | I |
| ftsZ$_{Cp}$ | 42/CP | Cell division protein | I |
| cmk$_{Cp}$ | 43/CP | Cytidylate kinase | I |
| tyrS$_{Cp}$ | 44/CP | Aminoacyl tRNA synthetases for Tyr | I |
| adk$_{Cp}$ | >44/CP | Adenylate kinase (proved resolution) | II |
| accD$_{Cp}$ | >44/CP | AcetylCoA carboxylase. The F. novicida integrate containing accD$_{Cp}$ fails to resolve. | II |
| murI$_{Cp}$ | >44/CP | Glutamate racemase. The CP version of MurI appears to function poorly at all temperatures in F. novicida. | II |
| pyrG$_{Sf}$ | >44/SF | CTP synthetase | III |
| trxA$_{Cp}$ | >44/CP | Thioredoxin | III |
| glmS$_{Cp}$ | >44/CP | Glucosamine-fructose-6-phosphate aminotransferase | III |
| argS$_{Cp}$ | >44/CP | Aminoacyl tRNA synthetases for Arg | III |
| cds$_{Cp}$ | >44/CP | phosphatidate cytidylyltransferase | III |
| mur$_{Cp}$C | >44/CP | UDP-N-acetylmuramate-alanine ligase | III |
| valS$_{Cp}$ | >44/CP | Aminoacyl tRNA synthetases for Val | III |
| proS$_{Cp}$ | >44/CP | Aminoacyl tRNA synthetases for Pro | III |
| metK$_{Cp}$ | ≤44/CP | S-adenosylmethionine synthetase | III |
| ftsW$_{Cp}$ | >44/CP | Cell division protein | III |

TABLE 2

| Gene | Restricted Temp (° C.) | Challenge Temp (° C.) | Mutation rate in F. novicida to temperature resistance | | |
|---|---|---|---|---|---|
| | | | Trial #1 | Trial #2 | Trial #3 |
| ligA$_{Sf}$ | 33 | 37 | $4.0 \times 10^{-6}$ | $3.3 \times 10^{-7}$ | $9.7 \times 10^{-7}$ |
| ligA$_{Cp}$ | 34 | 37 | $<1.2 \times 10^{-10}$ | $<7.93 \times 10^{-11}$ | $<1.1 \times 10^{-10}$ |
| ligA$_{Ph}$ | 36.8 | 39 | $<1.5 \times 10^{-10}$ | $<7.8 \times 10^{-11}$ | $<6.2 \times 10^{-11}$ |
| dnaK$_{Cp}$ | 38.2 | 39.5 | $<3.2 \times 10^{-10}$ | $<1.9 \times 10^{-10}$ | $<3.2 \times 10^{-10}$ |
| hemC$_{Cp}$ | 36.8 | 43 | $<2.5 \times 10^{-10}$ | $<3.6 \times 10^{-11}$ | $<3.7 \times 10^{-11}$ |
| pyrG$_{Cp}$ | 37.2 | 40 | $8.5 \times 10^{-8}$ | $1.0 \times 10^{-9}$ | $6.5 \times 10^{-8}$ |
| murG$_{Cp}$ | 38.2 | 43 | $2.6 \times 10^{-4}$ | $3.0 \times 10^{-5}$ | $8.5 \times 10^{-5}$ |
| dnaK$_{Sf}$ | 39 | 42 | $3.1 \times 10^{-10}$ | $8.5 \times 10^{-10}$ | |

To make a TS bacterial pathogen, an essential gene from an Arctic psychrophile bacterium was substituted into the genome of a mesophilic pathogenic bacterium. The Arctic bacterial essential gene ligA$_{Sf}$ rendered F. novicida unable to grow at a temperature of 33° C. or higher. Table 2 outlines the restrictive temperature properties imposed on F. novicida following the replacement of the mesophilic essential gene for its psychrophilic counterpart. Any of the genes in Table 2 may be introduced into a pathogenic bacteria strain to create live heat-sensitive vaccines. Exemplary pathogenic bacteria include but are not limited to: *Mycobacterium* sp., *Haemophilus* sp., *Vibrio* sp., *Escherichia* sp., *Salmonella* sp., *Streptococcus* sp., *Burkholderia* sp., *Campylobacter* sp., *Neisseria* sp., and *Francisella* sp.

The disclosure relates to genes derived from psychrophilic bacteria for use in the development of heat-sensitive immunogenic compositions, and methods of using these compositions to stimulate an immune response in a subject. In a specific example, the disclosure provides recombinant pathogens (such as *Mycobacterium* sp., *Haemophilus* sp., *Vibrio* sp., *Escherichia* sp., *Salmonella* sp., *Streptococcus* sp., *Burkholderia* sp., *Campylobacter* sp., *Neisseria* sp., and *Francisella* sp.) containing one or more heat-sensitive genes, exemplified by ligA, pyrG, hemC, ftsZ, cmk, dnaK, and fmt, that can be administered to a subject to provide a prophylactic immune response against diseases caused by such bacteria.

Methods of making a recombinant temperature-sensitive (TS) bacterial cell are provided. In one example the method includes introducing into the genome of a mesophilic bacterial strain a nucleic acid construct that includes a TS essential nucleic acid molecule from a psychrophilic bacteria (such as one that encodes a peptide that is operable at a temperature of about −10° C. to about 30° C., and/or inoperable at a temperature greater than about 30° C., for example *Corwellia* sp., *Psuedoalteromonas* sp., or *Shewanella* sp) and one or more control sequences operably linked to the TS essential nucleic acid molecule. The temperature-sensitive essential polynucleotide renders the mesophilic bacteria operable at a temperature less than about 30° C. and inoperable at a temperature greater than about 30° C. In some examples, the temperature-sensitive essential nucleic acid molecule includes a nucleotide sequence having at least 80%, at least 90%, or at least 95% sequence identity to the nucleotide sequence shown in SEQ ID NO: 1, 3, 5, 7, 9, 11, 13, 15, 17, 19, 21, 23, 25, or 27. In some examples the method also includes isolating the TS essential nucleic acid molecule from the genome of the psychrophilic bacterial strain. The method can also include constructing or generating the nucleic acid construct comprising the TS essential nucleic acid molecule and one or more control sequences operably linked to the TS essential nucleic acid molecule.

In some examples, the method further includes culturing the recombinant TS bacterial host cell at a temperature wherein the temperature-sensitive peptide is operable, whereby said recombinant TS bacterial host cell produces a plurality of peptides; increasing the culturing temperature to a temperature at which the temperature-sensitive peptide is inoperable; maintaining said culturing for a period of time sufficient to kill the recombinant TS bacterial host cell; and harvesting the killed recombinant TS bacterial host cells.

Methods of making a recombinant TS bacterial host cell can also include the following. A psychrophilic microbial genome is screened for detection of a TS essential polynucleotide that encodes a peptide that is inactivated at about greater than 30° C.; isolating said TS essential polynucleotide; constructing a nucleic acid construct comprising the TS essential polynucleotide and one or more control sequences operably linked to the TS polynucleotide; inserting the nucleic acid construct into the genome of a selected mesophilic bacterial host cell (such as *Francisella novicida*) thereby functionally replacing the host cell's homologue of the TS essential polynucleotide whereby the TS peptide (and thus the bacteria in which it is expressed) is operable at a temperature less than about 30° C., and inoperable at a temperature greater than about 30° C. and mimics the temperature sensitivity of the original designated host bacterium. The resulting recombinant mesophilic bacterial host cell comprising the TS polynucleotide is cultured or grown at a temperature less than about 30° C. to confirm the viability of the recombinant mesophilic bacterial host cell; further culturing the recombinant mesophilic bacterial host cell comprising the TS polynucleotide at a temperature greater than about 30° C. to determine if the mesophilic bacterial host cell is killed. If the mesophilic bacterial host cell is killed, the nucleic acid construct is introduced into the genome of a selected destination mesophilic bacterial host cell (such as *Salmonella* sp. or *Mycobacterium* sp.) thereby functionally replacing the host cell's homologue of the temperature-sensitive essential polynucleotide whereby the temperature-sensitive peptide (and thus the bacteria in which it is expressed) is operable at a temperature less than about 30° C., and inoperable at a temperature greater than about 30° C. and mimics the temperature sensitivity of the original tester host bacterium.

In some examples, the mesophilic bacteria is one that is operable at a temperature selected from the range of about 10° C. to about 50° C. prior to introduction of the TS essential nucleic acid molecule from a psychrophilic bacteria. Examples of such mesophilic bacteria include strains of fermentative bacteria or bioremediation bacteria. Other exemplary bacteria are provided above.

In some examples, the TS essential nucleic acid molecule expresses a peptide during a culturing of the recombinant TS bacteria, such as a peptide having at least 80%, at least 90%, or at least 95% sequence identity to an amino acid sequence shown in SEQ ID NO: 2, 4, 6, 8, 10, 12, 14, 16, 18, 20, 22, 24, 26, or 28.

Recombinant TS bacteria generated by these methods, as well as compositions that include such bacteria, are also provided herein.

Temperature-Sensitive Bacterial Strain Compositions

Compositions are provided that include recombinant TS bacteria provided herein. In some examples, the compositions include more than one type of recombinant TS bacteria, such as 2, 3, 4 or 5 different recombinant TS bacteria. In some examples, the recombinant TS bacteria contain two or more different TS essential psychrophilic coding sequences (such as two or more of the Group I genes listed in Table 1, such as ligA and another Group I gene). In particular examples, the recombinant TS bacteria is a *Francisella* sp., *Salmonella* sp., or *Mycobacterium* sp. (other particular examples are provided above).

In some examples, such compositions are immunogenic, in that they can stimulate an immune response in a mammal. The compositions can include other components, such as pharmaceutically acceptable carriers (such as saline), adjuvants, preservatives, combinations thereof, and the like.

Methods of Stimulating an Immune Response Using Temperature-Sensitive Bacterial Strains The TS recombinant bacteria disclosed herein can be used to generate an immune response in a subject. In some examples, the subject is infected with a bacterium, or as at risk of being infected with a bacterium (such as a health care worker), such as *Mycobacterium tuberculosis*. Thus, in several embodiments, the methods include administering to a subject a therapeutically effective amount of one or more of the TS recombinant bacteria disclosed herein in order to generate an immune response, such as, but not limited to, a protective immune response. For example, two or more different TS recombinant bacteria (such as those expressing different TS essential peptides from psychrophilic bacteria) can be used to generate an immune response in a subject. In some examples, the recombinant bacterium used to generate an immune response in a subject expresses two or more different temperature-sensitive essential peptides from a psychrophilic bacterium or the same temperature-sensitive essential peptide from two or more different psychrophilic bacteria.

The TS recombinant bacterium administered is selected based on the bacterial infection to be prevented or treated. For example, if the bacterial infection to be prevented or treated in the subject is tuberculosis, then the TS recombinant bacteria is *Mycobacterium tuberculosis* expressing at least one TS essential peptide from a psychrophilic bacterium. In another example, if the bacterial infection to be prevented or treated in the subject is tularemia, then the TS recombinant bacteria is *F. tularensis* expressing at least one TS essential peptide from a psychrophilic bacterium.

In exemplary applications, compositions are administered to a subject having in an amount sufficient to produce an immune response to the TS recombinant bacteria. These TS recombinant bacteria are of use to prevent a bacterial infection (such as *Mycobacterium tuberculosis*) prevent progression to disease in a subject having a latent bacterial infection, or to treat a disease resulting from the bacterial infection (such as tuberculosis). In several examples, administration of a therapeutically effective amount of a composition including the TS recombinant bacteria disclosed herein induces a sufficient immune response to decrease a symptom of a disease due to bacterial infection, to prevent the development of one or more symptoms of the disease associated with the infection, or to prevent infection with the bacteria.

In some examples, the compositions are of use in preventing a future bacterial infection. Thus, a therapeutically effective amount of the composition is administered to a subject at risk of becoming infected with a bacterium, such as *Mycobacterium tuberculosis*. For example the disclosed compositions can be used to prevent the development of tuberculosis, such as latent or active tuberculosis in the subject upon subsequent exposure to *Mycobacterium tuberculosis*. In one example, the compositions are administered to a subject with a latent *Mycobacterium tuberculosis* infection, and prevent the development of symptoms of tuberculosis. Thus the compositions are of use in treating a subject with latent tuberculosis, such that the subject does not develop active tuberculosis.

Amounts effective for these uses will depend upon the severity of the disease, the general state of the patient's health, and the robustness of the patient's immune system. In one example, a therapeutically effective amount of the compound is that which provides either subjective relief of a symptom(s) or an objectively identifiable improvement as noted by the clinician or other qualified observer. In other examples, a therapeutically effective amount is an amount sufficient to prevent an infection with the bacterium in a subject upon subsequent exposure of the subject to the bacterium. In additional examples, a therapeutically effective amount is an amount sufficient to prevent development of symptom in a subject infected with a bacterium.

The TS recombinant bacteria-containing composition can be administered by any means known to one of skill in the art either locally or systemically, such as by intramuscular injection, subcutaneous injection, intraperitoneal infection, intravenous injection, oral administration, nasal administration, transdermal administration or even anal administration. In one embodiment, administration is by oral, subcutaneous injection or intramuscular injection. To extend the time during which the TS recombinant bacteria is available to stimulate a response, the TS recombinant bacteria can be provided as an implant, an oily injection, or as a particulate system. The particulate system can be a microparticle, a microcapsule, a microsphere, a nanocapsule, or similar particle. A particulate carrier based on a synthetic polymer has been shown to act as an adjuvant to enhance the immune response, in addition to providing a controlled release. Aluminum salts can also be used as adjuvants to produce an immune response.

In one specific, non-limiting example, the TS recombinant bacteria are administered in a manner to direct the immune response to a cellular response (that is, a cytotoxic T lymphocyte (CTL) response), rather than a humoral (antibody) response.

Optionally, one or more cytokines, such as IL-2, IL-6, IL-12, RANTES, GM-CSF, TNF-α, or IFN-γ, one or more growth factors, such as GM-CSF or G-CSF; one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, J. Surg. Oncol. 68 (2):122-38; Lotze et al., 2000, Cancer J Sci. Am. 6 (Suppl 1):S61-6; Cao et al., 1998, Stem Cells 16 (Suppl 1):251-60; Kuiper et al., 2000, Adv. Exp. Med. Biol. 465:381-90). These molecules can be administered systemically (or locally) to the subject. In some examples, IL-2, RANTES, GM-CSF, TNF-α, IFN-γ, G-CSF, LFA-3, CD72, B7-1, B7-2, B7-1 B7-2, OX-40L, 41 BBL and ICAM-1 are administered. In various embodiments, the nucleic acid encoding the biological adjuvant can be cloned into same vector as the psychrophilic TS essential peptide coding sequence, or the nucleic acid can be cloned into one or more separate vectors for co-administration into the bacteria.

A pharmaceutical composition including TS recombinant bacteria is thus provided. These compositions are of use to promote an immune response to a particular bacterium. In one embodiment, TS recombinant bacteria are mixed with an adjuvant containing two or more of a stabilizing detergent, a micelle-forming agent, and an oil. Suitable stabilizing detergents, micelle-forming agents, and oils are detailed in U.S. Pat. No. 5,585,103; U.S. Pat. No. 5,709,860; U.S. Pat. No. 5,270,202; and U.S. Pat. No. 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly (oxy-1,2-ethanediyl; manufactured by ICI Americas, Wilmington, Del.), TWEEN 40™, TWEEN 20™, TWEEN 60™, ZWITTERGENT™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, J. Am. Oil. Chem. Soc. 54:110, 1977, and Hunter et al., J. Immunol 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, J. Immun. 133:3167, 1984. The agent can be provided in an effective amount, for example between 0.5 and 10%, or in an amount between 1.25 and 5%.

In one example oil is included in the composition. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

In one embodiment, the adjuvant in the composition is a mixture of stabilizing detergents, micelle-forming agent, and oil available under the name PROVAX® (IDEC Pharmaceuticals, San Diego, Calif.). An adjuvant can also be an immunostimulatory nucleic acid, such as a nucleic acid including a CpG motif, or a biological adjuvant (see above).

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly (see Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

In particular examples, at least $10^2$ CFU of the TS bacteria disclosed herein are administered per dose, such as at least $10^3$ CFU, at least $10^4$ CFU, at least $10^5$ CFU, at least $10^6$ CFU, at least $10^7$ CFU, at least $10^8$ CFU, such as $10^2$ to $10^8$ CFU or $10^4$ to $10^8$ CFU. In particular examples, such dosages are administered intradermal or intranasal.

Single or multiple administrations of the compositions are administered depending on the dosage and frequency as required and tolerated by the subject. In one embodiment, the dosage is administered once as a bolus, but in another embodiment can be applied periodically until a therapeutic result is achieved. In one embodiment, the dose is sufficient to treat or ameliorate symptoms or signs of bacterial infection without producing unacceptable toxicity to the subject. In another embodiment, the dose is sufficient to prevent infection with a bacterium upon subsequent exposure to the bacterium (such as *M. tuberculosis*). In a further embodiment, the dose is sufficient to prevent a symptom of bacterial infection (e.g., tuberculosis) in a subject with a latent bacterial infection. Systemic or local administration can be utilized.

Thus the disclosure provides methods for producing an immune response to a bacterium in a subject. The method can include administering to the subject a therapeutically effective amount of a TS bacterium, wherein the temperature-sensitive bacterium expresses a psychrophilic TS essential protein or nucleic acid molecule provided herein (such as a nucleic acid coding sequence in a vector), thereby inducing an immune response to the bacterium. The method can further include administering other agents, such as an adjuvant or antimicrobial agent (such as an antibiotic). In some examples, the immune response is a protective immune response. The subject may have a bacterial infection, be at risk for acquiring a bacterial infection, or have a latent bacterial infection. Exemplary bacterial infections include infections with is *M. tuberculosis, Salmonella* or *Francisella*.

Methods of measuring an immune response following stimulation with a bacterial antigen, such as a cytokine response, are known in the art. In some examples, the method further includes measuring an immune response following administration of the therapeutic compositions provided herein. In one example, a cytokine response is increased following administration of the composition provided herein, such as an increase relative to the absence of administration of the composition. In one example, cytokine production increases by at least 20%, such as at least 40%, at least 50%, at least 75%, at least 90%, or at least 95% following administration of the composition, relative to the cytokine response in the absence of administration of the composition.

The disclosure is illustrated by the following non-limiting Examples.

EXAMPLE 1

This example pertains to an exemplary method to create recombinant psychrophilic genes joined to flanking DNA of a mesophilic host.

FIG. 1a exemplifies the fusion PCR (also known as, "extension overlap PCR", "overlap PCR" or "splice overlap PCR") strategy used to incorporate the *C. psychrerythraea* essential gene (C2) into the wt *F. novicida* genome. The *C. psychrerythraea* genes were engineered with overlap PCR to contain the ribosome binding site (RBS) and the initial three codons and stop codon of the surrounding *F. novicida* genes (F1 and F3) to promote translation of the C2 gene at normal levels for *F. novicida*. The fusion PCR product was ligated to an erythromycin resistant sacB cassette ($Em^R$-sacB) prior to its transformation into *F. novicida*. $Em^R$ colonies containing the fusion PCR product were grown in the presence of sucrose and colonies were screened for the loss of $Em^R$, the *F. novicida* essential gene (F2), and the presence of C2.

FIG. 1*b* illustrates the introduction of the psychrophilic gene fusion construct into the target organism's chromosome via a single crossover event. Furthermore, it illustrates that the excision can be enhanced using the counter-selectable sacB marker. For genes that are not a part of a multi-cistronic operon the upstream pathogen genomic region was fused to the psychrophilic structural gene from codon 4 through to the stop codon. A similar approach was used when substituting a psychrophilic allele into the middle of an operon. However, as one skilled in the art can appreciate, depending on the nature of the operon, some of the codons at the C terminus of the host homologue remained if they were important for translation of the downstream cistron.

EXAMPLE 2

This example pertains to an exemplary method to insert the psychrophilic allele into the mesophilic bacteria.

FIG. 2*a* illustrates the substitution region for the psychrophilic ligA gene, corresponding to SEQ ID NO: 1. Additionally, it illustrates its incorporation into the wt *F. novicida* chromosome. FIGS. 2*b-e* illustrate the integration point for the psychrophilic ligA genes of *C. psychrerythraea, S. frigidmarina, P. haloplanktis* I, and *P. haloplanktis* 2 respectively. The first three codons for *F. novicida* were retained in order to maximize the potential for ligA expression levels. FIG. 2*a-e* illustrates that in most cases the integration and excision events result in a simple substitution of the psychrophilic gene for the mesophilic host homologue. However, the integration and excision events may also lead to the formation of a hybrid gene as illustrated in FIG. 1*b*.

EXAMPLE 3

This example pertains to an exemplary method to determine the maximal growth temperature of each bacterial strain and to show its growth properties at restrictive temperatures.

Each bacterial strain was tested on agar plates placed in a highly stable (±1° C.) incubator; the restrictive temperatures were defined as the lowest temperatures that did not permit the formation of isolated colonies on an agar streak plate. The growth properties at different temperatures of four different transgenic strains of *F. novicida* carrying psychrophilic ligA substitutions and the growth properties of wt *F. novicida* are shown in FIGS. 3-6. The psychrophilic ligA genes are $ligA_{Cp}$, $ligA_{Sf}$, $ligA_{Ph}$ and $ligA_{Ph2}$, as represented by SEQ ID NOs: 1, 7, 3, and 5 respectively. In the first panels in FIGS. 3-6, growth is shown at a permissive temperature, i.e., a temperature below the restrictive temperature. In subsequent panels, growth of both the transgenic and wt strains is shown before and after a shift to the restrictive temperature or higher.

Extended growth curves of both the *F. novicida* transgenic and wt strains are shown as inserts in select panels of FIG. 3-6. These curves were generated by taking a fully grown culture, diluting it, and monitoring its growth in fresh growth media. More specifically, the wt and TS transgenic *F. novicida* cultures were grown at restrictive temperatures until they reached stationary phase at which point, they were diluted and re-incubated for growth at the restrictive temperatures again. The additional growth curves demonstrate that the cessation of growth exhibited by the transgenic strain is a real phenomenon, as opposed to a temporary adjustment to the temperature shift.

EXAMPLE 4

This pertains to an exemplary method used to determine the frequency of mutations that permit bacterial growth at temperatures higher than the restrictive temperature of TS *F. novicida* transgenic strains.

Cultures were grown to late logarithmic phase at the permissive growth temperature, they were then diluted in a series of $10^9$-$10^5$ cells/plate on agar and incubated at temperatures about 3° C. above the restrictive temperature, as well as at temperatures about 3° C. below the restrictive temperature. From this dilution series the rate of mutations that allow for growth at higher temperatures were calculated, Table 2 exemplifies the frequency of mutation to temperature resistance in *F. novicida*. Remarkably, some of the psychrophilic genes are unable to mutate to forms that will function above their restrictive temperature. One skilled in the art may hypothesize that the millions of years required to adapt to a cold climate renders some of the psychrophilic essential gene products unable to adopt simple changes allowing them to function in temperatures typical to their mesophilic counterparts. These include ligACp, $ligA_{Ph}$, $hemC_{Cp}$, $dnaK_{Cp}$, $fmt_{Cp}$, and $dnaK_{Sf}$.

EXAMPLE 5

This example pertains to an exemplary method to determine the duration of viability of the recombinant TS bacterial strains at the restrictive temperature.

An exemplary culture of a TS transgenic strain that has a maximal growth temperature of about 33° C., was grown at about 30° C. and a sample of the culture was incubated at about 37° C. to mimic the typical temperature of human body core tissues. Samples were taken at varying time points between 0-24 hours, and the individual samples were re-diluted, plated on to growth media, and then cultured at about 30° C. to determine the death rate above the restrictive temperature. As a control, the same experiment was carried out with the wt bacterium.

The persistence of *F. tularensis* strains carrying the psychrophilic essential genes within their macrophages was determined. Transgenic strains were cultured at about 30° C. and used to infect macrophages at about 37° C. in 24 well tissue culture plates using standard methods known to those skilled in these arts. For several days monitoring the infected macrophages a subset of cells were lysed and the bacteria were plated onto agar medium and incubated at about 30° C. The data generated in these experiments showed the lifespan of transgene strains during an infection with macrophages at a restrictive temperature and helped to predict the persistence of TS strains during infections.

This example can be extrapolated to provide an in vitro correlation for what can occur in a mammal. A TS transgenic strain will grow in a cool part of the body such as the skin. Replication of the strain at and about this cool site will constantly cause the TS transgenic strain progeny to be moved into the draining lymph nodes. Depending on the locations of the lymph nodes and the restrictive temperature of the TS transgenic strain, the TS progeny will die over a period of several hours. The presence of the TS transgenic strain both in its live and dead states will stimulate an immune response.

EXAMPLE 6

This pertains to an exemplary method to determine the ability of a TS essential gene from a psychrophile to impart its TS phenotype on a mesophilic bacterium. Specifically, it provides a method for transferring a psychrophilic essential gene encoding a TS product to a variety of bacteria as well as the transfer of the TS essential gene between mesophiles.

Several psychrophilic essential genes were substituted into the genome of the mesophilic bacterium *F. novicida*. Multiple approaches can be used to inserting a psychrophilic essential gene into a given bacterium in place of its mesophilic homologue. Furthermore, it can be appreciated that one can substitute a given psychrophilic essential gene into many different bacteria. The following three methods exemplify various ways of substituting $ligA_{Cp}$ into three different bacteria. A common approach to gene substitution is illustrated in FIG. 1b, and involves the integration of a foreign gene in a bacterium that is in close proximity to the hosts' homologous gene through PCR. Following integration, a counter selective marker, such as sacB, can be used to help identify the results of the integration and excision events. Specifically this approach was used to replace the *F. novicida* ligA gene with the psychrophilic $ligA_{Cp}$ gene.

An alternate approach was used to replace the *S. enterica* ligA. The strain of *S. enterica* used had a bacteriophage Mu insertion in the chromosomal copy of ligA (Park et al., 1989. *J. Bacterial.* 171: 2173-80). A wt copy of the bacteriophage T4 DNA ligase was carried on the ampicillin resistant plasmid, pBR313. The $ligA_{Cp}$ gene was introduced on the compatible chloramphenicol resistant plasmid, pSUP2716, and the recombinant *S. enterica* strain was cultured in the absence of ampicillin and the presence of chloramphenicol. These growth conditions allow the pBR313:T4 DNA ligase recombinant plasmid to be lost. *S. enterica* strains that had lost the plasmid encoding the T4 DNA ligase, rendering them ampicillin sensitive, were dependant on the $ligA_{Cp}$ for viability and were TS.

Another alternate approach can be employed when introducing a psychrophilic essential gene into Gram-positive bacteria. The method of insertion of $ligA_{Cp}$ into *M. smegmatis* described herein exemplifies this method. A version of $ligA_{Cp}$ (SEQ ID NOS: 17 and 18) designed with optimal codons was cloned into the mycobacterial plasmid, pSM1; this a precautionary step due to the low G+C content in the $ligA_{Cp}$ gene when compared to that of the *M. smegmatis* and *M. tuberculosis* ligA genes. The recombinant pSMT3:$ligA_{Cp}$ was electroporated into *M. smegmatis*. Subsequently a large fragment of the *M. smegmatis* ligA gene was deleted resulting in a strain dependent on $ligA_{Cp}$ for viability. This strain was TS at about 34° C. This temperature is reflective of the TS nature of the *F. novicida* transgene strain encoding $ligA_{Cp}$.

This example illustrates the use of a mesophilic tester strain which contains a psychrophilic essential gene to predict the TS phenotype when said psychrophilic essential gene is used to construct a transgene strain of another mesophilic bacterium. In this example, the tester strain was *F. novicida*. The substitution of $ligA_{Cp}$ for the *F. novicida* ligA homologue showed that $ligA_{Cp}$ functioned in the mesophile and imparted a TS phenotype having a restrictive temperature of about 34° C. The phenotype of the transgenic strain of *F. novicida* carrying $ligA_{Cp}$ predicted that substitution of the $ligA_{Cp}$ gene into other mesophiles (destination hosts) would results in viable bacteria that had a restrictive temperature of 34° C. The phenotype of the *Salmonella* and *Mycobacteria* transgene strains carrying $ligA_{Cp}$ showed that the inter-genus transfer of a TS psychrophilic essential gene could result in a phenotype seen in the tester strain.

EXAMPLE 7

This example describes an exemplary method to combine psychrophilic genes or fragments thereof (as represented by SEQ ID NO 1-24) or mutant essential psychrophilic genes to create gene products with desired TS properties.

Combining about 30%, at the 5'-end, of the novicida pyrG gene with about ⅔ of the 3'-end of the *C. psychrerythraea* pyrG gene ($pyrG_{Cp}$) in the region of codon 157-159 created a recombinant gene that was TS at 37° C. The *F. novicida* and *C. psychrerythraea* pyrG genes are identical at codons 157-159 inclusive. Additionally, the single point mutation at amino acid residue 149 in $ligA_{Ph}$ from an asparagine ("N") residue to a lysine ("K") residue changes the restrictive temperature from 37° C. to 28° C.

This approach could be applied to different psychrophilic genes by using either in vitro or in vivo recombinant technologies to combine two or more homologues of the same gene.

EXAMPLE 8

This example pertains to an exemplary method to determine the distribution of a transgenic strain from a site of infection in a mammal.

*F. novicida* (a.k.a. *F. tularensis* subspecies *novicida*) carrying a psychrophilic transgene was used. One skilled in the art will appreciate that similar methods can be used to generate and examine TS strains of *F. tularensis*. *F. novicida* is highly virulent in mice. The infection of mice by *F. novicida* serves as a model for the infection of larger mammals with *F. tularensis*. Most strains of *F. tularensis* are highly virulent in most mammals.

The distribution of *F. novicida* transgenic strains from the site of infection was assessed either by injecting the recombinant strains through the skin, or by introduction via the nose, and measuring the amount of viable *F. novicida* cells in internal organs such as the lung, liver and spleen about three to ten days after the inoculation. It was found that TS *F. novicida* transgenic strains did not spread significantly from the site of inoculation. A direct correlation between the inactivation temperature of the psychrophilic essential gene and the level of distribution throughout the system was observed; the dissemination of TS *F. novicida* strains is Lewis Rats is outlined in Table 3.

TABLE 3

| *F. novicida* strain | Restrictive Temp. (° C.) | CFU/Tail injection site | CFU/Spleen |
|---|---|---|---|
| wt⁻ | 45 | $9.7 \times 10^3 / 7.1 \times 10^3$ | $3.7 \times 10^6 / 2.2 \times 10^6$ |
| ligA$_{Cp}$ | 34 | $5 \times 10^2 / 3 \times 10^2$ | 0/0 |
| ligA$_{Ph}$ | 36.8 | $3 \times 10^2 / 2 \times 10^2$ | 0/0 |
| dnaK$_{Cp}$ | 38.2 | $1.5 \times 10^4 / 7.6 \times 10^4$ | $5.0 \times 10^2 / 0$ |
| fmt$_{Cp}$ | 41 | $5.2 \times 10^3 / 2.4 \times 10^3$ | $3.5 \times 10^5 / 2.1 \times 10^5$ |

As a further example, one of the psychrophilic essential genes (ligA$_{Cp}$) was substituted into the genome of *M. tuberculosis* to create a transgenic strain. Some psychrophilic essential genes originate in bacteria with DNA with low G+C content. Thus the genes were optimized with codons for *M. tuberculosis* prior to inserting the psychrophilic genes into the pathogenic bacteria (SEQ ID NOS: 17 and 18 provide the optimized sequences). Codon optimization is a method well known to those skilled in these arts and can be accomplished using freely available bioinformatic tools. The codon optimized psychrophilic essential genes were inserted into *M. tuberculosis* by methods that are well described in Examples 1 and 2. *M. tuberculosis*, like *M. smegmatis*, are Gram-positive bacteria.

Figure 8:
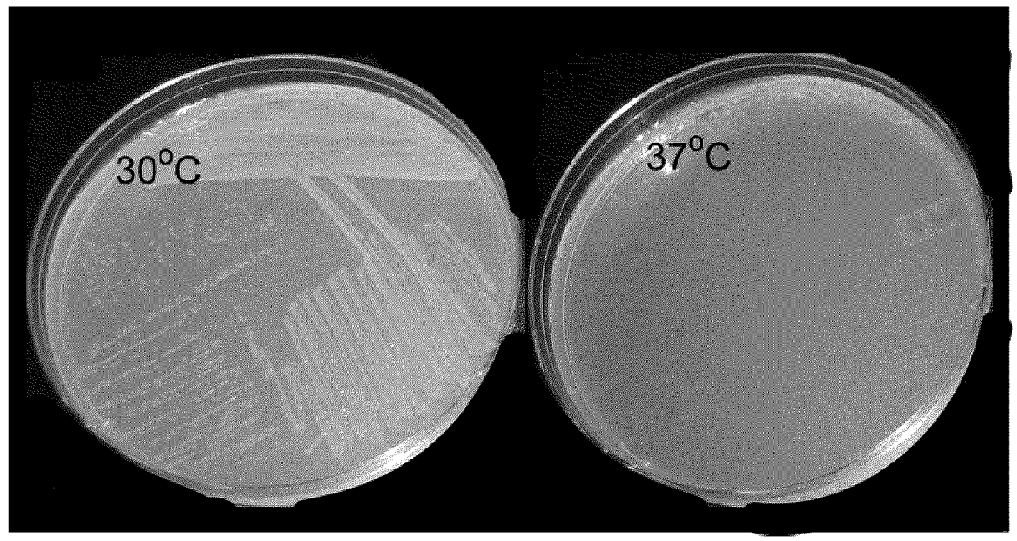
FIG. 8 is a digital image illustrating the growth of *S. ser. Typhimurium*-ligA$_{CP}$ at 30° C. and the lack of growth at 37° C.
Figure 9:
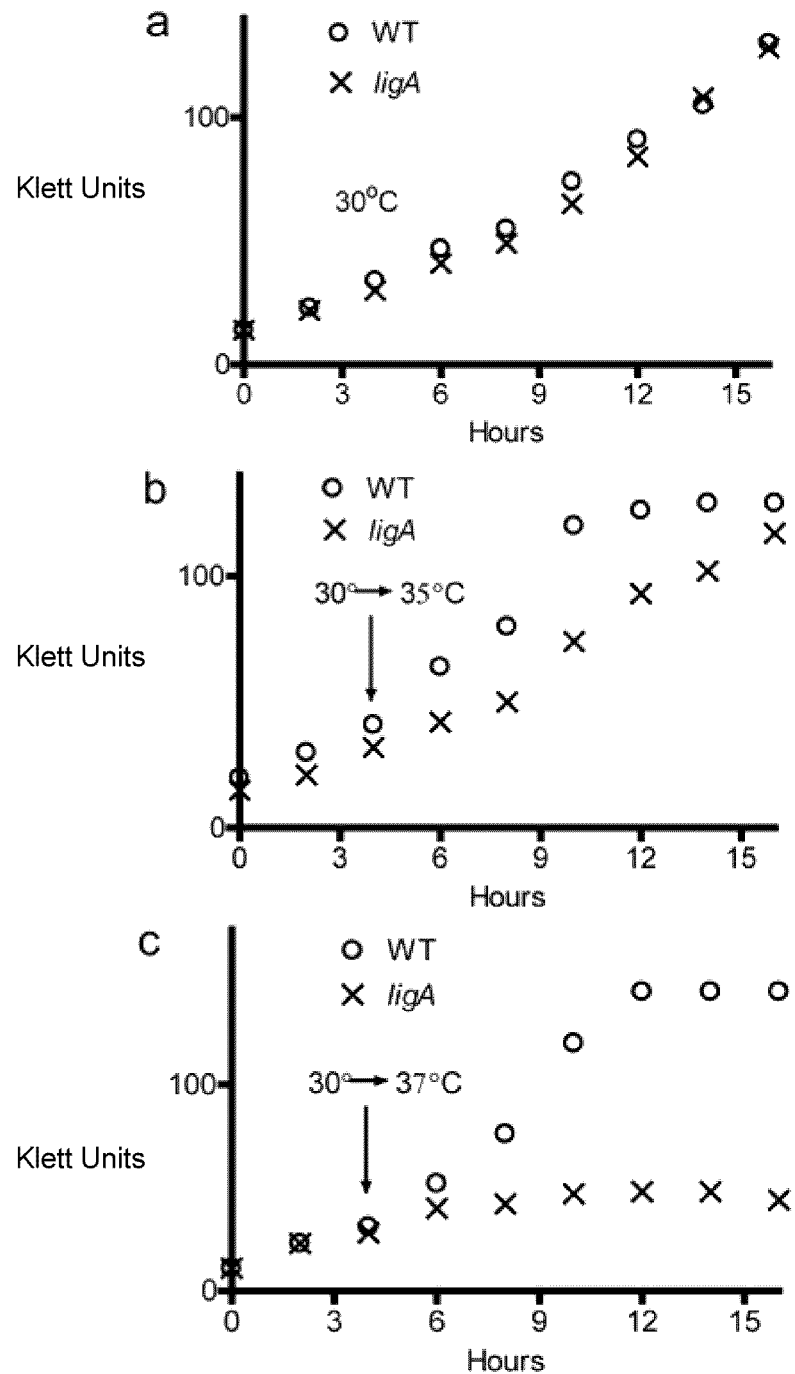
FIG. 9*a* is a graph illustrating the growth curve of wt *Mycobacterium smegmatis* and *M. smegmatis*-ligA$_{CP}$ at 30° C.
FIG. 9*b* is a graph illustrating the growth curve of *M. smegmatis*-ligA$_{CP}$ and wt *M. smegmatis* with a temperature shift from 30° C. to 35° C. after 4 hours.
FIG. 9*c* is a graph illustrating the growth curve of *M. smegmatis*-ligA$_{CP}$ and wt *M. smegmatis* with a temperature shift from 30° C. to 37° C. after 4 hours.
Figure 10:
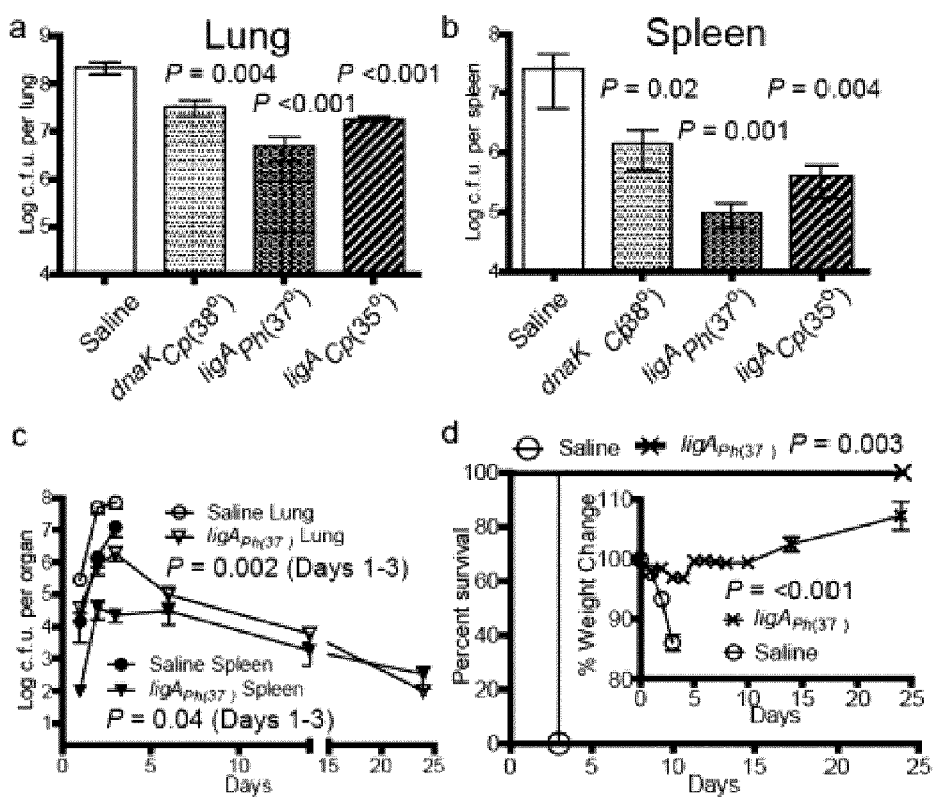
FIGS. 10*a*-10*d* are a series of graphs showing the protective immunity induced by TS *F. novicida* strains.

Another exemplary method pertains to an exemplary method the distribution of a Gram-negative pathogenic strain. A psychrophilic essential gene was introduced into *S. enterica*. Upon introduction of the ligA$_{Cp}$ psychrophilic essential gene into *S. enterica*, the result was a transgenic strain that was unable to grow at 37° C., as illustrated in FIG. 8. Furthermore, this strain was unable to disperse from the site of inoculation in infected mice, as evidenced by the inability of the strain to migrate to the lungs, liver or spleen.

EXAMPLE 9

This example pertains to an exemplary method to determine the level of protective immune response generated from the inoculation of a mammal with a TS transgenic bacterial strain. Methods of inoculation are known in the art, and can include i.v., i.m., s.c., or i.p injection, as well as inhalation, oral, and transdermal routes of delivery. One skilled in the art will appreciate that methods similar to those described in this example can be used to test any transgenic TS bacterial strain that includes one or more psychrophilic essential nucleic acid sequences.

Inoculation of mice with a TS *F. novicida* transgenic strain (Fn-ligA$_{Ph}$, Fn-ligA$_{Cp}$ or Fn-dnaK$_{Cp}$) caused the cells of their immune systems to be stimulated (as measured by reduced bacterial organ burdens) resulting in protection against infection with wt *F. novicida* (FIGS. 10*a-d*). Mice were initially inoculated with the TS transgenic strain and then challenged with an inoculation three weeks later of the wt *F. novicida* strain. This resulted in reduced growth in the livers and spleens of mice infected with the wt strains as compared to mice that had not been inoculated with recombinant *F. novicida*. Furthermore, decreases in the morbidity and mortalities were observed among the inoculated group of mice resulting in the conclusion that immune protection was achieved.

Similarly, mice vaccinated with *M. tuberculosis* and *S. enterica* transgenic strains (ligAPh) were shown to be more resistant to infections with the wt pathogens than were unvaccinated mice.

EXAMPLE 10

This example pertains to an exemplary method of discovering novel psychrophilic essential genes.

Psychrophilic bacterium can be isolated from a cold environment, for example ocean waters near the Earth's poles. Essential genes can be identified by using degenerate PCR or other standard techniques to find highly conserved genes, such as bacterial essential genes. Once these genes have been identified, they can be substituted into the genome of a mesophile using the methods provided herein or known in the art, displacing the host homologue of the gene. The resulting strain can then be tested for temperature sensitivity as described herein.

EXAMPLE 11

This example pertains to an exemplary method of using TS transgene strains in drug discovery research. Although a TS *F. tularensis* strain is exemplified, one skilled in the art will appreciate that similar methods can be used for other TS strains generated using the methods provided herein.

A TS transgenic strain of *F. tularensis* (ligA$_{Ph}$) that was inoperable above about 37° C. was used to infect cell line macrophages grown in microtiter plates at 34° C. A library of antimicrobial drug candidates was introduced to individual wells that contained the infected macrophages, and the effect of the drug candidates on the killing of *F. tularensis* was measured by lysing the macrophages at various time points and determining the number of viable TS transgenic *F. tularensis* by plating on agar plates. Wt *F. tularensis* is extremely infectious and causes a deadly disease. The use of the TS transgenic *F. tularensis* strain allowed one to use greatly relaxed biological containment conditions because the strain is incapable of causing disease in humans.

EXAMPLE 12

This example pertains to an exemplary method of generating and using TS strains of *Mycobacterium* containing temperature-sensitive essential nucleic acid molecules from psychrophilic bacteria to develop an immunogenic composition, which for example can be used to stimulate an immune response in a mammal, to protect or treat an *M. tuberculosis* infection in the mammal.

The ligA$_{Ph}$ and pryG$_{Cp}$ genes will separately be introduced into *M. tuberculosis* H37Rv using an integration/excision approach. The counter-selectable marker sacB will be used to enhance the generation of excision events that can be detected. C57BL/6 mice will be vaccinated by introducing 10,000 bacteria subcutaneously at the base of the tail. Negative controls mice injected with PBS and positive control mice injected with the BCG strain will processed at the same time. The mice will be rested for 30 days. Following this period all of the mice will be exposed to an aerosol of *M. tuberculosis* H37Rv that deposits 150 bacteria into the lungs. At weeks 0, 4, 8 16 and 32 following exposure to *M. tuberculosis* H37Rv, the mice will be euthanized and the number of *M. tuberculosis* H37Rv in the lungs and spleens determined. If the transgenes TS *M. tuberculosis* strains are successful at inducing a protective immune response, the number of bacteria in the mice organs will be less than that of the negative control. Subsequent experiments will be performed in a guinea pig model of tuberculosis.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

The invention claimed is:

1. A method of making a recombinant temperature sensitive (TS) bacteria comprising an essential peptide, comprising:

screening a psychrophilic microbial genome for detection therein of an essential polynucleotide that confers temperature sensitivity to a bacterium upon expression of a protein from the essential polynucleotide that is inactivated at a temperature greater than 30° C.;

isolating said essential polynucleotide;

constructing a nucleic acid construct comprising the essential polynucleotide and one or more control sequences operably linked to the essential polynucleotide;

inserting the nucleic acid construct into the genome of a selected mesophilic bacterial host cell thereby functionally replacing the selected mesophilic bacterial host cell's homologue of the essential polynucleotide whereby the essential polynucleotide encodes a protein that is operable at a temperature less than 30° C. and inoperable at a temperature greater than 30° C.;

culturing the mesophilic bacterial host cell comprising the essential polynucleotide at a temperature less than 30° C. to confirm the viability of the mesophilic bacterial host cell comprising the essential polynucleotide;

further culturing the mesophilic bacterial host cell comprising the essential polynucleotide at a temperature greater than 30° C. to determine if the mesophilic bacterial host cell comprising the essential polynucleotide is killed; and if the mesophilic bacterial host cell comprising the essential polynucleotide is killed, inserting the nucleic acid construct into the genome of a selected destination mesophilic bacterial host cell, thereby functionally replacing the selected destination mesophilic bacterial host cell's homologue of the essential polynucleotide, thereby generating a recombinant TS bacteria.

2. The method of claim 1, wherein the selected mesophilic bacterial host cell is a *Francisella novicida* cell.

3. The method of claim 1, wherein the wherein the psychrophilic microbial genome is from *Colwellia* sp., *Pseudoalteromonas* sp., or *Shewanella* sp.

4. The method of claim 1, wherein the psychrophilic microbial genome is from *Pseudoalteromonas haloplanktis.*

5. The method of claim 1, wherein the psychrophilic microbial genome is from *C. psychrerhraea.*

6. The method of claim 1, wherein the selected destination mesophilic bacterial host cell is *Salmonella* sp. or *Mycobacterium* sp.

7. The method of claim 1, wherein the selected destination mesophilic bacterial host cell is *Haemophilus* sp., *Vibrio* sp., *Escherichia* sp., *Streptococcus* sp., *Burkholderia* sp., *Campylobacter* sp., *Neisseria* sp., *Helicobacter* sp. or *Francisella* sp.

8. The method of claim 1, wherein screening the psychrophilic microbial genome detects a polynucleotide sequence comprising the nucleotide sequence shown in SEQ ID NO: 1, 3, 5, 7, 9, 11, 13, 15, 17, 19, 21, 23, 25 or 27.

9. The method of claim 1, wherein screening the psychrophilic microbial genome detects a polynucleotide sequence encoding a protein comprising the amino acid sequence shown in SEQ ID NO: 2, 4, 6, 8, 10, 12, 14, 16, 18, 20, 22, 24, 26, or 28.

10. The method of claim 1, wherein the protein encoded by the essential polynucleotide is operable at a temperature of 4° C. to 30° C.

11. The method of claim 1, wherein the nucleic acid construct comprising the essential polynucleotide comprises a vector.

12. The method of claim 1, wherein screening the psychrophilic microbial genome detects a polynucleotide sequence selected from the group consisting of ligA, pyrG, hemC, ftsZ, cmk, murG, fmt, tyrS, or dnaK.

13. The method of claim 1, wherein screening the psychrophilic microbial genome detects a polynucleotide sequence comprising the ligA polynucleotide sequence.

* * * * *

SEQUENCE LISTING

```
<160> NUMBER OF SEQ ID NOS: 28

<210> SEQ ID NO 1
<211> LENGTH: 2070
<212> TYPE: DNA
<213> ORGANISM: Artificial Sequence
<220> FEATURE:
<223> OTHER INFORMATION: ligACp hybrid
<220> FEATURE:
<221> NAME/KEY: CDS
<222> LOCATION: (1)..(2070)
<220> FEATURE:
<221> NAME/KEY: misc_feature
<222> LOCATION: (569)..(569)
<223> OTHER INFORMATION: k at location 569 is g or t/u
<220> FEATURE:
<221> NAME/KEY: misc_feature
<222> LOCATION: (1460)..(1460)
<223> OTHER INFORMATION: y at location 1460 is t/u or c

<400> SEQUENCE: 1 atg act cca gtc gaa aag aaa att agc caa ctg caa cag cag ctt aat        48
Met Thr Pro Val Glu Lys Lys Ile Ser Gln Leu Gln Gln Gln Leu Asn
1               5                   10                  15 caa tat aat cat gaa tat tat gta tta gac caa cct agt gtg cct gat        96
Gln Tyr Asn His Glu Tyr Tyr Val Leu Asp Gln Pro Ser Val Pro Asp
            20                  25                  30 gca gaa tat gac cga tta atg aca gca tta atc gat tta gaa aag act       144
Ala Glu Tyr Asp Arg Leu Met Thr Ala Leu Ile Asp Leu Glu Lys Thr
        35                  40                  45 aat cct gag ctt aag act att gac tca cct agc caa aaa gtt ggc ggt       192
Asn Pro Glu Leu Lys Thr Ile Asp Ser Pro Ser Gln Lys Val Gly Gly
    50                  55                  60 cag gca tta aaa tct ttc act caa gta act cat cag ctg ccg atg ctt       240
Gln Ala Leu Lys Ser Phe Thr Gln Val Thr His Gln Leu Pro Met Leu
65                  70                  75                  80 tct ctt gat aat gtt ttt tct tta gat gat ttt cac gca ttt gtt aaa       288
Ser Leu Asp Asn Val Phe Ser Leu Asp Asp Phe His Ala Phe Val Lys
                85                  90                  95 cgc gta aaa gat agg tta aat gac aat caa gcg ata gtc ttt tgt gcc       336
Arg Val Lys Asp Arg Leu Asn Asp Asn Gln Ala Ile Val Phe Cys Ala
            100                 105                 110 gag cct aaa tta gac ggt tta gca gtg agt tta cgt tat gag cac ggg       384
Glu Pro Lys Leu Asp Gly Leu Ala Val Ser Leu Arg Tyr Glu His Gly
        115                 120                 125 cag tta ata caa gcg gct aca cgt ggc gat ggt agt gta ggg gag aat       432
Gln Leu Ile Gln Ala Ala Thr Arg Gly Asp Gly Ser Val Gly Glu Asn
    130                 135                 140 att acg act aac att cgt aca ata aaa tct att ccg ctt aag tta atg       480
Ile Thr Thr Asn Ile Arg Thr Ile Lys Ser Ile Pro Leu Lys Leu Met
145                 150                 155                 160 ggc aca cca ggt aaa gat ttt cct gat atc gtt gaa gtc cgc ggt gaa       528
```

```
Gly Thr Pro Gly Lys Asp Phe Pro Asp Ile Val Glu Val Arg Gly Glu
            165                 170                 175 gtt ttt atg cct aag gca agt ttt gac gca tta aat aca tkg gct aaa        576
Val Phe Met Pro Lys Ala Ser Phe Asp Ala Leu Asn Thr Xaa Ala Lys
        180                 185                 190 aaa cgt ggc gag aaa ggt ttt gca aat cca cgt aat gca gcg gcg gga        624
Lys Arg Gly Glu Lys Gly Phe Ala Asn Pro Arg Asn Ala Ala Ala Gly
            195                 200                 205 agt tta cga caa ctt gat tct aaa atc acc gct aaa cgt aat tta gct        672
Ser Leu Arg Gln Leu Asp Ser Lys Ile Thr Ala Lys Arg Asn Leu Ala
        210                 215                 220 ttt tac gct tat agc ctt gga ttt gta ggg aaa ctg tct gat gga ggc        720
Phe Tyr Ala Tyr Ser Leu Gly Phe Val Gly Lys Leu Ser Asp Gly Gly
225                 230                 235                 240 gct gaa agt acc gat tta acc aat gac ttt ttt gct aac tct cat cat        768
Ala Glu Ser Thr Asp Leu Thr Asn Asp Phe Phe Ala Asn Ser His His
            245                 250                 255 gaa aga cta tgt cag ctt aaa agg ttg ggt ttg cct atg tgt cca gaa        816
Glu Arg Leu Cys Gln Leu Lys Arg Leu Gly Leu Pro Met Cys Pro Glu
        260                 265                 270 gta cgc tta ctt gaa agt gag caa gcc tgt gat gcg ttt tat caa gat        864
Val Arg Leu Leu Glu Ser Glu Gln Ala Cys Asp Ala Phe Tyr Gln Asp
            275                 280                 285 atc tta gca aag cgt agt gcc ttg agt tat gaa att gat ggc act gta        912
Ile Leu Ala Lys Arg Ser Ala Leu Ser Tyr Glu Ile Asp Gly Thr Val
        290                 295                 300 tta aaa gtt gat gaa atc tct ttg cag aaa cgt tta ggg ttt gtc gca        960
Leu Lys Val Asp Glu Ile Ser Leu Gln Lys Arg Leu Gly Phe Val Ala
305                 310                 315                 320 cgt gcc cca cgt tgg gct att gct tat aaa ttc cct gcg gaa gaa gaa       1008
Arg Ala Pro Arg Trp Ala Ile Ala Tyr Lys Phe Pro Ala Glu Glu Glu
            325                 330                 335 tta acc tgt gtt gaa gat gtc gag ttt caa gta ggg cgt acc ggc gcg       1056
Leu Thr Cys Val Glu Asp Val Glu Phe Gln Val Gly Arg Thr Gly Ala
        340                 345                 350 att act ccc gta gca cgt ttg aaa ccg gta ttt gtt ggt ggc gta aca       1104
Ile Thr Pro Val Ala Arg Leu Lys Pro Val Phe Val Gly Gly Val Thr
            355                 360                 365 gtt tct aat gcc aca tta cat aac caa gat gaa ata acc cga tta ggg       1152
Val Ser Asn Ala Thr Leu His Asn Gln Asp Glu Ile Thr Arg Leu Gly
        370                 375                 380 ctg aaa gtg aat gat ttc gtg gtt atc cgc cgt gcc ggt gat gtt att       1200
Leu Lys Val Asn Asp Phe Val Val Ile Arg Arg Ala Gly Asp Val Ile
385                 390                 395                 400 cct caa att gtt agc gta gta ctt gat aaa cga cca gat aat gcc gtc       1248
Pro Gln Ile Val Ser Val Val Leu Asp Lys Arg Pro Asp Asn Ala Val
            405                 410                 415 gat ata gtc ttt cct acc agt tgc cct gtt tgt gac tct gca gtg gct       1296
Asp Ile Val Phe Pro Thr Ser Cys Pro Val Cys Asp Ser Ala Val Ala
        420                 425                 430 aaa cct gaa ggt gaa gcc gta ctg aga tgt acc gcc gga ctt ttc tgt       1344
Lys Pro Glu Gly Glu Ala Val Leu Arg Cys Thr Ala Gly Leu Phe Cys
            435                 440                 445 gcg gcg caa aga aaa gaa gct att aaa cat ttt gct tct cga aaa gca       1392
Ala Ala Gln Arg Lys Glu Ala Ile Lys His Phe Ala Ser Arg Lys Ala
        450                 455                 460 cat gat gtt gat ggt tta ggt gac aaa cta gta gag caa ctt gta gat       1440
His Asp Val Asp Gly Leu Gly Asp Lys Leu Val Glu Gln Leu Val Asp
465                 470                 475                 480
```

-continued

| | | |
|---|---|---|
| gaa aag tta att aat acg cyc gct gat tta ttc aaa tta acc gaa ata<br>Glu Lys Leu Ile Asn Thr Xaa Ala Asp Leu Phe Lys Leu Thr Glu Ile<br>                         485              490              495 | 1488 |
| caa gtt agt act ata gat cgt atg ggt aaa aaa tca gcg acc aat tta<br>Gln Val Ser Thr Ile Asp Arg Met Gly Lys Lys Ser Ala Thr Asn Leu<br>           500                    505              510 | 1536 |
| att aat gga ctt gag cag gct aaa agt acc aca cta gca aaa ttt att<br>Ile Asn Gly Leu Glu Gln Ala Lys Ser Thr Thr Leu Ala Lys Phe Ile<br>       515                    520              525 | 1584 |
| tat ggt ctg ggc ata cgc gaa gtc ggt gaa gca act gct gct aat cta<br>Tyr Gly Leu Gly Ile Arg Glu Val Gly Glu Ala Thr Ala Ala Asn Leu<br>530                    535              540 | 1632 |
| gca aat cat ttt tat acc tta gcg gca att gaa agt gct tct ctt gaa<br>Ala Asn His Phe Tyr Thr Leu Ala Ala Ile Glu Ser Ala Ser Leu Glu<br>545              550                555              560 | 1680 |
| gac tta caa aat gtt tca gat gtt ggc gaa gtc gtt gcc aaa aat att<br>Asp Leu Gln Asn Val Ser Asp Val Gly Glu Val Val Ala Lys Asn Ile<br>                         565              570              575 | 1728 |
| att aat ttc ttt aaa gaa gag cat aac tta gcg atc gtt tct gga cta<br>Ile Asn Phe Phe Lys Glu Glu His Asn Leu Ala Ile Val Ser Gly Leu<br>           580                    585              590 | 1776 |
| agt gaa gta atg cac tgg cca act att gaa ata aag tca gct gag gag<br>Ser Glu Val Met His Trp Pro Thr Ile Glu Ile Lys Ser Ala Glu Glu<br>       595                    600              605 | 1824 |
| tta ccg ctt gca gag cag ata ttt gtt tta aca ggc aca tta acc caa<br>Leu Pro Leu Ala Glu Gln Ile Phe Val Leu Thr Gly Thr Leu Thr Gln<br>610                    615              620 | 1872 |
| atg gga aga act gaa gct aaa aca gcc tta cag tcc ttg gga gct aaa<br>Met Gly Arg Thr Glu Ala Lys Thr Ala Leu Gln Ser Leu Gly Ala Lys<br>625              630                635              640 | 1920 |
| gta tca ggt agt gtc tcg aag aat aca cac ttc gtt gtt gca ggt gat<br>Val Ser Gly Ser Val Ser Lys Asn Thr His Phe Val Val Ala Gly Asp<br>                         645              650              655 | 1968 |
| aaa gcg gga tct aaa ctg act aag gct cag gat tta ggt atc tca gtg<br>Lys Ala Gly Ser Lys Leu Thr Lys Ala Gln Asp Leu Gly Ile Ser Val<br>           660                    665              670 | 2016 |
| ctt acc gaa gat ggg tta gta gcg tta ctt gcc gaa cat ggc ata act<br>Leu Thr Glu Asp Gly Leu Val Ala Leu Leu Ala Glu His Gly Ile Thr<br>       675                    680              685 | 2064 |
| att tga<br>Ile | 2070 |

<210> SEQ ID NO 2
<211> LENGTH: 689
<212> TYPE: PRT
<213> ORGANISM: Artificial Sequence
<220> FEATURE:
<221> NAME/KEY: misc_feature
<222> LOCATION: (190)..(190)
<223> OTHER INFORMATION: The 'Xaa' at location 190 stands for Trp, or
     Leu.
<220> FEATURE:
<221> NAME/KEY: misc_feature
<222> LOCATION: (487)..(487)
<223> OTHER INFORMATION: The 'Xaa' at location 487 stands for Pro, or
     Leu.
<220> FEATURE:
<223> OTHER INFORMATION: Synthetic Construct

<400> SEQUENCE: 2

Met Thr Pro Val Glu Lys Lys Ile Ser Gln Leu Gln Gln Gln Leu Asn
1               5                   10                  15

Gln Tyr Asn His Glu Tyr Tyr Val Leu Asp Gln Pro Ser Val Pro Asp

-continued

```
                20                  25                  30
Ala Glu Tyr Asp Arg Leu Met Thr Ala Leu Ile Asp Leu Glu Lys Thr
             35                  40                  45
Asn Pro Glu Leu Lys Thr Ile Asp Ser Pro Ser Gln Lys Val Gly Gly
         50                  55                  60
Gln Ala Leu Lys Ser Phe Thr Gln Val Thr His Gln Leu Pro Met Leu
 65                  70                  75                  80
Ser Leu Asp Asn Val Phe Ser Leu Asp Asp Phe His Ala Phe Val Lys
                 85                  90                  95
Arg Val Lys Asp Arg Leu Asn Asp Asn Gln Ala Ile Val Phe Cys Ala
            100                 105                 110
Glu Pro Lys Leu Asp Gly Leu Ala Val Ser Leu Arg Tyr Glu His Gly
        115                 120                 125
Gln Leu Ile Gln Ala Ala Thr Arg Gly Asp Gly Ser Val Gly Glu Asn
    130                 135                 140
Ile Thr Thr Asn Ile Arg Thr Ile Lys Ser Ile Pro Leu Lys Leu Met
145                 150                 155                 160
Gly Thr Pro Gly Lys Asp Phe Pro Asp Ile Val Glu Val Arg Gly Glu
                165                 170                 175
Val Phe Met Pro Lys Ala Ser Phe Asp Ala Leu Asn Thr Xaa Ala Lys
            180                 185                 190
Lys Arg Gly Glu Lys Gly Phe Ala Asn Pro Arg Asn Ala Ala Ala Gly
        195                 200                 205
Ser Leu Arg Gln Leu Asp Ser Lys Ile Thr Ala Lys Arg Asn Leu Ala
    210                 215                 220
Phe Tyr Ala Tyr Ser Leu Gly Phe Val Gly Lys Leu Ser Asp Gly Gly
225                 230                 235                 240
Ala Glu Ser Thr Asp Leu Thr Asn Asp Phe Phe Ala Asn Ser His His
                245                 250                 255
Glu Arg Leu Cys Gln Leu Lys Arg Leu Gly Leu Pro Met Cys Pro Glu
            260                 265                 270
Val Arg Leu Leu Glu Ser Glu Gln Ala Cys Asp Ala Phe Tyr Gln Asp
        275                 280                 285
Ile Leu Ala Lys Arg Ser Ala Leu Ser Tyr Glu Ile Asp Gly Thr Val
    290                 295                 300
Leu Lys Val Asp Glu Ile Ser Leu Gln Lys Arg Leu Gly Phe Val Ala
305                 310                 315                 320
Arg Ala Pro Arg Trp Ala Ile Ala Tyr Lys Phe Pro Ala Glu Glu Glu
                325                 330                 335
Leu Thr Cys Val Glu Asp Val Glu Phe Gln Val Gly Arg Thr Gly Ala
            340                 345                 350
Ile Thr Pro Val Ala Arg Leu Lys Pro Val Phe Val Gly Gly Val Thr
        355                 360                 365
Val Ser Asn Ala Thr Leu His Asn Gln Asp Glu Ile Thr Arg Leu Gly
    370                 375                 380
Leu Lys Val Asn Asp Phe Val Val Ile Arg Arg Ala Gly Asp Val Ile
385                 390                 395                 400
Pro Gln Ile Val Ser Val Leu Asp Lys Arg Pro Asp Asn Ala Val
            405                 410                 415
Asp Ile Val Phe Pro Thr Ser Cys Pro Val Cys Asp Ser Ala Val Ala
            420                 425                 430
Lys Pro Glu Gly Glu Ala Val Leu Arg Cys Thr Ala Gly Leu Phe Cys
        435                 440                 445
```

```
Ala Ala Gln Arg Lys Glu Ala Ile Lys His Phe Ala Ser Arg Lys Ala
    450                 455                 460
His Asp Val Asp Gly Leu Gly Asp Lys Leu Val Glu Gln Leu Val Asp
465                 470                 475                 480
Glu Lys Leu Ile Asn Thr Xaa Ala Asp Leu Phe Lys Leu Thr Glu Ile
                485                 490                 495
Gln Val Ser Thr Ile Asp Arg Met Gly Lys Lys Ser Ala Thr Asn Leu
            500                 505                 510
Ile Asn Gly Leu Glu Gln Ala Lys Ser Thr Thr Leu Ala Lys Phe Ile
        515                 520                 525
Tyr Gly Leu Gly Ile Arg Glu Val Gly Glu Ala Thr Ala Ala Asn Leu
    530                 535                 540
Ala Asn His Phe Tyr Thr Leu Ala Ala Ile Glu Ser Ala Ser Leu Glu
545                 550                 555                 560
Asp Leu Gln Asn Val Ser Asp Val Gly Glu Val Val Ala Lys Asn Ile
                565                 570                 575
Ile Asn Phe Phe Lys Glu Glu His Asn Leu Ala Ile Val Ser Gly Leu
            580                 585                 590
Ser Glu Val Met His Trp Pro Thr Ile Glu Ile Lys Ser Ala Glu Glu
        595                 600                 605
Leu Pro Leu Ala Glu Gln Ile Phe Val Leu Thr Gly Thr Leu Thr Gln
    610                 615                 620
Met Gly Arg Thr Glu Ala Lys Thr Ala Leu Gln Ser Leu Gly Ala Lys
625                 630                 635                 640
Val Ser Gly Ser Val Ser Lys Asn Thr His Phe Val Val Ala Gly Asp
                645                 650                 655
Lys Ala Gly Ser Lys Leu Thr Lys Ala Gln Asp Leu Gly Ile Ser Val
            660                 665                 670
Leu Thr Glu Asp Gly Leu Val Ala Leu Leu Ala Glu His Gly Ile Thr
        675                 680                 685
Ile

<210> SEQ ID NO 3
<211> LENGTH: 2022
<212> TYPE: DNA
<213> ORGANISM: Artificial Sequence
<220> FEATURE:
<223> OTHER INFORMATION: ligAPh hybrid
<220> FEATURE:
<221> NAME/KEY: CDS
<222> LOCATION: (1)..(2022)

<400> SEQUENCE: 3
```

| | | | | | | | | | | | | | | | | |
|---|---|---|---|---|---|---|---|---|---|---|---|---|---|---|---|---|
| atg | act | cca | agc | att | agt | gag | caa | ata | aac | cat | ctt | cgt | agt | acg | ctt | 48 |
| Met | Thr | Pro | Ser | Ile | Ser | Glu | Gln | Ile | Asn | His | Leu | Arg | Ser | Thr | Leu | |
| 1 | | | | 5 | | | | | 10 | | | | | 15 | | |
| gaa | cag | cac | agt | tac | aat | tat | tat | gta | ctt | gat | acc | ccc | agt | att | cct | 96 |
| Glu | Gln | His | Ser | Tyr | Asn | Tyr | Tyr | Val | Leu | Asp | Thr | Pro | Ser | Ile | Pro | |
| | | | 20 | | | | | 25 | | | | | 30 | | | |
| gat | gct | gaa | tac | gac | cgt | tta | tta | caa | caa | ctc | agc | gca | cta | gaa | act | 144 |
| Asp | Ala | Glu | Tyr | Asp | Arg | Leu | Leu | Gln | Gln | Leu | Ser | Ala | Leu | Glu | Thr | |
| | | 35 | | | | | 40 | | | | | 45 | | | | |
| cag | cac | cca | gaa | tta | ata | act | gcc | gac | tca | cca | acc | caa | aaa | gtg | ggc | 192 |
| Gln | His | Pro | Glu | Leu | Ile | Thr | Ala | Asp | Ser | Pro | Thr | Gln | Lys | Val | Gly | |
| | 50 | | | | | 55 | | | | | 60 | | | | | |
| ggt | gct | gcg | cta | agt | aaa | ttt | gag | caa | gta | gcg | cac | caa | gtg | cct | atg | 240 |
| Gly | Ala | Ala | Leu | Ser | Lys | Phe | Glu | Gln | Val | Ala | His | Gln | Val | Pro | Met | |

|  |  |  |  |  |  |  |  | 65 |  |  |  |  | 70 |  |  |  |  | 75 |  |  |  |  | 80 |  |  |
|---|---|---|---|---|---|---|---|---|---|---|---|---|---|---|---|---|---|---|---|---|---|---|---|---|---|

```
tta tcg ctt gat aac gcc ttt agc gaa gat gag ttt att gcc ttt aat       288
Leu Ser Leu Asp Asn Ala Phe Ser Glu Asp Glu Phe Ile Ala Phe Asn
                85                  90                  95 cgc cgt ata aaa gag cgt tta atg agt acc gaa gag ctt act ttt tgt       336
Arg Arg Ile Lys Glu Arg Leu Met Ser Thr Glu Glu Leu Thr Phe Cys
            100                 105                 110 tgt gag cca aaa cta gat ggc tta gct gtg tcg att att tat cgt gat       384
Cys Glu Pro Lys Leu Asp Gly Leu Ala Val Ser Ile Ile Tyr Arg Asp
        115                 120                 125 ggc gta cta gtg caa gcc gcg acc cga ggt gat ggg ttg acg gga gaa       432
Gly Val Leu Val Gln Ala Ala Thr Arg Gly Asp Gly Leu Thr Gly Glu
    130                 135                 140 aat gta act caa aac gtt aaa aca att cgt aat gtg cca ctt aaa tta       480
Asn Val Thr Gln Asn Val Lys Thr Ile Arg Asn Val Pro Leu Lys Leu
145                 150                 155                 160 cga ggt agc gat tat cct gct gaa cta gaa gtg cgc ggc gaa gtg ttt       528
Arg Gly Ser Asp Tyr Pro Ala Glu Leu Glu Val Arg Gly Glu Val Phe
                165                 170                 175 atg gat aat gca ggc ttt gaa aag ttt aac att gaa gct gaa aaa cgt       576
Met Asp Asn Ala Gly Phe Glu Lys Phe Asn Ile Glu Ala Glu Lys Arg
            180                 185                 190 ggt gaa aaa gta ttt gta aac cca cgc aac gcc gcc gca ggt agc ctg       624
Gly Glu Lys Val Phe Val Asn Pro Arg Asn Ala Ala Ala Gly Ser Leu
        195                 200                 205 cgc cag ctt gac tct aaa att acg gct aaa cgc cca ctg atg ttt tat       672
Arg Gln Leu Asp Ser Lys Ile Thr Ala Lys Arg Pro Leu Met Phe Tyr
    210                 215                 220 gcc tac agc aca ggt ctt gta gcc gac ggt agc att gca gag gat cat       720
Ala Tyr Ser Thr Gly Leu Val Ala Asp Gly Ser Ile Ala Glu Asp His
225                 230                 235                 240 tat cag caa tta gaa aaa ttg act gat tgg ggg tta cca ctt tgc cct       768
Tyr Gln Gln Leu Glu Lys Leu Thr Asp Trp Gly Leu Pro Leu Cys Pro
                245                 250                 255 gaa aca aaa tta gta gaa ggc cca caa gct gca ctg gct tat tat act       816
Glu Thr Lys Leu Val Glu Gly Pro Gln Ala Ala Leu Ala Tyr Tyr Thr
            260                 265                 270 gac att tta acg cgc cgt ggc gag ctt aaa tat gaa ata gat ggc gtg       864
Asp Ile Leu Thr Arg Arg Gly Glu Leu Lys Tyr Glu Ile Asp Gly Val
        275                 280                 285 gta ata aaa ata aat caa aaa gcc tta caa gag cgt tta ggc ttt gta       912
Val Ile Lys Ile Asn Gln Lys Ala Leu Gln Glu Arg Leu Gly Phe Val
    290                 295                 300 gca cgc gct ccg cgt tgg gct att gct tat aag ttc ccg gcc caa gaa       960
Ala Arg Ala Pro Arg Trp Ala Ile Ala Tyr Lys Phe Pro Ala Gln Glu
305                 310                 315                 320 gaa ata acc aaa tta ctc gat gta gag ttt cag gtg ggg cgt acg gga      1008
Glu Ile Thr Lys Leu Leu Asp Val Glu Phe Gln Val Gly Arg Thr Gly
                325                 330                 335 gca att aca ccg gtt gca cgc tta gag ccg gta ttt gtt ggt ggt gtt      1056
Ala Ile Thr Pro Val Ala Arg Leu Glu Pro Val Phe Val Gly Gly Val
            340                 345                 350 act gta tca aac gct acc ttg cac aat ggc gat gaa ata gcg cgc tta      1104
Thr Val Ser Asn Ala Thr Leu His Asn Gly Asp Glu Ile Ala Arg Leu
        355                 360                 365 ggc gta aaa gtg ggc gac acg gta att att cgc cgt gca ggg gac gta      1152
Gly Val Lys Val Gly Asp Thr Val Ile Ile Arg Arg Ala Gly Asp Val
    370                 375                 380 att cca caa ata acg caa gta gta ctt gag cgc cgc cct gat gat gcc      1200
```

```
Ile Pro Gln Ile Thr Gln Val Val Leu Glu Arg Arg Pro Asp Asp Ala
385                 390                 395                 400 cgc gat att gag ttt ccg gta act tgc cca att tgt gac tcc cat gta      1248
Arg Asp Ile Glu Phe Pro Val Thr Cys Pro Ile Cys Asp Ser His Val
                405                 410                 415 gaa aaa gta gaa ggt gaa gcc gta gcg cgt tgt act ggt ggt tta gtg      1296
Glu Lys Val Glu Gly Glu Ala Val Ala Arg Cys Thr Gly Gly Leu Val
            420                 425                 430 tgc ccg gcg caa cgt aaa caa gcg att aaa cac ttt gca tcg cgc aaa      1344
Cys Pro Ala Gln Arg Lys Gln Ala Ile Lys His Phe Ala Ser Arg Lys
        435                 440                 445 gca ctc gat att gac ggc ctt ggc gat aaa att gtt gat caa ctc gtc      1392
Ala Leu Asp Ile Asp Gly Leu Gly Asp Lys Ile Val Asp Gln Leu Val
    450                 455                 460 gac aga gag ctg att aaa acc cct gca gat ttg ttt att tta aag caa      1440
Asp Arg Glu Leu Ile Lys Thr Pro Ala Asp Leu Phe Ile Leu Lys Gln
465                 470                 475                 480 gga cat ttt gaa tcg ctt gag cgt atg ggg cca aag tcg gct aaa aat      1488
Gly His Phe Glu Ser Leu Glu Arg Met Gly Pro Lys Ser Ala Lys Asn
                485                 490                 495 ttg gtt act gcg ctt caa gac gct aaa gca aca act ttg gct aag ttt      1536
Leu Val Thr Ala Leu Gln Asp Ala Lys Ala Thr Thr Leu Ala Lys Phe
            500                 505                 510 tta tac tca ttg ggt att cgt gaa gcg ggt gag gca acc aca caa aat      1584
Leu Tyr Ser Leu Gly Ile Arg Glu Ala Gly Glu Ala Thr Thr Gln Asn
        515                 520                 525 tta gct aat cat ttc tta acc ctt gaa aac gta ata aat gcc agc att      1632
Leu Ala Asn His Phe Leu Thr Leu Glu Asn Val Ile Asn Ala Ser Ile
    530                 535                 540 gat agt tta act caa gta agt gat gtg ggc gaa ata gta gca acc cat      1680
Asp Ser Leu Thr Gln Val Ser Asp Val Gly Glu Ile Val Ala Thr His
545                 550                 555                 560 gta cgt agc ttt ttt gcc gaa cag cat aat tta gat gtt gta aat gcg      1728
Val Arg Ser Phe Phe Ala Glu Gln His Asn Leu Asp Val Val Asn Ala
                565                 570                 575 ctg gta gag caa ggt att aat tgg cct gaa ctt act cca cct tca gcg      1776
Leu Val Glu Gln Gly Ile Asn Trp Pro Glu Leu Thr Pro Pro Ser Ala
            580                 585                 590 caa gag cag cca tta gct ggc ctt gtt tat gtg ctt acc ggt acc tta      1824
Gln Glu Gln Pro Leu Ala Gly Leu Val Tyr Val Leu Thr Gly Thr Leu
        595                 600                 605 aac aca tta aac cgt aat gac gcc aaa gca cgt ttg caa cag tta ggt      1872
Asn Thr Leu Asn Arg Asn Asp Ala Lys Ala Arg Leu Gln Gln Leu Gly
    610                 615                 620 gct aaa gtg tcg ggt agt gtg tcg gct aaa acc gat gcg tta gta gca      1920
Ala Lys Val Ser Gly Ser Val Ser Ala Lys Thr Asp Ala Leu Val Ala
625                 630                 635                 640 ggc gaa aag gcc ggc tct aaa cta act aag gca caa gac tta ggt ata      1968
Gly Glu Lys Ala Gly Ser Lys Leu Thr Lys Ala Gln Asp Leu Gly Ile
                645                 650                 655 gat gta ctg aca gaa gaa gat tta att aat tta tta gag caa cat aat      2016
Asp Val Leu Thr Glu Glu Asp Leu Ile Asn Leu Leu Glu Gln His Asn
            660                 665                 670 ggc tga                                                              2022
Gly

<210> SEQ ID NO 4
<211> LENGTH: 673
<212> TYPE: PRT
<213> ORGANISM: Artificial Sequence
```

```
<220> FEATURE:
<223> OTHER INFORMATION: Synthetic Construct

<400> SEQUENCE: 4

Met Thr Pro Ser Ile Ser Glu Gln Ile Asn His Leu Arg Ser Thr Leu
1               5                   10                  15

Glu Gln His Ser Tyr Asn Tyr Val Leu Asp Thr Pro Ser Ile Pro
            20                  25                  30

Asp Ala Glu Tyr Asp Arg Leu Leu Gln Gln Leu Ser Ala Leu Glu Thr
            35                  40                  45

Gln His Pro Glu Leu Ile Thr Ala Asp Ser Pro Thr Gln Lys Val Gly
        50                  55                  60

Gly Ala Ala Leu Ser Lys Phe Glu Gln Val Ala His Gln Val Pro Met
65                  70                  75                  80

Leu Ser Leu Asp Asn Ala Phe Ser Glu Asp Phe Ile Ala Phe Asn
                85                  90                  95

Arg Arg Ile Lys Glu Arg Leu Met Ser Thr Glu Glu Leu Thr Phe Cys
            100                 105                 110

Cys Glu Pro Lys Leu Asp Gly Leu Ala Val Ser Ile Ile Tyr Arg Asp
            115                 120                 125

Gly Val Leu Val Gln Ala Ala Thr Arg Gly Asp Gly Leu Thr Gly Glu
        130                 135                 140

Asn Val Thr Gln Asn Val Lys Thr Ile Arg Asn Val Pro Leu Lys Leu
145                 150                 155                 160

Arg Gly Ser Asp Tyr Pro Ala Glu Leu Glu Val Arg Gly Glu Val Phe
                165                 170                 175

Met Asp Asn Ala Gly Phe Glu Lys Phe Asn Ile Glu Ala Glu Lys Arg
            180                 185                 190

Gly Glu Lys Val Phe Val Asn Pro Arg Asn Ala Ala Ala Gly Ser Leu
        195                 200                 205

Arg Gln Leu Asp Ser Lys Ile Thr Ala Lys Arg Pro Leu Met Phe Tyr
210                 215                 220

Ala Tyr Ser Thr Gly Leu Val Ala Asp Gly Ser Ile Ala Glu Asp His
225                 230                 235                 240

Tyr Gln Gln Leu Glu Lys Leu Thr Asp Trp Gly Leu Pro Leu Cys Pro
                245                 250                 255

Glu Thr Lys Leu Val Glu Gly Pro Gln Ala Ala Leu Ala Tyr Tyr Thr
            260                 265                 270

Asp Ile Leu Thr Arg Arg Gly Glu Leu Lys Tyr Glu Ile Asp Gly Val
        275                 280                 285

Val Ile Lys Ile Asn Gln Lys Ala Leu Gln Glu Arg Leu Gly Phe Val
290                 295                 300

Ala Arg Ala Pro Arg Trp Ala Ile Ala Tyr Lys Phe Pro Ala Gln Glu
305                 310                 315                 320

Glu Ile Thr Lys Leu Leu Asp Val Glu Phe Gln Val Gly Arg Thr Gly
                325                 330                 335

Ala Ile Thr Pro Val Ala Arg Leu Glu Pro Val Phe Val Gly Gly Val
            340                 345                 350

Thr Val Ser Asn Ala Thr Leu His Asn Gly Asp Glu Ile Ala Arg Leu
        355                 360                 365

Gly Val Lys Val Gly Asp Thr Val Ile Ile Arg Arg Ala Gly Asp Val
370                 375                 380

Ile Pro Gln Ile Thr Gln Val Val Leu Glu Arg Arg Pro Asp Asp Ala
385                 390                 395                 400
```

```
Arg Asp Ile Glu Phe Pro Val Thr Cys Pro Ile Cys Asp Ser His Val
                405                 410                 415

Glu Lys Val Glu Gly Glu Ala Val Ala Arg Cys Thr Gly Gly Leu Val
            420                 425                 430

Cys Pro Ala Gln Arg Lys Gln Ala Ile Lys His Phe Ala Ser Arg Lys
        435                 440                 445

Ala Leu Asp Ile Asp Gly Leu Gly Asp Lys Ile Val Asp Gln Leu Val
    450                 455                 460

Asp Arg Glu Leu Ile Lys Thr Pro Ala Asp Leu Phe Ile Leu Lys Gln
465                 470                 475                 480

Gly His Phe Glu Ser Leu Glu Arg Met Gly Pro Lys Ser Ala Lys Asn
                485                 490                 495

Leu Val Thr Ala Leu Gln Asp Ala Lys Ala Thr Thr Leu Ala Lys Phe
            500                 505                 510

Leu Tyr Ser Leu Gly Ile Arg Glu Ala Gly Glu Ala Thr Thr Gln Asn
        515                 520                 525

Leu Ala Asn His Phe Leu Thr Leu Glu Asn Val Ile Asn Ala Ser Ile
    530                 535                 540

Asp Ser Leu Thr Gln Val Ser Asp Val Gly Ile Val Ala Thr His
545                 550                 555                 560

Val Arg Ser Phe Phe Ala Glu Gln His Asn Leu Asp Val Val Asn Ala
                565                 570                 575

Leu Val Glu Gln Gly Ile Asn Trp Pro Glu Leu Thr Pro Pro Ser Ala
            580                 585                 590

Gln Glu Gln Pro Leu Ala Gly Leu Val Tyr Val Leu Thr Gly Thr Leu
        595                 600                 605

Asn Thr Leu Asn Arg Asn Asp Ala Lys Ala Arg Leu Gln Gln Leu Gly
    610                 615                 620

Ala Lys Val Ser Gly Ser Val Ser Ala Lys Thr Asp Ala Leu Val Ala
625                 630                 635                 640

Gly Glu Lys Ala Gly Ser Lys Leu Thr Lys Ala Gln Asp Leu Gly Ile
                645                 650                 655

Asp Val Leu Thr Glu Glu Asp Leu Ile Asn Leu Leu Glu Gln His Asn
            660                 665                 670

Gly

<210> SEQ ID NO 5
<211> LENGTH: 2022
<212> TYPE: DNA
<213> ORGANISM: Artificial Sequence
<220> FEATURE:
<223> OTHER INFORMATION: LigAPh2 hybrid
<220> FEATURE:
<221> NAME/KEY: CDS
<222> LOCATION: (1)..(2022)

<400> SEQUENCE: 5 atg act cca agc att agt gag caa ata aac cat ctt cgt agt acg ctt    48
Met Thr Pro Ser Ile Ser Glu Gln Ile Asn His Leu Arg Ser Thr Leu
1               5                   10                  15 gaa cag cac agt tac aat tat tat gta ctt gat acc ccc agt att cct    96
Glu Gln His Ser Tyr Asn Tyr Tyr Val Leu Asp Thr Pro Ser Ile Pro
            20                  25                  30 gat gct gaa tac gac cgt tta tta caa caa ctc agc gca cta gaa act   144
Asp Ala Glu Tyr Asp Arg Leu Leu Gln Gln Leu Ser Ala Leu Glu Thr
        35                  40                  45
```

-continued

| | | |
|---|---|---|
| cag cac cca gaa tta ata act gcc gac tca cca acc caa aaa gtg ggc<br>Gln His Pro Glu Leu Ile Thr Ala Asp Ser Pro Thr Gln Lys Val Gly<br>     50                        55                        60 | | 192 |
| ggt gct gcg cta agt aaa ttt gag caa gta gcg cac caa gtg cct atg<br>Gly Ala Ala Leu Ser Lys Phe Glu Gln Val Ala His Gln Val Pro Met<br>65                     70                       75                     80 | | 240 |
| tta tcg ctt gat aac gcc ttt agc gaa gat gag ttt att gcc ttt aat<br>Leu Ser Leu Asp Asn Ala Phe Ser Glu Asp Glu Phe Ile Ala Phe Asn<br>                 85                       90                    95 | | 288 |
| cgc cgt ata aaa gag cgt tta atg agt acc gaa gag ctt act ttt tgt<br>Arg Arg Ile Lys Glu Arg Leu Met Ser Thr Glu Glu Leu Thr Phe Cys<br>               100                    105                 110 | | 336 |
| tgt gag cca aaa cta gat ggc tta gct gtg tcg att att tat cgt gat<br>Cys Glu Pro Lys Leu Asp Gly Leu Ala Val Ser Ile Ile Tyr Arg Asp<br>         115                    120                 125 | | 384 |
| ggc gta cta gtg caa gcc gcg acc cga ggt gat ggg ttg acg gga gaa<br>Gly Val Leu Val Gln Ala Ala Thr Arg Gly Asp Gly Leu Thr Gly Glu<br>130                     135                    140 | | 432 |
| aat gta act caa aaa gtt aaa aca att cgt aat gtg cca ctt aaa tta<br>Asn Val Thr Gln Lys Val Lys Thr Ile Arg Asn Val Pro Leu Lys Leu<br>145                     150                    155                 160 | | 480 |
| cga ggt agc gat tat cct gct gaa cta gaa gtg cgc ggc gaa gtg ttt<br>Arg Gly Ser Asp Tyr Pro Ala Glu Leu Glu Val Arg Gly Glu Val Phe<br>                 165                    170                 175 | | 528 |
| atg gat aat gca ggc ttt gaa aag ttt aac att gaa gct gaa aaa cgt<br>Met Asp Asn Ala Gly Phe Glu Lys Phe Asn Ile Glu Ala Glu Lys Arg<br>180                     185                    190 | | 576 |
| ggt gaa aaa gta ttt gta aac cca cgc aac gcc gcc gca ggt agc ctg<br>Gly Glu Lys Val Phe Val Asn Pro Arg Asn Ala Ala Ala Gly Ser Leu<br>               195                    200                 205 | | 624 |
| cgc cag ctt gac tct aaa att acg gct aaa cgc cca ctg atg ttt tat<br>Arg Gln Leu Asp Ser Lys Ile Thr Ala Lys Arg Pro Leu Met Phe Tyr<br>210                     215                    220 | | 672 |
| gcc tac agc aca ggt ctt gta gcc gac ggt agc att gca gag gat cat<br>Ala Tyr Ser Thr Gly Leu Val Ala Asp Gly Ser Ile Ala Glu Asp His<br>225                     230                    235                 240 | | 720 |
| tat cag caa tta gaa aaa ttg act gat tgg ggg tta cca ctt tgc cct<br>Tyr Gln Gln Leu Glu Lys Leu Thr Asp Trp Gly Leu Pro Leu Cys Pro<br>               245                    250                 255 | | 768 |
| gaa aca aaa tta gta gaa ggc cca caa gct gca ctg gct tat tat act<br>Glu Thr Lys Leu Val Glu Gly Pro Gln Ala Ala Leu Ala Tyr Tyr Thr<br>260                     265                    270 | | 816 |
| gac att tta acg cgc cgt ggc gag ctt aaa tat gaa ata gat ggc gtg<br>Asp Ile Leu Thr Arg Arg Gly Glu Leu Lys Tyr Glu Ile Asp Gly Val<br>               275                    280                 285 | | 864 |
| gta ata aaa ata aat caa aaa gcc tta caa gag cgt tta ggc ttt gta<br>Val Ile Lys Ile Asn Gln Lys Ala Leu Gln Glu Arg Leu Gly Phe Val<br>290                     295                    300 | | 912 |
| gca cgc gct ccg cgt tgg gct att gct tat aag ttc ccg gcc caa gaa<br>Ala Arg Ala Pro Arg Trp Ala Ile Ala Tyr Lys Phe Pro Ala Gln Glu<br>305                     310                    315                 320 | | 960 |
| gaa ata acc aaa tta ctc gat gta gag ttt cag gtg ggg cgt acg gga<br>Glu Ile Thr Lys Leu Leu Asp Val Glu Phe Gln Val Gly Arg Thr Gly<br>               325                    330                 335 | | 1008 |
| gca att aca ccg gtt gca cgc tta gag ccg gta ttt gtt ggt ggt gtt<br>Ala Ile Thr Pro Val Ala Arg Leu Glu Pro Val Phe Val Gly Gly Val<br>340                     345                    350 | | 1056 |
| act gta tca aac gct acc ttg cac aat ggc gat gaa ata gcg cgc tta<br>Thr Val Ser Asn Ala Thr Leu His Asn Gly Asp Glu Ile Ala Arg Leu<br>               355                    360                 365 | | 1104 |

-continued

```
ggc gta aaa gtg ggc gac acg gta att att cgc cgt gca ggg gac gta      1152
Gly Val Lys Val Gly Asp Thr Val Ile Ile Arg Arg Ala Gly Asp Val
        370             375             380 att cca caa ata acg caa gta gta ctt gag cgc cgc cct gat gat gcc      1200
Ile Pro Gln Ile Thr Gln Val Val Leu Glu Arg Arg Pro Asp Asp Ala
385             390             395             400 cgc gat att gag ttt ccg gta act tgc cca att tgt gac tcc cat gta      1248
Arg Asp Ile Glu Phe Pro Val Thr Cys Pro Ile Cys Asp Ser His Val
            405             410             415 gaa aaa gta gaa ggt gaa gcc gta gcg cgt tgt act ggt ggt tta gtg      1296
Glu Lys Val Glu Gly Glu Ala Val Ala Arg Cys Thr Gly Gly Leu Val
        420             425             430 tgc ccg gcg caa cgt aaa caa gcg att aaa cac ttt gca tcg cgc aaa      1344
Cys Pro Ala Gln Arg Lys Gln Ala Ile Lys His Phe Ala Ser Arg Lys
            435             440             445 gca ctc gat att gac ggc ctt ggc gat aaa att gtt gat caa ctc gtc      1392
Ala Leu Asp Ile Asp Gly Leu Gly Asp Lys Ile Val Asp Gln Leu Val
    450             455             460 gac aga gag ctg att aaa acc cct gca gat ttg ttt att tta aag caa      1440
Asp Arg Glu Leu Ile Lys Thr Pro Ala Asp Leu Phe Ile Leu Lys Gln
465             470             475             480 gga cat ttt gaa tcg ctt gag cgt atg ggg cca aag tcg gct aaa aat      1488
Gly His Phe Glu Ser Leu Glu Arg Met Gly Pro Lys Ser Ala Lys Asn
            485             490             495 ttg gtt act gcg ctt caa gac gct aaa gca aca act ttg gct aag ttt      1536
Leu Val Thr Ala Leu Gln Asp Ala Lys Ala Thr Thr Leu Ala Lys Phe
        500             505             510 tta tac tca ttg ggt att cgt gaa gcg ggt gag gca acc aca caa aat      1584
Leu Tyr Ser Leu Gly Ile Arg Glu Ala Gly Glu Ala Thr Thr Gln Asn
        515             520             525 tta gct aat cat ttc tta acc ctt gaa aac gta ata aat gcc agc att      1632
Leu Ala Asn His Phe Leu Thr Leu Glu Asn Val Ile Asn Ala Ser Ile
    530             535             540 gat agt tta act caa gta agt gat gtg ggc gaa ata gta gca acc cat      1680
Asp Ser Leu Thr Gln Val Ser Asp Val Gly Glu Ile Val Ala Thr His
545             550             555             560 gta cgt agc ttt ttt gcc gaa cag cat aat tta gat gtt gta aat gcg      1728
Val Arg Ser Phe Phe Ala Glu Gln His Asn Leu Asp Val Val Asn Ala
            565             570             575 ctg gta gag caa ggt att aat tgg cct gaa ctt act cca cct tca gcg      1776
Leu Val Glu Gln Gly Ile Asn Trp Pro Glu Leu Thr Pro Pro Ser Ala
        580             585             590 caa gag cag cca tta gct ggc ctt gtt tat gtg ctt acc ggt acc tta      1824
Gln Glu Gln Pro Leu Ala Gly Leu Val Tyr Val Leu Thr Gly Thr Leu
        595             600             605 aac aca tta aac cgt aat gac gcc aaa gca cgt ttg caa cag tta ggt      1872
Asn Thr Leu Asn Arg Asn Asp Ala Lys Ala Arg Leu Gln Gln Leu Gly
    610             615             620 gct aaa gtg tcg ggt agt gtg tcg gct aaa acc gat gcg tta gta gca      1920
Ala Lys Val Ser Gly Ser Val Ser Ala Lys Thr Asp Ala Leu Val Ala
625             630             635             640 ggc gaa aag gcc ggc tct aaa cta act aag gca caa gac tta ggt ata      1968
Gly Glu Lys Ala Gly Ser Lys Leu Thr Lys Ala Gln Asp Leu Gly Ile
            645             650             655 gat gta ctg aca gaa gaa gat tta att aat tta tta gag caa cat aat      2016
Asp Val Leu Thr Glu Glu Asp Leu Ile Asn Leu Leu Glu Gln His Asn
        660             665             670 ggc tga                                                              2022
Gly
```

<210> SEQ ID NO 6
<211> LENGTH: 673
<212> TYPE: PRT
<213> ORGANISM: Artificial Sequence
<220> FEATURE:
<223> OTHER INFORMATION: Synthetic Construct

<400> SEQUENCE: 6

```
Met Thr Pro Ser Ile Ser Glu Gln Ile Asn His Leu Arg Ser Thr Leu
1               5                   10                  15

Glu Gln His Ser Tyr Asn Tyr Tyr Val Leu Asp Thr Pro Ser Ile Pro
            20                  25                  30

Asp Ala Glu Tyr Asp Arg Leu Leu Gln Gln Leu Ser Ala Leu Glu Thr
        35                  40                  45

Gln His Pro Glu Leu Ile Thr Ala Asp Ser Pro Thr Gln Lys Val Gly
    50                  55                  60

Gly Ala Ala Leu Ser Lys Phe Glu Gln Val Ala His Gln Val Pro Met
65                  70                  75                  80

Leu Ser Leu Asp Asn Ala Phe Ser Glu Asp Glu Phe Ile Ala Phe Asn
                85                  90                  95

Arg Arg Ile Lys Glu Arg Leu Met Ser Thr Glu Leu Thr Phe Cys
            100                 105                 110

Cys Glu Pro Lys Leu Asp Gly Leu Ala Val Ser Ile Ile Tyr Arg Asp
        115                 120                 125

Gly Val Leu Val Gln Ala Thr Arg Gly Asp Gly Leu Thr Gly Glu
    130                 135                 140

Asn Val Thr Gln Lys Val Lys Thr Ile Arg Asn Val Pro Leu Lys Leu
145                 150                 155                 160

Arg Gly Ser Asp Tyr Pro Ala Glu Leu Glu Val Arg Gly Glu Val Phe
                165                 170                 175

Met Asp Asn Ala Gly Phe Glu Lys Phe Asn Ile Glu Ala Glu Lys Arg
            180                 185                 190

Gly Glu Lys Val Phe Val Asn Pro Arg Asn Ala Ala Ala Gly Ser Leu
        195                 200                 205

Arg Gln Leu Asp Ser Lys Ile Thr Ala Lys Arg Pro Leu Met Phe Tyr
    210                 215                 220

Ala Tyr Ser Thr Gly Leu Val Ala Asp Gly Ser Ile Ala Glu Asp His
225                 230                 235                 240

Tyr Gln Gln Leu Glu Lys Leu Thr Asp Trp Gly Leu Pro Leu Cys Pro
                245                 250                 255

Glu Thr Lys Leu Val Glu Gly Pro Gln Ala Ala Leu Ala Tyr Tyr Thr
            260                 265                 270

Asp Ile Leu Thr Arg Arg Gly Glu Leu Lys Tyr Glu Ile Asp Gly Val
        275                 280                 285

Val Ile Lys Ile Asn Gln Lys Ala Leu Gln Glu Arg Leu Gly Phe Val
    290                 295                 300

Ala Arg Ala Pro Arg Trp Ala Ile Ala Tyr Lys Phe Pro Ala Gln Glu
305                 310                 315                 320

Glu Ile Thr Lys Leu Leu Asp Val Glu Phe Gln Val Gly Arg Thr Gly
                325                 330                 335

Ala Ile Thr Pro Val Ala Arg Leu Glu Pro Val Phe Val Gly Gly Val
            340                 345                 350

Thr Val Ser Asn Ala Thr Leu His Asn Gly Asp Glu Ile Ala Arg Leu
        355                 360                 365
```

-continued

```
Gly Val Lys Val Gly Asp Thr Val Ile Ile Arg Arg Ala Gly Asp Val
            370                 375                 380
Ile Pro Gln Ile Thr Gln Val Val Leu Glu Arg Arg Pro Asp Asp Ala
385                 390                 395                 400
Arg Asp Ile Glu Phe Pro Val Thr Cys Pro Ile Cys Asp Ser His Val
                405                 410                 415
Glu Lys Val Glu Gly Glu Ala Val Ala Arg Cys Thr Gly Gly Leu Val
            420                 425                 430
Cys Pro Ala Gln Arg Lys Gln Ala Ile Lys His Phe Ala Ser Arg Lys
        435                 440                 445
Ala Leu Asp Ile Asp Gly Leu Gly Asp Lys Ile Val Ala Gln Leu Val
    450                 455                 460
Asp Arg Glu Leu Ile Lys Thr Pro Ala Asp Leu Phe Ile Leu Lys Gln
465                 470                 475                 480
Gly His Phe Glu Ser Leu Glu Arg Met Gly Pro Lys Ser Ala Lys Asn
                485                 490                 495
Leu Val Thr Ala Leu Gln Asp Ala Lys Ala Thr Thr Leu Ala Lys Phe
            500                 505                 510
Leu Tyr Ser Leu Gly Ile Arg Glu Ala Gly Glu Ala Thr Thr Gln Asn
        515                 520                 525
Leu Ala Asn His Phe Leu Thr Leu Glu Asn Val Ile Asn Ala Ser Ile
    530                 535                 540
Asp Ser Leu Thr Gln Val Ser Asp Val Gly Glu Ile Val Ala Thr His
545                 550                 555                 560
Val Arg Ser Phe Phe Ala Glu Gln His Asn Leu Asp Val Val Asn Ala
                565                 570                 575
Leu Val Glu Gln Gly Ile Asn Trp Pro Glu Leu Thr Pro Pro Ser Ala
            580                 585                 590
Gln Glu Gln Pro Leu Ala Gly Leu Val Tyr Val Leu Thr Gly Thr Leu
        595                 600                 605
Asn Thr Leu Asn Arg Asn Asp Ala Lys Ala Arg Leu Gln Gln Leu Gly
    610                 615                 620
Ala Lys Val Ser Gly Ser Val Ser Ala Lys Thr Asp Ala Leu Val Ala
625                 630                 635                 640
Gly Glu Lys Ala Gly Ser Lys Leu Thr Lys Ala Gln Asp Leu Gly Ile
                645                 650                 655
Asp Val Leu Thr Glu Glu Asp Leu Ile Asn Leu Leu Glu Gln His Asn
            660                 665                 670
Gly
```

<210> SEQ ID NO 7
<211> LENGTH: 2013
<212> TYPE: DNA
<213> ORGANISM: Artificial Sequence
<220> FEATURE:
<223> OTHER INFORMATION: LigASf hybrid
<220> FEATURE:
<221> NAME/KEY: CDS
<222> LOCATION: (1)..(2013)

<400> SEQUENCE: 7

```
atg act cca att caa act gaa atg gat caa ctt act cac acc att aac      48
Met Thr Pro Ile Gln Thr Glu Met Asp Gln Leu Thr His Thr Ile Asn
1               5                  10                  15 caa cat aat att cgt tat tac gtt gat gat gct ccg tca ata ccc gat      96
Gln His Asn Ile Arg Tyr Tyr Val Asp Asp Ala Pro Ser Ile Pro Asp
```

```
                    20                  25                  30
gct gaa tac gac aga tta att aag cgc tta act gag tta gaa cgt gac     144
Ala Glu Tyr Asp Arg Leu Ile Lys Arg Leu Thr Glu Leu Glu Arg Asp
         35                  40                  45 tat ccg caa ttt aaa tcg gta gat tca ccg aca caa cgc gtc ggt ggt     192
Tyr Pro Gln Phe Lys Ser Val Asp Ser Pro Thr Gln Arg Val Gly Gly
 50                  55                  60 ata gca tta caa aaa ttt gct caa att acc cac ctt aaa ccg atg tta     240
Ile Ala Leu Gln Lys Phe Ala Gln Ile Thr His Leu Lys Pro Met Leu
 65                  70                  75                  80 agt ctc gac aat gcg ttt gaa caa gcc gat ttt gca gca ttt aat aag     288
Ser Leu Asp Asn Ala Phe Glu Gln Ala Asp Phe Ala Ala Phe Asn Lys
                 85                  90                  95 cgt ata act gat aaa gtc gat agc gtc gat tat gtt tgc gaa cca aaa     336
Arg Ile Thr Asp Lys Val Asp Ser Val Asp Tyr Val Cys Glu Pro Lys
            100                 105                 110 cta gac gga ttg gcc gtg agt att act tat cgt ttt ggc gtt ctt gaa     384
Leu Asp Gly Leu Ala Val Ser Ile Thr Tyr Arg Phe Gly Val Leu Glu
        115                 120                 125 cgc gcc gca acg cga ggt gat ggc agt gtc ggc gaa gat att acc gct     432
Arg Ala Ala Thr Arg Gly Asp Gly Ser Val Gly Glu Asp Ile Thr Ala
    130                 135                 140 aat gtg cgt act att cgt tca att cct ctt aag tta cgc ggt gaa gga     480
Asn Val Arg Thr Ile Arg Ser Ile Pro Leu Lys Leu Arg Gly Glu Gly
145                 150                 155                 160 ttt cca gat tta gtt gaa gta cgt ggc gaa gtg ttt atg cct aaa gcg     528
Phe Pro Asp Leu Val Glu Val Arg Gly Glu Val Phe Met Pro Lys Ala
                165                 170                 175 gca ttt gag gca tta aac cag cgt caa atc agc aaa ggt gac aaa gtc     576
Ala Phe Glu Ala Leu Asn Gln Arg Gln Ile Ser Lys Gly Asp Lys Val
            180                 185                 190 ttt gtt aat cct cgc aac gca gct gcc ggc agt ttg cgc caa tta gac     624
Phe Val Asn Pro Arg Asn Ala Ala Ala Gly Ser Leu Arg Gln Leu Asp
        195                 200                 205 agt aaa att acc gct tca agg gct ctt ggg ttt tat gct tat gca tta     672
Ser Lys Ile Thr Ala Ser Arg Ala Leu Gly Phe Tyr Ala Tyr Ala Leu
    210                 215                 220 ggt gta gtc gaa ggc gag tca caa ccg atg caa aca agc cac tat ggc     720
Gly Val Val Glu Gly Glu Ser Gln Pro Met Gln Thr Ser His Tyr Gly
225                 230                 235                 240 caa cta aca cag ctg caa caa tgg ggt att ccc gtt agt agt gaa gtg     768
Gln Leu Thr Gln Leu Gln Gln Trp Gly Ile Pro Val Ser Ser Glu Val
                245                 250                 255 aaa gtg act gat tta tta gaa aaa gtc tat gca tat tac gcc gat att     816
Lys Val Thr Asp Leu Leu Glu Lys Val Tyr Ala Tyr Tyr Ala Asp Ile
            260                 265                 270 atg gcc aga cga agt gcg ctt gaa tat gaa att gac ggc gtc gtc ata     864
Met Ala Arg Arg Ser Ala Leu Glu Tyr Glu Ile Asp Gly Val Val Ile
        275                 280                 285 aag gtt aat gac att gcc aag caa caa aca ctt ggt ttt gtg gct aaa     912
Lys Val Asn Asp Ile Ala Lys Gln Gln Thr Leu Gly Phe Val Ala Lys
    290                 295                 300 gct cct cga tgg gcc ata gcc tat aaa ttt cca gcc cag gaa gaa atg     960
Ala Pro Arg Trp Ala Ile Ala Tyr Lys Phe Pro Ala Gln Glu Glu Met
305                 310                 315                 320 acc ttg tta gag tct gtt gac ttt cag gtt ggc cga acg ggt gct gtt    1008
Thr Leu Leu Glu Ser Val Asp Phe Gln Val Gly Arg Thr Gly Ala Val
                325                 330                 335 acc cct gtc gct cgc ctc aaa ccg ata ttt gtc ggt ggc gtg act gtg    1056
```

```
Thr Pro Val Ala Arg Leu Lys Pro Ile Phe Val Gly Gly Val Thr Val
                340                 345                 350 tcg aat gcg acc ttg cac aat gct gat gaa att gcc cgt ctt ggg gtg        1104
Ser Asn Ala Thr Leu His Asn Ala Asp Glu Ile Ala Arg Leu Gly Val
        355                 360                 365 aaa ata ggc gat aca gtg att att cgc cgc gca ggt gac gtt atc ccg        1152
Lys Ile Gly Asp Thr Val Ile Ile Arg Arg Ala Gly Asp Val Ile Pro
370                 375                 380 caa att gtt gct atc gtg cca gaa aag cgc cct gat gat gca caa gat        1200
Gln Ile Val Ala Ile Val Pro Glu Lys Arg Pro Asp Asp Ala Gln Asp
385                 390                 395                 400 att atc ttt cca ctg cat tgt cct gtg tgc caa agc att gtt gag cgt        1248
Ile Ile Phe Pro Leu His Cys Pro Val Cys Gln Ser Ile Val Glu Arg
                405                 410                 415 tta gaa ggt gaa gct gta gcg cgt tgt agt ggt gga ctt ttt tgt gaa        1296
Leu Glu Gly Glu Ala Val Ala Arg Cys Ser Gly Gly Leu Phe Cys Glu
            420                 425                 430 gcg caa cgt aaa gag gcg att aaa cat ttt gca tcc cgt aaa gca tta        1344
Ala Gln Arg Lys Glu Ala Ile Lys His Phe Ala Ser Arg Lys Ala Leu
        435                 440                 445 aat att gat ggc atg ggc gat aaa atc gtt gag caa tta att gat aaa        1392
Asn Ile Asp Gly Met Gly Asp Lys Ile Val Glu Gln Leu Ile Asp Lys
450                 455                 460 gaa cta gtc aaa acg cca gca gac ttg ttt tcc ctt acc gct tct agc        1440
Glu Leu Val Lys Thr Pro Ala Asp Leu Phe Ser Leu Thr Ala Ser Ser
465                 470                 475                 480 atc acg atg tta gat cgc atg gcg atg aag tca gcc aca aat att gtc        1488
Ile Thr Met Leu Asp Arg Met Ala Met Lys Ser Ala Thr Asn Ile Val
                485                 490                 495 gcg gcg att aaa cac gct aaa gcc act aca tta gcg cgt ttt tta tat        1536
Ala Ala Ile Lys His Ala Lys Ala Thr Thr Leu Ala Arg Phe Leu Tyr
            500                 505                 510 agt ctt ggg atc cgc gaa gtc ggc gaa gct acc gcc gct aat tta gcc        1584
Ser Leu Gly Ile Arg Glu Val Gly Glu Ala Thr Ala Ala Asn Leu Ala
        515                 520                 525 caa cac ttt gcc gaa ttt gag cgt att cga act gct agc gtt gaa caa        1632
Gln His Phe Ala Glu Phe Glu Arg Ile Arg Thr Ala Ser Val Glu Gln
530                 535                 540 ctg ctc gaa gtc gct gat gtt ggt gac att gta gca aaa cac att cga        1680
Leu Leu Glu Val Ala Asp Val Gly Asp Ile Val Ala Lys His Ile Arg
545                 550                 555                 560 caa ttt ttt gca cag cca cat aac att gaa gta ata gag caa ttg ctt        1728
Gln Phe Phe Ala Gln Pro His Asn Ile Glu Val Ile Glu Gln Leu Leu
                565                 570                 575 gaa gcc ggc att act tgg cct gtt att gaa caa gct gac gaa tcg cag        1776
Glu Ala Gly Ile Thr Trp Pro Val Ile Glu Gln Ala Asp Glu Ser Gln
            580                 585                 590 ctt agt ctt aaa ggg caa acg tgg gtg tta act ggt acg cta act caa        1824
Leu Ser Leu Lys Gly Gln Thr Trp Val Leu Thr Gly Thr Leu Thr Gln
        595                 600                 605 ctt aat cgt aac gat gcc aaa gcc caa tta cag gct ttg ggc gcc aaa        1872
Leu Asn Arg Asn Asp Ala Lys Ala Gln Leu Gln Ala Leu Gly Ala Lys
610                 615                 620 gtg gct ggc agt gtt tcg aaa aat act gat tgc ctt gtt gct ggt gaa        1920
Val Ala Gly Ser Val Ser Lys Asn Thr Asp Cys Leu Val Ala Gly Glu
625                 630                 635                 640 gca gcg ggt tct aaa tta gca aaa gct gaa gaa ttg ggc gtt aag gtg        1968
Ala Ala Gly Ser Lys Leu Ala Lys Ala Glu Glu Leu Gly Val Lys Val
                645                 650                 655
```

```
                ata gat gaa caa gct ctg atg gat tta ttg aat gcg gct aac tga       2013
                Ile Asp Glu Gln Ala Leu Met Asp Leu Leu Asn Ala Ala Asn
                        660             665             670

<210> SEQ ID NO 8
<211> LENGTH: 670
<212> TYPE: PRT
<213> ORGANISM: Artificial Sequence
<220> FEATURE:
<223> OTHER INFORMATION: Synthetic Construct

<400> SEQUENCE: 8

Met Thr Pro Ile Gln Thr Glu Met Asp Gln Leu Thr His Thr Ile Asn
1               5                   10                  15

Gln His Asn Ile Arg Tyr Tyr Val Asp Asp Ala Pro Ser Ile Pro Asp
            20                  25                  30

Ala Glu Tyr Asp Arg Leu Ile Lys Arg Leu Thr Glu Leu Glu Arg Asp
        35                  40                  45

Tyr Pro Gln Phe Lys Ser Val Asp Ser Pro Thr Gln Arg Val Gly Gly
    50                  55                  60

Ile Ala Leu Gln Lys Phe Ala Gln Ile Thr His Leu Lys Pro Met Leu
65                  70                  75                  80

Ser Leu Asp Asn Ala Phe Glu Gln Ala Asp Phe Ala Ala Phe Asn Lys
                85                  90                  95

Arg Ile Thr Asp Lys Val Asp Ser Val Asp Tyr Val Cys Glu Pro Lys
            100                 105                 110

Leu Asp Gly Leu Ala Val Ser Ile Thr Tyr Arg Phe Gly Val Leu Glu
        115                 120                 125

Arg Ala Ala Thr Arg Gly Asp Gly Ser Val Gly Glu Asp Ile Thr Ala
    130                 135                 140

Asn Val Arg Thr Ile Arg Ser Ile Pro Leu Lys Leu Arg Gly Glu Gly
145                 150                 155                 160

Phe Pro Asp Leu Val Glu Val Arg Gly Glu Val Phe Met Pro Lys Ala
                165                 170                 175

Ala Phe Glu Ala Leu Asn Gln Arg Gln Ile Ser Lys Gly Asp Lys Val
            180                 185                 190

Phe Val Asn Pro Arg Asn Ala Ala Gly Ser Leu Arg Gln Leu Asp
        195                 200                 205

Ser Lys Ile Thr Ala Ser Arg Ala Leu Gly Phe Tyr Ala Tyr Ala Leu
    210                 215                 220

Gly Val Val Glu Gly Glu Ser Gln Pro Met Gln Thr Ser His Tyr Gly
225                 230                 235                 240

Gln Leu Thr Gln Leu Gln Gln Trp Gly Ile Pro Val Ser Ser Glu Val
                245                 250                 255

Lys Val Thr Asp Leu Leu Glu Lys Val Tyr Ala Tyr Ala Asp Ile
            260                 265                 270

Met Ala Arg Arg Ser Ala Leu Glu Tyr Glu Ile Asp Gly Val Val Ile
        275                 280                 285

Lys Val Asn Asp Ile Ala Lys Gln Gln Thr Leu Gly Phe Val Ala Lys
    290                 295                 300

Ala Pro Arg Trp Ala Ile Ala Tyr Lys Phe Pro Ala Gln Glu Glu Met
305                 310                 315                 320

Thr Leu Leu Glu Ser Val Asp Phe Gln Val Gly Arg Thr Gly Ala Val
                325                 330                 335

Thr Pro Val Ala Arg Leu Lys Pro Ile Phe Val Gly Gly Val Thr Val
            340                 345                 350
```

```
Ser Asn Ala Thr Leu His Asn Ala Asp Glu Ile Ala Arg Leu Gly Val
        355                 360                 365

Lys Ile Gly Asp Thr Val Ile Ile Arg Arg Ala Gly Asp Val Ile Pro
    370                 375                 380

Gln Ile Val Ala Ile Val Pro Glu Lys Arg Pro Asp Asp Ala Gln Asp
385                 390                 395                 400

Ile Ile Phe Pro Leu His Cys Pro Val Cys Gln Ser Ile Val Glu Arg
                405                 410                 415

Leu Glu Gly Glu Ala Val Ala Arg Cys Ser Gly Gly Leu Phe Cys Glu
            420                 425                 430

Ala Gln Arg Lys Glu Ala Ile Lys His Phe Ala Ser Arg Lys Ala Leu
        435                 440                 445

Asn Ile Asp Gly Met Gly Asp Lys Ile Val Glu Gln Leu Ile Asp Lys
    450                 455                 460

Glu Leu Val Lys Thr Pro Ala Asp Leu Phe Ser Leu Thr Ala Ser Ser
465                 470                 475                 480

Ile Thr Met Leu Asp Arg Met Ala Met Lys Ser Ala Thr Asn Ile Val
                485                 490                 495

Ala Ala Ile Lys His Ala Lys Ala Thr Thr Leu Ala Arg Phe Leu Tyr
            500                 505                 510

Ser Leu Gly Ile Arg Glu Val Gly Glu Ala Thr Ala Ala Asn Leu Ala
        515                 520                 525

Gln His Phe Ala Glu Phe Glu Arg Ile Arg Thr Ala Ser Val Glu Gln
    530                 535                 540

Leu Leu Glu Val Ala Asp Val Gly Asp Ile Val Ala Lys His Ile Arg
545                 550                 555                 560

Gln Phe Phe Ala Gln Pro His Asn Ile Glu Val Ile Glu Gln Leu Leu
                565                 570                 575

Glu Ala Gly Ile Thr Trp Pro Val Ile Glu Gln Ala Asp Glu Ser Gln
            580                 585                 590

Leu Ser Leu Lys Gly Gln Thr Trp Val Leu Thr Gly Thr Leu Thr Gln
        595                 600                 605

Leu Asn Arg Asn Asp Ala Lys Ala Gln Leu Gln Ala Leu Gly Ala Lys
    610                 615                 620

Val Ala Gly Ser Val Ser Lys Asn Thr Asp Cys Leu Val Ala Gly Glu
625                 630                 635                 640

Ala Ala Gly Ser Lys Leu Ala Lys Ala Glu Glu Leu Gly Val Lys Val
                645                 650                 655

Ile Asp Glu Gln Ala Leu Met Asp Leu Leu Asn Ala Ala Asn
            660                 665                 670

<210> SEQ ID NO 9
<211> LENGTH: 1638
<212> TYPE: DNA
<213> ORGANISM: Artificial Sequence
<220> FEATURE:
<223> OTHER INFORMATION: PyrGCp hybrid
<220> FEATURE:
<221> NAME/KEY: CDS
<222> LOCATION: (1)..(1638)

<400> SEQUENCE: 9 atg aat tct aac act aaa att att ttc gtc aca ggt ggg gta gta tca      48
Met Asn Ser Asn Thr Lys Ile Ile Phe Val Thr Gly Gly Val Val Ser
1               5                   10                  15 tca ctt ggt aag ggt gta act gcg gca tct ttg gct act ctc tta gaa     96
```

```
Ser Leu Gly Lys Gly Val Thr Ala Ala Ser Leu Ala Thr Leu Leu Glu
             20                  25                  30 agt cgt ggt ctt aat gta aca atg atg aag ctt gat cca tac atc aat      144
Ser Arg Gly Leu Asn Val Thr Met Met Lys Leu Asp Pro Tyr Ile Asn
         35                  40                  45 gtt gat cca ggg act atg agt cca ttg caa cat ggt gaa gtt ttt gta      192
Val Asp Pro Gly Thr Met Ser Pro Leu Gln His Gly Glu Val Phe Val
 50                  55                  60 acc gaa gat ggc gca gag act gat ctt gat tta ggt cat tat gag cgc      240
Thr Glu Asp Gly Ala Glu Thr Asp Leu Asp Leu Gly His Tyr Glu Arg
 65                  70                  75                  80 ttt atc cgc aat aag atg act caa gca aat aac ttc aca acc ggt aaa      288
Phe Ile Arg Asn Lys Met Thr Gln Ala Asn Asn Phe Thr Thr Gly Lys
                 85                  90                  95 gta tac cag agt gtg tta aga aga gag cgt aag ggt gat tat cta ggt      336
Val Tyr Gln Ser Val Leu Arg Arg Glu Arg Lys Gly Asp Tyr Leu Gly
             100                 105                 110 gct act atc cag gtg att cca cat atc att gat gag atc aaa agg cgt      384
Ala Thr Ile Gln Val Ile Pro His Ile Ile Asp Glu Ile Lys Arg Arg
         115                 120                 125 att tgt agt ggt att gct gat gat gtt gat gtt gcg att gtt gag att      432
Ile Cys Ser Gly Ile Ala Asp Asp Val Asp Val Ala Ile Val Glu Ile
 130                 135                 140 ggt ggt act gtt ggt gat atc gag tca caa cca ttt tta gaa gct att      480
Gly Gly Thr Val Gly Asp Ile Glu Ser Gln Pro Phe Leu Glu Ala Ile
145                 150                 155                 160 cgt caa ttg gca tta gag gta ggt cgt gat cgt gct atg ttt atg cat      528
Arg Gln Leu Ala Leu Glu Val Gly Arg Asp Arg Ala Met Phe Met His
                 165                 170                 175 ttg acc tta gtg cca tat tta gca gca gca ggt gaa atc aaa act aaa      576
Leu Thr Leu Val Pro Tyr Leu Ala Ala Ala Gly Glu Ile Lys Thr Lys
             180                 185                 190 cca aca cag cac tca gta aaa gat tta cgc tct atc ggt att ttt cct      624
Pro Thr Gln His Ser Val Lys Asp Leu Arg Ser Ile Gly Ile Phe Pro
         195                 200                 205 gac att tta gta tgt cgt tca gac cgc gct att cct aac gcc gaa cgc      672
Asp Ile Leu Val Cys Arg Ser Asp Arg Ala Ile Pro Asn Ala Glu Arg
 210                 215                 220 gct aaa ata tct ctc ttc act aat gtt gaa gag aaa gcg gtt gta tca      720
Ala Lys Ile Ser Leu Phe Thr Asn Val Glu Glu Lys Ala Val Val Ser
225                 230                 235                 240 atg cgt gat gta gac agt att tat aag att cct gct tta tta aaa gct      768
Met Arg Asp Val Asp Ser Ile Tyr Lys Ile Pro Ala Leu Leu Lys Ala
                 245                 250                 255 caa ggt acc gat gaa ata gtt gtt aag cga ttt ggt tta gat gta cct      816
Gln Gly Thr Asp Glu Ile Val Val Lys Arg Phe Gly Leu Asp Val Pro
             260                 265                 270 gaa gcc gac tta act gaa tgg gaa gaa gtg ctt tac cat gaa gca aat      864
Glu Ala Asp Leu Thr Glu Trp Glu Glu Val Leu Tyr His Glu Ala Asn
         275                 280                 285 cct atc ggt gaa gtg act att ggt atg gtt ggt aaa tac act gaa tta      912
Pro Ile Gly Glu Val Thr Ile Gly Met Val Gly Lys Tyr Thr Glu Leu
 290                 295                 300 cct gat gcg tac aaa tca gta aac gaa gcg tta aaa cat gca ggt ctt      960
Pro Asp Ala Tyr Lys Ser Val Asn Glu Ala Leu Lys His Ala Gly Leu
305                 310                 315                 320 aaa aac caa gtc act gta aat att aaa tac att gac tcg caa gat gta     1008
Lys Asn Gln Val Thr Val Asn Ile Lys Tyr Ile Asp Ser Gln Asp Val
                 325                 330                 335
```

```
gaa gtc aaa ggt gtt gaa atc tta gct aac ttg gat gct att tta gtt    1056
Glu Val Lys Gly Val Glu Ile Leu Ala Asn Leu Asp Ala Ile Leu Val
            340                 345                 350 cct ggt ggt ttc ggt gaa cgt ggt gtt gaa ggt aaa att tta acg gca    1104
Pro Gly Gly Phe Gly Glu Arg Gly Val Glu Gly Lys Ile Leu Thr Ala
        355                 360                 365 caa tat gcg cgt gaa aac aaa gta cct tat tta ggt att tgt tta ggt    1152
Gln Tyr Ala Arg Glu Asn Lys Val Pro Tyr Leu Gly Ile Cys Leu Gly
    370                 375                 380 atg caa gta gcc tta att gaa ttt gct cgt aat gtt gcc ggt tta act    1200
Met Gln Val Ala Leu Ile Glu Phe Ala Arg Asn Val Ala Gly Leu Thr
385                 390                 395                 400 gat gcg cac agt act gaa ttt aat agc gaa act cca cac cca gtg gtt    1248
Asp Ala His Ser Thr Glu Phe Asn Ser Glu Thr Pro His Pro Val Val
                405                 410                 415 ggt tta atc agt gaa tgg tta gac gaa gaa ggc caa gtt gag tac cga    1296
Gly Leu Ile Ser Glu Trp Leu Asp Glu Glu Gly Gln Val Glu Tyr Arg
            420                 425                 430 aat gag caa tca gat tta ggt ggt act atg cgt tta ggt tca caa ttg    1344
Asn Glu Gln Ser Asp Leu Gly Gly Thr Met Arg Leu Gly Ser Gln Leu
        435                 440                 445 tgc cac ttg gtg aaa ggt acc aag gct tgc gac gta tat ggt agt gaa    1392
Cys His Leu Val Lys Gly Thr Lys Ala Cys Asp Val Tyr Gly Ser Glu
    450                 455                 460 aca atc aat gag aga cac cgt cat cgt ttt gag gta aat aat aac tac    1440
Thr Ile Asn Glu Arg His Arg His Arg Phe Glu Val Asn Asn Asn Tyr
465                 470                 475                 480 cga gaa caa tta agc aaa gca ggt ttg att ttc tcg ggt tta tcg tca    1488
Arg Glu Gln Leu Ser Lys Ala Gly Leu Ile Phe Ser Gly Leu Ser Ser
                485                 490                 495 gat aaa agt tta gtt gag gtg att gaa ata gcg gat cat cca tgg ttt    1536
Asp Lys Ser Leu Val Glu Val Ile Glu Ile Ala Asp His Pro Trp Phe
            500                 505                 510 att gcg ggt caa ttc cat cct gag ttt aat tct act cca cgt gat ggt    1584
Ile Ala Gly Gln Phe His Pro Glu Phe Asn Ser Thr Pro Arg Asp Gly
        515                 520                 525 cac ccg tta ttc gaa agc ttt gtt gca gcg agt ttt aaa ctg caa aat    1632
His Pro Leu Phe Glu Ser Phe Val Ala Ala Ser Phe Lys Leu Gln Asn
    530                 535                 540 aat tag                                                            1638
Asn
545

<210> SEQ ID NO 10
<211> LENGTH: 545
<212> TYPE: PRT
<213> ORGANISM: Artificial Sequence
<220> FEATURE:
<223> OTHER INFORMATION: Synthetic Construct

<400> SEQUENCE: 10

Met Asn Ser Asn Thr Lys Ile Ile Phe Val Thr Gly Gly Val Val Ser
1               5                   10                  15

Ser Leu Gly Lys Gly Val Thr Ala Ala Ser Leu Ala Thr Leu Leu Glu
            20                  25                  30

Ser Arg Gly Leu Asn Val Thr Met Met Lys Leu Asp Pro Tyr Ile Asn
        35                  40                  45

Val Asp Pro Gly Thr Met Ser Pro Leu Gln His Gly Glu Val Phe Val
    50                  55                  60

Thr Glu Asp Gly Ala Glu Thr Asp Leu Asp Leu Gly His Tyr Glu Arg
```

```
             65                  70                  75                  80
        Phe Ile Arg Asn Lys Met Thr Gln Ala Asn Asn Phe Thr Thr Gly Lys
                         85                  90                  95

Val Tyr Gln Ser Val Leu Arg Arg Glu Arg Lys Gly Asp Tyr Leu Gly
                        100                 105                 110

Ala Thr Ile Gln Val Ile Pro His Ile Ile Asp Glu Ile Lys Arg Arg
                        115                 120                 125

Ile Cys Ser Gly Ile Ala Asp Asp Val Asp Val Ala Ile Val Glu Ile
        130                 135                 140

Gly Gly Thr Val Gly Asp Ile Glu Ser Gln Pro Phe Leu Glu Ala Ile
        145                 150                 155                 160

Arg Gln Leu Ala Leu Glu Val Gly Arg Asp Arg Ala Met Phe Met His
                        165                 170                 175

Leu Thr Leu Val Pro Tyr Leu Ala Ala Ala Gly Glu Ile Lys Thr Lys
                        180                 185                 190

Pro Thr Gln His Ser Val Lys Asp Leu Arg Ser Ile Gly Ile Phe Pro
                        195                 200                 205

Asp Ile Leu Val Cys Arg Ser Asp Arg Ala Ile Pro Asn Ala Glu Arg
        210                 215                 220

Ala Lys Ile Ser Leu Phe Thr Asn Val Glu Glu Lys Ala Val Val Ser
        225                 230                 235                 240

Met Arg Asp Val Asp Ser Ile Tyr Lys Ile Pro Ala Leu Leu Lys Ala
                        245                 250                 255

Gln Gly Thr Asp Glu Ile Val Val Lys Arg Phe Gly Leu Asp Val Pro
                        260                 265                 270

Glu Ala Asp Leu Thr Glu Trp Glu Glu Val Leu Tyr His Glu Ala Asn
                        275                 280                 285

Pro Ile Gly Glu Val Thr Ile Gly Met Val Gly Lys Tyr Thr Glu Leu
        290                 295                 300

Pro Asp Ala Tyr Lys Ser Val Asn Glu Ala Leu Lys His Ala Gly Leu
        305                 310                 315                 320

Lys Asn Gln Val Thr Val Asn Ile Lys Tyr Ile Asp Ser Gln Asp Val
                        325                 330                 335

Glu Val Lys Gly Val Glu Ile Leu Ala Asn Leu Asp Ala Ile Leu Val
                        340                 345                 350

Pro Gly Gly Phe Gly Glu Arg Gly Val Glu Gly Lys Ile Leu Thr Ala
                        355                 360                 365

Gln Tyr Ala Arg Glu Asn Lys Val Pro Tyr Leu Gly Ile Cys Leu Gly
                        370                 375                 380

Met Gln Val Ala Leu Ile Glu Phe Ala Arg Asn Val Ala Gly Leu Thr
        385                 390                 395                 400

Asp Ala His Ser Thr Glu Phe Asn Ser Glu Thr Pro His Pro Val Val
                        405                 410                 415

Gly Leu Ile Ser Glu Trp Leu Asp Glu Glu Gly Gln Val Glu Tyr Arg
                        420                 425                 430

Asn Glu Gln Ser Asp Leu Gly Gly Thr Met Arg Leu Gly Ser Gln Leu
                        435                 440                 445

Cys His Leu Val Lys Gly Thr Lys Ala Cys Asp Val Tyr Gly Ser Glu
        450                 455                 460

Thr Ile Asn Glu Arg His Arg His Arg Phe Glu Val Asn Asn Asn Tyr
        465                 470                 475                 480

Arg Glu Gln Leu Ser Lys Ala Gly Leu Ile Phe Ser Gly Leu Ser Ser
                        485                 490                 495
```

```
Asp Lys Ser Leu Val Glu Val Ile Glu Ile Ala Asp His Pro Trp Phe
            500                 505                 510

Ile Ala Gly Gln Phe His Pro Glu Phe Asn Ser Thr Pro Arg Asp Gly
        515                 520                 525

His Pro Leu Phe Glu Ser Phe Val Ala Ala Ser Phe Lys Leu Gln Asn
    530                 535                 540

Asn
545

<210> SEQ ID NO 11
<211> LENGTH: 954
<212> TYPE: DNA
<213> ORGANISM: Artificial Sequence
<220> FEATURE:
<223> OTHER INFORMATION: hemCCp hybrid
<220> FEATURE:
<221> NAME/KEY: CDS
<222> LOCATION: (1)..(954)

<400> SEQUENCE: 11 atg aaa caa act aca gta cga att gcc acg cgt aaa agc gcc ctc gcc      48
Met Lys Gln Thr Thr Val Arg Ile Ala Thr Arg Lys Ser Ala Leu Ala
1               5                   10                  15 tta tgg caa gca gaa tat gtt aaa gcg caa ctt gag cat ttt cat gac      96
Leu Trp Gln Ala Glu Tyr Val Lys Ala Gln Leu Glu His Phe His Asp
            20                  25                  30 ggt att aat gtt gaa tta gtg cct atg aca acg aaa ggc gac atc att     144
Gly Ile Asn Val Glu Leu Val Pro Met Thr Thr Lys Gly Asp Ile Ile
        35                  40                  45 tta gac acg cct tta gcc aaa gtc ggc ggt aaa ggt tta ttt gtt aaa     192
Leu Asp Thr Pro Leu Ala Lys Val Gly Gly Lys Gly Leu Phe Val Lys
    50                  55                  60 gag ctt gaa gta gca atg ctt gaa gac cgt gct gat att gct gtt cat     240
Glu Leu Glu Val Ala Met Leu Glu Asp Arg Ala Asp Ile Ala Val His
65                  70                  75                  80 tca atg aaa gat gtt cct gtc gat ttt cca gaa ggc tta gga tta gaa     288
Ser Met Lys Asp Val Pro Val Asp Phe Pro Glu Gly Leu Gly Leu Glu
                85                  90                  95 gtc att tgt cct cgt gaa gat ccc cgt gat gct ttt gtt tct aat acc     336
Val Ile Cys Pro Arg Glu Asp Pro Arg Asp Ala Phe Val Ser Asn Thr
            100                 105                 110 atc aaa tca tta agt gat tta cca caa ggc tct att gtt ggc acc tca     384
Ile Lys Ser Leu Ser Asp Leu Pro Gln Gly Ser Ile Val Gly Thr Ser
        115                 120                 125 agc tta cgc cgt cag tgt caa tta aaa gca agc cgc cct gat tta gat     432
Ser Leu Arg Arg Gln Cys Gln Leu Lys Ala Ser Arg Pro Asp Leu Asp
    130                 135                 140 att cgt gat tta cgt ggc aat gta aat acc cgc cta aga aaa tta gat     480
Ile Arg Asp Leu Arg Gly Asn Val Asn Thr Arg Leu Arg Lys Leu Asp
145                 150                 155                 160 gaa ggt cag tac gac gct att ata tta gcc gct gca ggc cta att cgc     528
Glu Gly Gln Tyr Asp Ala Ile Ile Leu Ala Ala Ala Gly Leu Ile Arg
                165                 170                 175 tta gaa atg agc gag cgt att gca cag ttt atc gaa cca gaa gaa atg     576
Leu Glu Met Ser Glu Arg Ile Ala Gln Phe Ile Glu Pro Glu Glu Met
            180                 185                 190 ctt cct gca aat ggc caa ggc gct gtt ggc att gaa tgt cgt aat gat     624
Leu Pro Ala Asn Gly Gln Gly Ala Val Gly Ile Glu Cys Arg Asn Asp
        195                 200                 205 gat gcg aca att aaa gcc tta tta gca cca tta gaa tgt gct acc acc     672
```

```
Asp Ala Thr Ile Lys Ala Leu Leu Ala Pro Leu Glu Cys Ala Thr Thr
    210                 215                 220 cgt att cgt gtt ctt gca gaa cgt gca atg aat aga gca tta caa ggc      720
Arg Ile Arg Val Leu Ala Glu Arg Ala Met Asn Arg Ala Leu Gln Gly
225                 230                 235                 240 ggt tgc cag gtt cct atc ggt agc tat ggt gtt att tct gct gat ggt      768
Gly Cys Gln Val Pro Ile Gly Ser Tyr Gly Val Ile Ser Ala Asp Gly
                245                 250                 255 aaa aat atc cac tta cgt ggc tta gtt ggc tct gtc gat ggt agt gaa      816
Lys Asn Ile His Leu Arg Gly Leu Val Gly Ser Val Asp Gly Ser Glu
            260                 265                 270 atg ata gaa agt gaa atc acc ggc cct gtt gaa gaa ggt gaa gcg ctc      864
Met Ile Glu Ser Glu Ile Thr Gly Pro Val Glu Glu Gly Glu Ala Leu
        275                 280                 285 ggc aat aaa ctc gcg caa gag tta cta agc cga ggt gca gat aaa att      912
Gly Asn Lys Leu Ala Gln Glu Leu Leu Ser Arg Gly Ala Asp Lys Ile
    290                 295                 300 tta cag caa gtt tat tca gaa aat gat atc aaa gag agt taa              954
Leu Gln Gln Val Tyr Ser Glu Asn Asp Ile Lys Glu Ser
305                 310                 315

<210> SEQ ID NO 12
<211> LENGTH: 317
<212> TYPE: PRT
<213> ORGANISM: Artificial Sequence
<220> FEATURE:
<223> OTHER INFORMATION: Synthetic Construct

<400> SEQUENCE: 12

Met Lys Gln Thr Thr Val Arg Ile Ala Thr Arg Lys Ser Ala Leu Ala
1               5                   10                  15

Leu Trp Gln Ala Glu Tyr Val Lys Ala Gln Leu Glu His Phe His Asp
            20                  25                  30

Gly Ile Asn Val Glu Leu Val Pro Met Thr Thr Lys Gly Asp Ile Ile
        35                  40                  45

Leu Asp Thr Pro Leu Ala Lys Val Gly Gly Lys Gly Leu Phe Val Lys
    50                  55                  60

Glu Leu Glu Val Ala Met Leu Glu Asp Arg Ala Asp Ile Ala Val His
65                  70                  75                  80

Ser Met Lys Asp Val Pro Val Asp Phe Pro Glu Gly Leu Gly Leu Glu
                85                  90                  95

Val Ile Cys Pro Arg Glu Asp Pro Arg Asp Ala Phe Val Ser Asn Thr
            100                 105                 110

Ile Lys Ser Leu Ser Asp Leu Pro Gln Gly Ser Ile Val Gly Thr Ser
        115                 120                 125

Ser Leu Arg Arg Gln Cys Gln Leu Lys Ala Ser Arg Pro Asp Leu Asp
    130                 135                 140

Ile Arg Asp Leu Arg Gly Asn Val Asn Thr Arg Leu Arg Lys Leu Asp
145                 150                 155                 160

Glu Gly Gln Tyr Asp Ala Ile Ile Leu Ala Ala Gly Leu Ile Arg
                165                 170                 175

Leu Glu Met Ser Glu Arg Ile Ala Gln Phe Ile Glu Pro Glu Met
            180                 185                 190

Leu Pro Ala Asn Gly Gln Gly Ala Val Gly Ile Glu Cys Arg Asn Asp
        195                 200                 205

Asp Ala Thr Ile Lys Ala Leu Leu Ala Pro Leu Glu Cys Ala Thr Thr
    210                 215                 220
```

```
Arg Ile Arg Val Leu Ala Glu Arg Ala Met Asn Arg Ala Leu Gln Gly
225                 230                 235                 240

Gly Cys Gln Val Pro Ile Gly Ser Tyr Gly Val Ile Ser Ala Asp Gly
            245                 250                 255

Lys Asn Ile His Leu Arg Gly Leu Val Gly Ser Val Asp Gly Ser Glu
            260                 265                 270

Met Ile Glu Ser Glu Ile Thr Gly Pro Val Glu Gly Glu Ala Leu
        275                 280                 285

Gly Asn Lys Leu Ala Gln Glu Leu Leu Ser Arg Gly Ala Asp Lys Ile
            290                 295                 300

Leu Gln Gln Val Tyr Ser Glu Asn Asp Ile Lys Glu Ser
305                 310                 315

<210> SEQ ID NO 13
<211> LENGTH: 984
<212> TYPE: DNA
<213> ORGANISM: Artificial Sequence
<220> FEATURE:
<223> OTHER INFORMATION: fmtCp hybrid
<220> FEATURE:
<221> NAME/KEY: CDS
<222> LOCATION: (1)..(984)

<400> SEQUENCE: 13 atg aaa aaa cca cta aat atc att ttt gca ggt act cct gaa ttc gct    48
Met Lys Lys Pro Leu Asn Ile Ile Phe Ala Gly Thr Pro Glu Phe Ala
1               5                   10                  15 gcc caa cat tta gca gcg tta att aat tct gaa cat aat att gtc gcc    96
Ala Gln His Leu Ala Ala Leu Ile Asn Ser Glu His Asn Ile Val Ala
                20                  25                  30 gtt tat tgt ccc cct gat aaa cca gct ggc cgc ggt aaa aaa cta aca   144
Val Tyr Cys Pro Pro Asp Lys Pro Ala Gly Arg Gly Lys Lys Leu Thr
            35                  40                  45 gct tgt gca aca aag tta ctc gca ata gag cac gac att att gtt gag   192
Ala Cys Ala Thr Lys Leu Leu Ala Ile Glu His Asp Ile Ile Val Glu
        50                  55                  60 caa cct att aac ttt aaa aat gag gaa gac caa caa caa tta gcg aaa   240
Gln Pro Ile Asn Phe Lys Asn Glu Glu Asp Gln Gln Gln Leu Ala Lys
65                  70                  75                  80 tat aac gct gat atc atg gtt gtt gtt gct tat ggt ctg cta tta cct   288
Tyr Asn Ala Asp Ile Met Val Val Val Ala Tyr Gly Leu Leu Leu Pro
                85                  90                  95 gaa gtc att tta aac tct cca cgt tta ggc tgc att aac gta cat ggc   336
Glu Val Ile Leu Asn Ser Pro Arg Leu Gly Cys Ile Asn Val His Gly
            100                 105                 110 tca att cta cca aaa tgg cgt ggt gca gca cct att caa cgt tct ctt   384
Ser Ile Leu Pro Lys Trp Arg Gly Ala Ala Pro Ile Gln Arg Ser Leu
        115                 120                 125 gaa gct gga gat aag aaa acc ggt gtc acc att atg caa atg gat aaa   432
Glu Ala Gly Asp Lys Lys Thr Gly Val Thr Ile Met Gln Met Asp Lys
    130                 135                 140 ggg tta gac acg gga gac atg att cta tcc gct gag tgc gaa ata gaa   480
Gly Leu Asp Thr Gly Asp Met Ile Leu Ser Ala Glu Cys Glu Ile Glu
145                 150                 155                 160 aat aca gat acc agt gca agt ctt tat gaa aaa ctt gcc aac tta ggg   528
Asn Thr Asp Thr Ser Ala Ser Leu Tyr Glu Lys Leu Ala Asn Leu Gly
                165                 170                 175 cca act gcc tta gtt aat aca tta act att atg gct gaa cct gat tat   576
Pro Thr Ala Leu Val Asn Thr Leu Thr Ile Met Ala Glu Pro Asp Tyr
            180                 185                 190
```

```
caa gcc agt aat cat aat atc gct caa gat gat gaa tta gcg act tat      624
Gln Ala Ser Asn His Asn Ile Ala Gln Asp Asp Glu Leu Ala Thr Tyr
            195                 200                 205 gcc aag aaa ctt gat aaa act gaa gca gag ctt aac tgg caa ttc agt      672
Ala Lys Lys Leu Asp Lys Thr Glu Ala Glu Leu Asn Trp Gln Phe Ser
210                 215                 220 gct gat gaa cta cat cga aaa att cgt gct tat att cct tgg cca gtt      720
Ala Asp Glu Leu His Arg Lys Ile Arg Ala Tyr Ile Pro Trp Pro Val
225                 230                 235                 240 gct caa ttt acc ttt aca gaa tct gaa ggt aag cag cat agg tta cgc      768
Ala Gln Phe Thr Phe Thr Glu Ser Glu Gly Lys Gln His Arg Leu Arg
            245                 250                 255 ata tgg caa gca tcc gtg caa gaa tat cga ggc aat gct gat cca ggc      816
Ile Trp Gln Ala Ser Val Gln Glu Tyr Arg Gly Asn Ala Asp Pro Gly
            260                 265                 270 acg ata ata aag gca gac aaa gaa ggg ata gaa gta gca aca acc agt      864
Thr Ile Ile Lys Ala Asp Lys Glu Gly Ile Glu Val Ala Thr Thr Ser
            275                 280                 285 ggt tcg tta cga cta gaa gtc att caa ctt cca ggg aaa aaa gca tta      912
Gly Ser Leu Arg Leu Glu Val Ile Gln Leu Pro Gly Lys Lys Ala Leu
290                 295                 300 gcc gta aaa gac atc cta aat ggt cgc agc gat tgg ttc gtt gtt ggc      960
Ala Val Lys Asp Ile Leu Asn Gly Arg Ser Asp Trp Phe Val Val Gly
305                 310                 315                 320 agc act att aac aag cta gga taa                                      984
Ser Thr Ile Asn Lys Leu Gly
            325

<210> SEQ ID NO 14
<211> LENGTH: 327
<212> TYPE: PRT
<213> ORGANISM: Artificial Sequence
<220> FEATURE:
<223> OTHER INFORMATION: Synthetic Construct

<400> SEQUENCE: 14

Met Lys Lys Pro Leu Asn Ile Ile Phe Ala Gly Thr Pro Glu Phe Ala
1               5                   10                  15

Ala Gln His Leu Ala Ala Leu Ile Asn Ser Glu His Asn Ile Val Ala
            20                  25                  30

Val Tyr Cys Pro Pro Asp Lys Pro Ala Gly Arg Gly Lys Lys Leu Thr
        35                  40                  45

Ala Cys Ala Thr Lys Leu Leu Ala Ile Glu His Asp Ile Ile Val Glu
    50                  55                  60

Gln Pro Ile Asn Phe Lys Asn Glu Glu Asp Gln Gln Leu Ala Lys
65                  70                  75                  80

Tyr Asn Ala Asp Ile Met Val Val Ala Tyr Gly Leu Leu Leu Pro
                85                  90                  95

Glu Val Ile Leu Asn Ser Pro Arg Leu Gly Cys Ile Asn Val His Gly
            100                 105                 110

Ser Ile Leu Pro Lys Trp Arg Gly Ala Ala Pro Ile Gln Arg Ser Leu
        115                 120                 125

Glu Ala Gly Asp Lys Lys Thr Gly Val Thr Ile Met Gln Met Asp Lys
    130                 135                 140

Gly Leu Asp Thr Gly Asp Met Ile Leu Ser Ala Glu Cys Glu Ile Glu
145                 150                 155                 160

Asn Thr Asp Thr Ser Ala Ser Leu Tyr Glu Lys Leu Ala Asn Leu Gly
                165                 170                 175
```

```
Pro Thr Ala Leu Val Asn Thr Leu Thr Ile Met Ala Glu Pro Asp Tyr
            180                 185                 190

Gln Ala Ser Asn His Asn Ile Ala Gln Asp Asp Glu Leu Ala Thr Tyr
        195                 200                 205

Ala Lys Lys Leu Asp Lys Thr Glu Ala Glu Leu Asn Trp Gln Phe Ser
    210                 215                 220

Ala Asp Glu Leu His Arg Lys Ile Arg Ala Tyr Ile Pro Trp Pro Val
225                 230                 235                 240

Ala Gln Phe Thr Phe Thr Glu Ser Glu Gly Lys Gln His Arg Leu Arg
                245                 250                 255

Ile Trp Gln Ala Ser Val Gln Glu Tyr Arg Gly Asn Ala Asp Pro Gly
            260                 265                 270

Thr Ile Ile Lys Ala Asp Lys Glu Gly Ile Glu Val Ala Thr Thr Ser
        275                 280                 285

Gly Ser Leu Arg Leu Glu Val Ile Gln Leu Pro Gly Lys Lys Ala Leu
    290                 295                 300

Ala Val Lys Asp Ile Leu Asn Gly Arg Ser Asp Trp Phe Val Val Gly
305                 310                 315                 320

Ser Thr Ile Asn Lys Leu Gly
                325

<210> SEQ ID NO 15
<211> LENGTH: 1164
<212> TYPE: DNA
<213> ORGANISM: Artificial Sequence
<220> FEATURE:
<223> OTHER INFORMATION: murGCp hybrid
<220> FEATURE:
<221> NAME/KEY: CDS
<222> LOCATION: (1)..(1164)

<400> SEQUENCE: 15 atg agt cta aat cat ggc caa ggt aat aaa gat tta gca aaa act ttg       48
Met Ser Leu Asn His Gly Gln Gly Asn Lys Asp Leu Ala Lys Thr Leu
1               5                   10                  15 tta gtc atg gct ggt ggc acc ggt gga cat ata ttc cct ggt att gcg       96
Leu Val Met Ala Gly Gly Thr Gly Gly His Ile Phe Pro Gly Ile Ala
            20                  25                  30 gtc gcc gat gag ctg aaa gcg caa gga tgg aaa atc cat tgg ttg gga      144
Val Ala Asp Glu Leu Lys Ala Gln Gly Trp Lys Ile His Trp Leu Gly
        35                  40                  45 act gcc gat cgt atg gaa gct caa att gta cct atg cat ggt tat gat      192
Thr Ala Asp Arg Met Glu Ala Gln Ile Val Pro Met His Gly Tyr Asp
    50                  55                  60 att tcg ttt atc aat ata agt ggt ctg cgt ggt aaa aat cta tta aca      240
Ile Ser Phe Ile Asn Ile Ser Gly Leu Arg Gly Lys Asn Leu Leu Thr
65                  70                  75                  80 acg ctt gtt atg cct ttt aaa ttg tta agg tcg ctt ttt caa gcg aga      288
Thr Leu Val Met Pro Phe Lys Leu Leu Arg Ser Leu Phe Gln Ala Arg
                85                  90                  95 cgc gtg att aaa aca gtg aaa cct gat gtt gtt ata ggc atg ggt ggc      336
Arg Val Ile Lys Thr Val Lys Pro Asp Val Val Ile Gly Met Gly Gly
            100                 105                 110 tat gca agt gct ccg ggt ggt ttg gcc gct tgg cta agt aaa ata ccg      384
Tyr Ala Ser Ala Pro Gly Gly Leu Ala Ala Trp Leu Ser Lys Ile Pro
        115                 120                 125 cta atc gtt cat gaa caa aat gct gct gcc gga tta agt aat cgc ttg      432
Leu Ile Val His Glu Gln Asn Ala Ala Ala Gly Leu Ser Asn Arg Leu
    130                 135                 140
```

```
tta gcg cgt atc gcc aat aaa gta tgc tgc gcc ttt cct aat gca ttt    480
Leu Ala Arg Ile Ala Asn Lys Val Cys Cys Ala Phe Pro Asn Ala Phe
145                 150                 155                 160 gtt agc gga att gat gtt gaa gtg gtt ggt aat cct tta cgc gcg tca    528
Val Ser Gly Ile Asp Val Glu Val Val Gly Asn Pro Leu Arg Ala Ser
            165                 170                 175 atc ggt cag caa gca ctg gtt tca gaa aat ata gat caa agc cac gaa    576
Ile Gly Gln Gln Ala Leu Val Ser Glu Asn Ile Asp Gln Ser His Glu
        180                 185                 190 ggt agt aaa aat att cta gtg gta ggt ggt agt tta ggc gct caa gtc    624
Gly Ser Lys Asn Ile Leu Val Val Gly Gly Ser Leu Gly Ala Gln Val
    195                 200                 205 tta aat aag gtg atg ccg gat agc ttt aag gat tta tca gaa agt gat    672
Leu Asn Lys Val Met Pro Asp Ser Phe Lys Asp Leu Ser Glu Ser Asp
210                 215                 220 gag aaa tat tgt ata tgg cac caa acg ggc gac aat aac caa gca cta    720
Glu Lys Tyr Cys Ile Trp His Gln Thr Gly Asp Asn Asn Gln Ala Leu
225                 230                 235                 240 gtc acc gca tct tat aaa cag gaa tat att gat act gga aaa gtg aga    768
Val Thr Ala Ser Tyr Lys Gln Glu Tyr Ile Asp Thr Gly Lys Val Arg
            245                 250                 255 gtt acc gaa ttt att act gat att gct gct gca tat cag tgg gct gat    816
Val Thr Glu Phe Ile Thr Asp Ile Ala Ala Ala Tyr Gln Trp Ala Asp
        260                 265                 270 ata gtg att tgt cgt gcg gga gcg cta acc gtt tca gaa tta gcc atg    864
Ile Val Ile Cys Arg Ala Gly Ala Leu Thr Val Ser Glu Leu Ala Met
    275                 280                 285 gca gca aca cca gcc att ttt gta cca cta ccg cat gca gta gat gat    912
Ala Ala Thr Pro Ala Ile Phe Val Pro Leu Pro His Ala Val Asp Asp
290                 295                 300 cat caa aca aaa aat gcg ttg tac ctc gta aag cga gat gca gca aag    960
His Gln Thr Lys Asn Ala Leu Tyr Leu Val Lys Arg Asp Ala Ala Lys
305                 310                 315                 320 tta ttg cca cag gca gaa cta aat aat gag agt atc acg tcg tta ata   1008
Leu Leu Pro Gln Ala Glu Leu Asn Asn Glu Ser Ile Thr Ser Leu Ile
            325                 330                 335 atc gag ctg ttt gat cag cct caa act tta gct gac atg gct aaa gct   1056
Ile Glu Leu Phe Asp Gln Pro Gln Thr Leu Ala Asp Met Ala Lys Ala
        340                 345                 350 tct ttg agt gct gca act agt gat gca agt cag aaa gta gca aaa ttg   1104
Ser Leu Ser Ala Ala Thr Ser Asp Ala Ser Gln Lys Val Ala Lys Leu
    355                 360                 365 tgc caa cag ctt tca ata tcg aat ggc gca aaa ctt aga aat aat gaa   1152
Cys Gln Gln Leu Ser Ile Ser Asn Gly Ala Lys Leu Arg Asn Asn Glu
370                 375                 380 gag aac aaa taa                                                    1164
Glu Asn Lys
385
```

<210> SEQ ID NO 16
<211> LENGTH: 387
<212> TYPE: PRT
<213> ORGANISM: Artificial Sequence
<220> FEATURE:
<223> OTHER INFORMATION: Synthetic Construct

<400> SEQUENCE: 16

```
Met Ser Leu Asn His Gly Gln Gly Asn Lys Asp Leu Ala Lys Thr Leu
1               5                   10                  15

Leu Val Met Ala Gly Gly Thr Gly Gly His Ile Phe Pro Gly Ile Ala
            20                  25                  30
```

Val Ala Asp Glu Leu Lys Ala Gln Gly Trp Lys Ile His Trp Leu Gly
            35                  40                  45

Thr Ala Asp Arg Met Glu Ala Gln Ile Val Pro Met His Gly Tyr Asp
    50                  55                  60

Ile Ser Phe Ile Asn Ile Ser Gly Leu Arg Gly Lys Asn Leu Leu Thr
65                  70                  75                  80

Thr Leu Val Met Pro Phe Lys Leu Leu Arg Ser Leu Phe Gln Ala Arg
                85                  90                  95

Arg Val Ile Lys Thr Val Lys Pro Asp Val Val Ile Gly Met Gly Gly
            100                 105                 110

Tyr Ala Ser Ala Pro Gly Gly Leu Ala Ala Trp Leu Ser Lys Ile Pro
        115                 120                 125

Leu Ile Val His Glu Gln Asn Ala Ala Ala Gly Leu Ser Asn Arg Leu
    130                 135                 140

Leu Ala Arg Ile Ala Asn Lys Val Cys Cys Ala Phe Pro Asn Ala Phe
145                 150                 155                 160

Val Ser Gly Ile Asp Val Glu Val Val Gly Asn Pro Leu Arg Ala Ser
                165                 170                 175

Ile Gly Gln Gln Ala Leu Val Ser Glu Asn Ile Asp Gln Ser His Glu
            180                 185                 190

Gly Ser Lys Asn Ile Leu Val Val Gly Gly Ser Leu Gly Ala Gln Val
        195                 200                 205

Leu Asn Lys Val Met Pro Asp Ser Phe Lys Asp Leu Ser Glu Ser Asp
    210                 215                 220

Glu Lys Tyr Cys Ile Trp His Gln Thr Gly Asp Asn Asn Gln Ala Leu
225                 230                 235                 240

Val Thr Ala Ser Tyr Lys Gln Glu Tyr Ile Asp Thr Gly Lys Val Arg
                245                 250                 255

Val Thr Glu Phe Ile Thr Asp Ile Ala Ala Ala Tyr Gln Trp Ala Asp
            260                 265                 270

Ile Val Ile Cys Arg Ala Gly Ala Leu Thr Val Ser Glu Leu Ala Met
        275                 280                 285

Ala Ala Thr Pro Ala Ile Phe Val Pro Leu Pro His Ala Val Asp Asp
    290                 295                 300

His Gln Thr Lys Asn Ala Leu Tyr Leu Val Lys Arg Asp Ala Ala Lys
305                 310                 315                 320

Leu Leu Pro Gln Ala Glu Leu Asn Asn Glu Ser Ile Thr Ser Leu Ile
                325                 330                 335

Ile Glu Leu Phe Asp Gln Pro Gln Thr Leu Ala Asp Met Ala Lys Ala
            340                 345                 350

Ser Leu Ser Ala Ala Thr Ser Asp Ala Ser Gln Lys Val Ala Lys Leu
        355                 360                 365

Cys Gln Gln Leu Ser Ile Ser Asn Gly Ala Lys Leu Arg Asn Asn Glu
    370                 375                 380

Glu Asn Lys
385

<210> SEQ ID NO 17
<211> LENGTH: 2067
<212> TYPE: DNA
<213> ORGANISM: Artificial Sequence
<220> FEATURE:
<223> OTHER INFORMATION: Codon optimized ligACp optimized for M.
      tuberculosis
<220> FEATURE:

<221> NAME/KEY: CDS
<222> LOCATION: (1)..(2067)

<400> SEQUENCE: 17

| | | | | | | | | | | | | | | | | |
|---|---|---|---|---|---|---|---|---|---|---|---|---|---|---|---|---|
| gtg | agc | gag | aag | gag | aag | aaa | ata | tcc | cag | ctg | caa | cag | caa | ctg | aac | 48 |
| Val | Ser | Glu | Lys | Glu | Lys | Lys | Ile | Ser | Gln | Leu | Gln | Gln | Gln | Leu | Asn | |
| 1 | | | | 5 | | | | | 10 | | | | | 15 | | |
| caa | tat | aac | cat | gag | tac | tat | gtc | ctc | gac | cag | cca | tcg | gtc | ccc | gat | 96 |
| Gln | Tyr | Asn | His | Glu | Tyr | Tyr | Val | Leu | Asp | Gln | Pro | Ser | Val | Pro | Asp | |
| | | | 20 | | | | | 25 | | | | | 30 | | | |
| gcg | gag | tac | gat | cgc | ctg | atg | acc | gcg | tta | atc | gat | ctg | gaa | aag | acc | 144 |
| Ala | Glu | Tyr | Asp | Arg | Leu | Met | Thr | Ala | Leu | Ile | Asp | Leu | Glu | Lys | Thr | |
| | | 35 | | | | | 40 | | | | | 45 | | | | |
| aac | ccg | gag | ttg | aag | acg | atc | gac | agt | ccg | tcg | cag | aag | gtg | ggc | ggt | 192 |
| Asn | Pro | Glu | Leu | Lys | Thr | Ile | Asp | Ser | Pro | Ser | Gln | Lys | Val | Gly | Gly | |
| | 50 | | | | | 55 | | | | | 60 | | | | | |
| cag | gcc | ctg | aag | agc | ttc | acc | caa | gtg | acg | cat | cag | ctg | ccc | atg | ctc | 240 |
| Gln | Ala | Leu | Lys | Ser | Phe | Thr | Gln | Val | Thr | His | Gln | Leu | Pro | Met | Leu | |
| 65 | | | | | 70 | | | | | 75 | | | | | 80 | |
| tcg | ctt | gac | aac | gtc | ttt | tcg | ctg | gat | gac | ttc | cac | gcc | ttc | gtc | aag | 288 |
| Ser | Leu | Asp | Asn | Val | Phe | Ser | Leu | Asp | Asp | Phe | His | Ala | Phe | Val | Lys | |
| | | | | 85 | | | | | 90 | | | | | 95 | | |
| agg | gtc | aaa | gac | cgt | ctc | aat | gac | aac | cag | gcg | atc | gtg | ttc | tgt | gcc | 336 |
| Arg | Val | Lys | Asp | Arg | Leu | Asn | Asp | Asn | Gln | Ala | Ile | Val | Phe | Cys | Ala | |
| | | | 100 | | | | | 105 | | | | | 110 | | | |
| gag | ccg | aag | ctg | gac | ggc | ctc | gcg | gta | tcg | ctc | cgc | tac | gag | cat | ggc | 384 |
| Glu | Pro | Lys | Leu | Asp | Gly | Leu | Ala | Val | Ser | Leu | Arg | Tyr | Glu | His | Gly | |
| | | 115 | | | | | 120 | | | | | 125 | | | | |
| cag | ctc | atc | cag | gcg | gcc | acg | cgg | ggc | gac | ggc | tca | gtc | ggg | gag | aat | 432 |
| Gln | Leu | Ile | Gln | Ala | Ala | Thr | Arg | Gly | Asp | Gly | Ser | Val | Gly | Glu | Asn | |
| | 130 | | | | | 135 | | | | | 140 | | | | | |
| atc | acc | acg | aac | atc | cgg | acg | atc | aag | tcc | atc | ccc | ctg | aag | ctc | atg | 480 |
| Ile | Thr | Thr | Asn | Ile | Arg | Thr | Ile | Lys | Ser | Ile | Pro | Leu | Lys | Leu | Met | |
| 145 | | | | | 150 | | | | | 155 | | | | | 160 | |
| ggc | act | ccc | ggc | aaa | gac | ttt | cca | gac | att | gtg | gaa | gtc | cgg | ggc | gaa | 528 |
| Gly | Thr | Pro | Gly | Lys | Asp | Phe | Pro | Asp | Ile | Val | Glu | Val | Arg | Gly | Glu | |
| | | | | 165 | | | | | 170 | | | | | 175 | | |
| gtg | ttc | atg | ccg | aag | gcc | tcg | ttc | gac | gcg | ctg | aac | acc | ctg | gct | aag | 576 |
| Val | Phe | Met | Pro | Lys | Ala | Ser | Phe | Asp | Ala | Leu | Asn | Thr | Leu | Ala | Lys | |
| | | | 180 | | | | | 185 | | | | | 190 | | | |
| aaa | cgg | ggg | gag | aag | ggc | ttc | gct | aac | ccg | cgg | aac | gcg | gca | gcc | ggc | 624 |
| Lys | Arg | Gly | Glu | Lys | Gly | Phe | Ala | Asn | Pro | Arg | Asn | Ala | Ala | Ala | Gly | |
| | | 195 | | | | | 200 | | | | | 205 | | | | |
| agt | ctg | cgt | cag | ctg | gac | agc | aag | atc | acg | gcc | aag | cgc | aac | ctg | gcg | 672 |
| Ser | Leu | Arg | Gln | Leu | Asp | Ser | Lys | Ile | Thr | Ala | Lys | Arg | Asn | Leu | Ala | |
| | 210 | | | | | 215 | | | | | 220 | | | | | |
| ttc | tat | gcc | tac | agc | cta | ggt | ttc | gtg | ggg | aaa | ctg | agc | gac | ggg | ggc | 720 |
| Phe | Tyr | Ala | Tyr | Ser | Leu | Gly | Phe | Val | Gly | Lys | Leu | Ser | Asp | Gly | Gly | |
| 225 | | | | | 230 | | | | | 235 | | | | | 240 | |
| gcg | gaa | agc | acc | gac | ttg | acg | aac | gac | ttt | ttc | gcg | aac | tcg | cac | cat | 768 |
| Ala | Glu | Ser | Thr | Asp | Leu | Thr | Asn | Asp | Phe | Phe | Ala | Asn | Ser | His | His | |
| | | | | 245 | | | | | 250 | | | | | 255 | | |
| gag | cga | ttg | tgt | caa | ttg | aag | cga | ctg | ggt | ttg | ccg | atg | tgt | ccg | gag | 816 |
| Glu | Arg | Leu | Cys | Gln | Leu | Lys | Arg | Leu | Gly | Leu | Pro | Met | Cys | Pro | Glu | |
| | | | 260 | | | | | 265 | | | | | 270 | | | |
| gtg | cgg | ctg | cta | gaa | tcg | gag | cag | gct | tgc | gac | gcg | ttc | tac | cag | gac | 864 |
| Val | Arg | Leu | Leu | Glu | Ser | Glu | Gln | Ala | Cys | Asp | Ala | Phe | Tyr | Gln | Asp | |
| | | 275 | | | | | 280 | | | | | 285 | | | | |
| atc | ctc | gcg | aag | cgc | tcg | gct | ctt | tca | tac | gaa | atc | gac | ggt | acc | gtt | 912 |
| Ile | Leu | Ala | Lys | Arg | Ser | Ala | Leu | Ser | Tyr | Glu | Ile | Asp | Gly | Thr | Val | |

```
                    290                 295                 300
ttg aag gtt gac gag atc tcc ctc cag aag cgc ctg ggt ttc gtg gcg        960
Leu Lys Val Asp Glu Ile Ser Leu Gln Lys Arg Leu Gly Phe Val Ala
305                 310                 315                 320 cgg gca ccg cgc tgg gcc atc gcc tac aag ttc cca gca gag gaa gag       1008
Arg Ala Pro Arg Trp Ala Ile Ala Tyr Lys Phe Pro Ala Glu Glu Glu
                325                 330                 335 ctg acc tgc gtg gag gac gta gaa ttt caa gtg ggc cgc acc ggt gcc       1056
Leu Thr Cys Val Glu Asp Val Glu Phe Gln Val Gly Arg Thr Gly Ala
            340                 345                 350 atc acc ccg gtt gcc cgc ctg aag cct gtc ttc gtg ggc ggt gtc acc       1104
Ile Thr Pro Val Ala Arg Leu Lys Pro Val Phe Val Gly Gly Val Thr
        355                 360                 365 gtg agc aac gct acc ctt cat aac cag gac gag atc aca cgt ctg ggg       1152
Val Ser Asn Ala Thr Leu His Asn Gln Asp Glu Ile Thr Arg Leu Gly
    370                 375                 380 ctg aag gtc aac gat ttc gtc gtg att cgc cgg gca ggc gac gtt att       1200
Leu Lys Val Asn Asp Phe Val Val Ile Arg Arg Ala Gly Asp Val Ile
385                 390                 395                 400 ccg cag atc gtg tcg gtg gtc ctg gac aaa agg ccg gat aac gcc gtc       1248
Pro Gln Ile Val Ser Val Val Leu Asp Lys Arg Pro Asp Asn Ala Val
                405                 410                 415 gat atc gtc ttc ccc acg tcg tgc ccg gtg tgc gac tcg gcc gtg gcc       1296
Asp Ile Val Phe Pro Thr Ser Cys Pro Val Cys Asp Ser Ala Val Ala
            420                 425                 430 aag ccc gaa ggc gag gca gtc ctg cgg tgc aca gcc ggg ctc ttc tgt       1344
Lys Pro Glu Gly Glu Ala Val Leu Arg Cys Thr Ala Gly Leu Phe Cys
        435                 440                 445 gcg gcc cag cgc aag gaa gcc atc aag cac ttc gcc tcc cgc aag gcc       1392
Ala Ala Gln Arg Lys Glu Ala Ile Lys His Phe Ala Ser Arg Lys Ala
    450                 455                 460 cac gac gtc gac gga ctg ggc gac aag ctc gtc gag cag ctt gta gac       1440
His Asp Val Asp Gly Leu Gly Asp Lys Leu Val Glu Gln Leu Val Asp
465                 470                 475                 480 gag aag ctg atc aac acc ccc gcg gat ctg ttc aag ctc acc gaa atc       1488
Glu Lys Leu Ile Asn Thr Pro Ala Asp Leu Phe Lys Leu Thr Glu Ile
                485                 490                 495 cag gtg agt acc att gac aga atg gga aag aag tct gcc acc aac ctg       1536
Gln Val Ser Thr Ile Asp Arg Met Gly Lys Lys Ser Ala Thr Asn Leu
            500                 505                 510 ata aat ggt ctg gag cag gcg aag agc act acg ctg gcg aag ttc att       1584
Ile Asn Gly Leu Glu Gln Ala Lys Ser Thr Thr Leu Ala Lys Phe Ile
        515                 520                 525 tac ggc ctg ggg atc cgg gaa gtg gga gag gcc acg gcc gcg aac ctg       1632
Tyr Gly Leu Gly Ile Arg Glu Val Gly Glu Ala Thr Ala Ala Asn Leu
    530                 535                 540 gcc aac cac ttc tac acc ctc gcc gcg atc gag agc gcc agc ttg gag       1680
Ala Asn His Phe Tyr Thr Leu Ala Ala Ile Glu Ser Ala Ser Leu Glu
545                 550                 555                 560 gat ctg cag aac gta tcc gac gtg ggt gag gtc gtg gca aag aac atc       1728
Asp Leu Gln Asn Val Ser Asp Val Gly Glu Val Val Ala Lys Asn Ile
                565                 570                 575 att aat ttc ttc aag gaa gag cac aac ctg gcg atc gtc agc ggt ttg       1776
Ile Asn Phe Phe Lys Glu Glu His Asn Leu Ala Ile Val Ser Gly Leu
            580                 585                 590 agc gaa gtg atg cac tgg ccc acc atc gag atc aag tcg gcc gag gag       1824
Ser Glu Val Met His Trp Pro Thr Ile Glu Ile Lys Ser Ala Glu Glu
        595                 600                 605 ctt cct ctg gcg gag cag atc ttc gtc ctc acc gga act ctc acc cag       1872
Leu Pro Leu Ala Glu Gln Ile Phe Val Leu Thr Gly Thr Leu Thr Gln
```

```
                                                                              -continued
Leu Pro Leu Ala Glu Gln Ile Phe Val Leu Thr Gly Thr Leu Thr Gln
        610                 615                 620 atg ggc cgc acg gag gcg aag acc gcc ttg caa tcc ctg ggc gct aag        1920
Met Gly Arg Thr Glu Ala Lys Thr Ala Leu Gln Ser Leu Gly Ala Lys
625                 630                 635                 640 gtc tcg ggc tcc gtc tcc aag aac acc cac ttc gtg gtt gcg ggc gac        1968
Val Ser Gly Ser Val Ser Lys Asn Thr His Phe Val Val Ala Gly Asp
                645                 650                 655 aag gct ggc agc aag ctg acg aag gcg cag gac ctc ggc atc tca gtc        2016
Lys Ala Gly Ser Lys Leu Thr Lys Ala Gln Asp Leu Gly Ile Ser Val
            660                 665                 670 ctg aca gag gat ggc ctg gtc gcc ctg ctg gca gag cac ggc atc acc        2064
Leu Thr Glu Asp Gly Leu Val Ala Leu Leu Ala Glu His Gly Ile Thr
        675                 680                 685 att                                                                    2067
Ile

<210> SEQ ID NO 18
<211> LENGTH: 689
<212> TYPE: PRT
<213> ORGANISM: Artificial Sequence
<220> FEATURE:
<223> OTHER INFORMATION: Synthetic Construct

<400> SEQUENCE: 18

Val Ser Glu Lys Glu Lys Lys Ile Ser Gln Leu Gln Gln Gln Leu Asn
1               5                   10                  15

Gln Tyr Asn His Glu Tyr Tyr Val Leu Asp Gln Pro Ser Val Pro Asp
            20                  25                  30

Ala Glu Tyr Asp Arg Leu Met Thr Ala Leu Ile Asp Leu Glu Lys Thr
        35                  40                  45

Asn Pro Glu Leu Lys Thr Ile Asp Ser Pro Ser Gln Lys Val Gly Gly
    50                  55                  60

Gln Ala Leu Lys Ser Phe Thr Gln Val Thr His Gln Leu Pro Met Leu
65                  70                  75                  80

Ser Leu Asp Asn Val Phe Ser Leu Asp Phe His Ala Phe Val Lys
                85                  90                  95

Arg Val Lys Asp Arg Leu Asn Asp Asn Gln Ala Ile Val Phe Cys Ala
                100                 105                 110

Glu Pro Lys Leu Asp Gly Leu Ala Val Ser Leu Arg Tyr Glu His Gly
            115                 120                 125

Gln Leu Ile Gln Ala Ala Thr Arg Gly Asp Gly Ser Val Gly Glu Asn
        130                 135                 140

Ile Thr Thr Asn Ile Arg Thr Ile Lys Ser Ile Pro Leu Lys Leu Met
145                 150                 155                 160

Gly Thr Pro Gly Lys Asp Phe Pro Asp Ile Val Glu Val Arg Gly Glu
                165                 170                 175

Val Phe Met Pro Lys Ala Ser Phe Asp Ala Leu Asn Thr Leu Ala Lys
            180                 185                 190

Lys Arg Gly Glu Lys Gly Phe Ala Asn Pro Arg Asn Ala Ala Ala Gly
        195                 200                 205

Ser Leu Arg Gln Leu Asp Ser Lys Ile Thr Ala Lys Arg Asn Leu Ala
    210                 215                 220

Phe Tyr Ala Tyr Ser Leu Gly Phe Val Gly Leu Ser Asp Gly Gly
225                 230                 235                 240

Ala Glu Ser Thr Asp Leu Thr Asn Asp Phe Phe Ala Asn Ser His His
                245                 250                 255
```

```
Glu Arg Leu Cys Gln Leu Lys Arg Leu Gly Leu Pro Met Cys Pro Glu
            260                 265                 270

Val Arg Leu Leu Glu Ser Glu Gln Ala Cys Asp Ala Phe Tyr Gln Asp
            275                 280                 285

Ile Leu Ala Lys Arg Ser Ala Leu Ser Tyr Glu Ile Asp Gly Thr Val
            290                 295                 300

Leu Lys Val Asp Glu Ile Ser Leu Gln Lys Arg Leu Gly Phe Val Ala
305                 310                 315                 320

Arg Ala Pro Arg Trp Ala Ile Ala Tyr Lys Phe Pro Ala Glu Glu Glu
                325                 330                 335

Leu Thr Cys Val Glu Asp Val Glu Phe Gln Val Gly Arg Thr Gly Ala
            340                 345                 350

Ile Thr Pro Val Ala Arg Leu Lys Pro Val Phe Val Gly Gly Val Thr
            355                 360                 365

Val Ser Asn Ala Thr Leu His Asn Gln Asp Glu Ile Thr Arg Leu Gly
            370                 375                 380

Leu Lys Val Asn Asp Phe Val Val Ile Arg Arg Ala Gly Asp Val Ile
385                 390                 395                 400

Pro Gln Ile Val Ser Val Val Leu Asp Lys Arg Pro Asp Asn Ala Val
                405                 410                 415

Asp Ile Val Phe Pro Thr Ser Cys Pro Val Cys Asp Ser Ala Val Ala
            420                 425                 430

Lys Pro Glu Gly Glu Ala Val Leu Arg Cys Thr Ala Gly Leu Phe Cys
            435                 440                 445

Ala Ala Gln Arg Lys Glu Ala Ile Lys His Phe Ala Ser Arg Lys Ala
            450                 455                 460

His Asp Val Asp Gly Leu Gly Asp Lys Leu Val Glu Gln Leu Val Asp
465                 470                 475                 480

Glu Lys Leu Ile Asn Thr Pro Ala Asp Leu Phe Lys Leu Thr Glu Ile
                485                 490                 495

Gln Val Ser Thr Ile Asp Arg Met Gly Lys Lys Ser Ala Thr Asn Leu
            500                 505                 510

Ile Asn Gly Leu Glu Gln Ala Lys Ser Thr Thr Leu Ala Lys Phe Ile
            515                 520                 525

Tyr Gly Leu Gly Ile Arg Glu Val Gly Glu Ala Thr Ala Ala Asn Leu
            530                 535                 540

Ala Asn His Phe Tyr Thr Leu Ala Ala Ile Glu Ser Ala Ser Leu Glu
545                 550                 555                 560

Asp Leu Gln Asn Val Ser Asp Val Gly Glu Val Val Ala Lys Asn Ile
                565                 570                 575

Ile Asn Phe Phe Lys Glu Glu His Asn Leu Ala Ile Val Ser Gly Leu
            580                 585                 590

Ser Glu Val Met His Trp Pro Thr Ile Glu Ile Lys Ser Ala Glu Glu
            595                 600                 605

Leu Pro Leu Ala Glu Gln Ile Phe Val Leu Thr Gly Thr Leu Thr Gln
            610                 615                 620

Met Gly Arg Thr Glu Ala Lys Thr Ala Leu Gln Ser Leu Gly Ala Lys
625                 630                 635                 640

Val Ser Gly Ser Val Ser Lys Asn Thr His Phe Val Val Ala Gly Asp
                645                 650                 655

Lys Ala Gly Ser Lys Leu Thr Lys Ala Gln Asp Leu Gly Ile Ser Val
            660                 665                 670
```

```
Leu Thr Glu Asp Gly Leu Val Ala Leu Leu Ala Glu His Gly Ile Thr
            675                 680                 685

Ile

<210> SEQ ID NO 19
<211> LENGTH: 1917
<212> TYPE: DNA
<213> ORGANISM: Colwellia psychroerythrus
<220> FEATURE:
<221> NAME/KEY: CDS
<222> LOCATION: (1)..(1917)
<220> FEATURE:
<221> NAME/KEY: misc_feature
<222> LOCATION: (556)..(556)
<223> OTHER INFORMATION: s at location 556 is g or c

<400> SEQUENCE: 19 atg gga aaa att att ggt att gac cta gga aca act aac tca tgt gtt      48
Met Gly Lys Ile Ile Gly Ile Asp Leu Gly Thr Thr Asn Ser Cys Val
1               5                   10                  15 gct gtt tta gat ggc gac agt gta cgt gtt att gaa aat gca gaa ggc      96
Ala Val Leu Asp Gly Asp Ser Val Arg Val Ile Glu Asn Ala Glu Gly
                20                  25                  30 gat cgt aca act cct tct att att ggt tat aca gcc gaa ggc gaa aca     144
Asp Arg Thr Thr Pro Ser Ile Ile Gly Tyr Thr Ala Glu Gly Glu Thr
            35                  40                  45 tta gta ggt caa cct gct aag cgt caa tct gta act aac cca gaa aac     192
Leu Val Gly Gln Pro Ala Lys Arg Gln Ser Val Thr Asn Pro Glu Asn
        50                  55                  60 act tta tat gca att aaa cgc tta atc ggt cgt cgt ttc gaa gat aaa     240
Thr Leu Tyr Ala Ile Lys Arg Leu Ile Gly Arg Arg Phe Glu Asp Lys
65                  70                  75                  80 gaa aca caa cgt gac atc gat att atg cca ttt ggt att gtt aaa gcg     288
Glu Thr Gln Arg Asp Ile Asp Ile Met Pro Phe Gly Ile Val Lys Ala
                85                  90                  95 gat aac ggt gat gct tgg gtt caa gta aaa ggc gag aaa att gct ccg     336
Asp Asn Gly Asp Ala Trp Val Gln Val Lys Gly Glu Lys Ile Ala Pro
            100                 105                 110 cca caa gtt tca gct gaa gtt ctt aag aaa atg aaa aag act gct gaa     384
Pro Gln Val Ser Ala Glu Val Leu Lys Lys Met Lys Lys Thr Ala Glu
        115                 120                 125 gac ttc tta ggt gaa acc gta act gaa gct gtt att act gta cct gct     432
Asp Phe Leu Gly Glu Thr Val Thr Glu Ala Val Ile Thr Val Pro Ala
    130                 135                 140 tac ttt aac gat tca caa cgc caa gca acg aaa gat gct ggt cgt att     480
Tyr Phe Asn Asp Ser Gln Arg Gln Ala Thr Lys Asp Ala Gly Arg Ile
145                 150                 155                 160 gct ggt ctt gaa gtc aaa cgt att atc aac gaa cct act gct gct gcc     528
Ala Gly Leu Glu Val Lys Arg Ile Ile Asn Glu Pro Thr Ala Ala Ala
                165                 170                 175 ctt gct tac ggc atg gac aaa caa gaa sgt gac aaa gtt gtt gca gtt     576
Leu Ala Tyr Gly Met Asp Lys Gln Glu Xaa Asp Lys Val Val Ala Val
            180                 185                 190 tac gat tta ggt ggt ggt aca ttc gat att tca atc att gaa att gat     624
Tyr Asp Leu Gly Gly Gly Thr Phe Asp Ile Ser Ile Ile Glu Ile Asp
        195                 200                 205 gaa atg gat ggc gaa cac act ttt gaa gta tta gcg act aac ggt gat     672
Glu Met Asp Gly Glu His Thr Phe Glu Val Leu Ala Thr Asn Gly Asp
    210                 215                 220 act cac tta ggt ggt gaa gat ttt gat aac cgt tta atc aac tac ctt     720
Thr His Leu Gly Gly Glu Asp Phe Asp Asn Arg Leu Ile Asn Tyr Leu
225                 230                 235                 240
```

```
gta gct gaa ttc aaa aaa gac caa ggc atg gac tta acg tct gat cct      768
Val Ala Glu Phe Lys Lys Asp Gln Gly Met Asp Leu Thr Ser Asp Pro
            245                 250                 255 tta gca atg cag cgt tta aaa gaa gca gca gaa aaa gct aaa tgt gaa      816
Leu Ala Met Gln Arg Leu Lys Glu Ala Ala Glu Lys Ala Lys Cys Glu
        260                 265                 270 ctt tct tca gca caa caa aca gat gta aac tta cct tac atc act gct      864
Leu Ser Ser Ala Gln Gln Thr Asp Val Asn Leu Pro Tyr Ile Thr Ala
    275                 280                 285 gat ggt tca ggt cct aag cac atg aac atc aaa gtg act cgt gct aag      912
Asp Gly Ser Gly Pro Lys His Met Asn Ile Lys Val Thr Arg Ala Lys
290                 295                 300 tta gaa tca cta gtt gaa gat atg gtt aaa gca aca tta gag ccg ctt      960
Leu Glu Ser Leu Val Glu Asp Met Val Lys Ala Thr Leu Glu Pro Leu
305                 310                 315                 320 aaa caa gcg ctt aaa gat gca gac tta tca gta agc aag att gat gat     1008
Lys Gln Ala Leu Lys Asp Ala Asp Leu Ser Val Ser Lys Ile Asp Asp
                325                 330                 335 gtt att tta gtt ggt ggt caa tct cgt atg cca cta gtt caa aaa act     1056
Val Ile Leu Val Gly Gly Gln Ser Arg Met Pro Leu Val Gln Lys Thr
            340                 345                 350 gtt act gat ttc ttc ggt aaa gag cca cgt aaa gat gtt aac cct gat     1104
Val Thr Asp Phe Phe Gly Lys Glu Pro Arg Lys Asp Val Asn Pro Asp
        355                 360                 365 gaa gca gta gct tct ggt gcg gcg att caa gcg ggt gtt ctt tct ggt     1152
Glu Ala Val Ala Ser Gly Ala Ala Ile Gln Ala Gly Val Leu Ser Gly
    370                 375                 380 gat gtg act gac gtt ctt tta tta gac gtt aca cca cta tca tta ggt     1200
Asp Val Thr Asp Val Leu Leu Leu Asp Val Thr Pro Leu Ser Leu Gly
385                 390                 395                 400 atc gaa act atg ggc ggt gtg atg act aag gtt atc gac aaa aac act     1248
Ile Glu Thr Met Gly Gly Val Met Thr Lys Val Ile Asp Lys Asn Thr
                405                 410                 415 act atc cca act aag caa tca caa act ttc tct aca gct gat gat aac     1296
Thr Ile Pro Thr Lys Gln Ser Gln Thr Phe Ser Thr Ala Asp Asp Asn
            420                 425                 430 caa gct gca gta act gtt cat gtt tgt cag ggt gag cgt aag caa gct     1344
Gln Ala Ala Val Thr Val His Val Cys Gln Gly Glu Arg Lys Gln Ala
        435                 440                 445 tca gca aac aaa tct tta ggt caa ttt aac ctt gaa ggt att gaa cca     1392
Ser Ala Asn Lys Ser Leu Gly Gln Phe Asn Leu Glu Gly Ile Glu Pro
    450                 455                 460 gca caa cgt ggt aca cca caa atc gaa gta act ttt gat att gat gct     1440
Ala Gln Arg Gly Thr Pro Gln Ile Glu Val Thr Phe Asp Ile Asp Ala
465                 470                 475                 480 gat ggt atc ttg cac gtt acg gct aaa gat aag aat act ggt aaa gag     1488
Asp Gly Ile Leu His Val Thr Ala Lys Asp Lys Asn Thr Gly Lys Glu
                485                 490                 495 caa aaa atc act atc aaa gcc tct tct ggt tta tct gat gaa gaa gta     1536
Gln Lys Ile Thr Ile Lys Ala Ser Ser Gly Leu Ser Asp Glu Glu Val
            500                 505                 510 gag cag atg gta cgt gat gca gaa gct aac gct gat gct gat gct aaa     1584
Glu Gln Met Val Arg Asp Ala Glu Ala Asn Ala Asp Ala Asp Ala Lys
        515                 520                 525 ttt gaa gag cta gta act gca cgt aat caa gct gat ggc atg att cac     1632
Phe Glu Glu Leu Val Thr Ala Arg Asn Gln Ala Asp Gly Met Ile His
    530                 535                 540 gcg act cgc aag caa gtt gaa gaa gca ggc gaa gag tta cca agc gaa     1680
Ala Thr Arg Lys Gln Val Glu Glu Ala Gly Glu Glu Leu Pro Ser Glu
```

```
                         545                 550                 555                 560
gat aaa gaa aaa att gaa gca gca tta act gag ctt gaa gaa gca gtt      1728
Asp Lys Glu Lys Ile Glu Ala Ala Leu Thr Glu Leu Glu Glu Ala Val
                 565                 570                 575 aaa ggt gat gat aaa gaa gta att gaa gct aaa act caa gca ctt atg      1776
Lys Gly Asp Asp Lys Glu Val Ile Glu Ala Lys Thr Gln Ala Leu Met
             580                 585                 590 gaa gca tca gct aag tta atg gaa att gct caa gct aaa gaa caa gct      1824
Glu Ala Ser Ala Lys Leu Met Glu Ile Ala Gln Ala Lys Glu Gln Ala
         595                 600                 605 caa agc gct cct gaa ggt gct caa gaa gct gac gca gct cct gca gac      1872
Gln Ser Ala Pro Glu Gly Ala Gln Glu Ala Asp Ala Ala Pro Ala Asp
     610                 615                 620 gat gtt gtt gat gct gag ttt gaa gaa gtt aaa gac aaa aaa taa          1917
Asp Val Val Asp Ala Glu Phe Glu Glu Val Lys Asp Lys Lys
625                 630                 635
```

<210> SEQ ID NO 20
<211> LENGTH: 638
<212> TYPE: PRT
<213> ORGANISM: Colwellia psychroerythrus
<220> FEATURE:
<221> NAME/KEY: misc_feature
<222> LOCATION: (186)..(186)
<223> OTHER INFORMATION: The 'Xaa' at location 186 stands for Gly, or Arg.

<400> SEQUENCE: 20

```
Met Gly Lys Ile Ile Gly Ile Asp Leu Gly Thr Thr Asn Ser Cys Val
1               5                   10                  15

Ala Val Leu Asp Gly Asp Ser Val Arg Val Ile Glu Asn Ala Glu Gly
            20                  25                  30

Asp Arg Thr Thr Pro Ser Ile Ile Gly Tyr Thr Ala Glu Gly Glu Thr
        35                  40                  45

Leu Val Gly Gln Pro Ala Lys Arg Gln Ser Val Thr Asn Pro Glu Asn
    50                  55                  60

Thr Leu Tyr Ala Ile Lys Arg Leu Ile Gly Arg Arg Phe Glu Asp Lys
65                  70                  75                  80

Glu Thr Gln Arg Asp Ile Asp Ile Met Pro Phe Gly Ile Val Lys Ala
                85                  90                  95

Asp Asn Gly Asp Ala Trp Val Gln Val Lys Gly Glu Lys Ile Ala Pro
            100                 105                 110

Pro Gln Val Ser Ala Glu Val Leu Lys Lys Met Lys Lys Thr Ala Glu
        115                 120                 125

Asp Phe Leu Gly Glu Thr Val Thr Glu Ala Val Ile Thr Val Pro Ala
    130                 135                 140

Tyr Phe Asn Asp Ser Gln Arg Gln Ala Thr Lys Asp Ala Gly Arg Ile
145                 150                 155                 160

Ala Gly Leu Glu Val Lys Arg Ile Ile Asn Glu Pro Thr Ala Ala Ala
                165                 170                 175

Leu Ala Tyr Gly Met Asp Lys Gln Glu Xaa Asp Lys Val Val Ala Val
            180                 185                 190

Tyr Asp Leu Gly Gly Gly Thr Phe Asp Ile Ser Ile Ile Glu Ile Asp
        195                 200                 205

Glu Met Asp Gly Glu His Thr Phe Glu Val Leu Ala Thr Asn Gly Asp
    210                 215                 220

Thr His Leu Gly Gly Glu Asp Phe Asp Asn Arg Leu Ile Asn Tyr Leu
225                 230                 235                 240
```

```
Val Ala Glu Phe Lys Lys Asp Gln Gly Met Asp Leu Thr Ser Asp Pro
                245                 250                 255

Leu Ala Met Gln Arg Leu Lys Glu Ala Ala Glu Lys Ala Lys Cys Glu
            260                 265                 270

Leu Ser Ser Ala Gln Gln Thr Asp Val Asn Leu Pro Tyr Ile Thr Ala
        275                 280                 285

Asp Gly Ser Gly Pro Lys His Met Asn Ile Lys Val Thr Arg Ala Lys
    290                 295                 300

Leu Glu Ser Leu Val Glu Asp Met Val Lys Ala Thr Leu Glu Pro Leu
305                 310                 315                 320

Lys Gln Ala Leu Lys Asp Ala Asp Leu Ser Val Ser Lys Ile Asp Asp
                325                 330                 335

Val Ile Leu Val Gly Gly Gln Ser Arg Met Pro Leu Val Gln Lys Thr
            340                 345                 350

Val Thr Asp Phe Phe Gly Lys Glu Pro Arg Lys Asp Val Asn Pro Asp
        355                 360                 365

Glu Ala Val Ala Ser Gly Ala Ala Ile Gln Ala Gly Val Leu Ser Gly
    370                 375                 380

Asp Val Thr Asp Val Leu Leu Leu Asp Val Thr Pro Leu Ser Leu Gly
385                 390                 395                 400

Ile Glu Thr Met Gly Gly Val Met Thr Lys Val Ile Asp Lys Asn Thr
                405                 410                 415

Thr Ile Pro Thr Lys Gln Ser Gln Thr Phe Ser Thr Ala Asp Asp Asn
            420                 425                 430

Gln Ala Ala Val Thr Val His Val Cys Gln Gly Glu Arg Lys Gln Ala
        435                 440                 445

Ser Ala Asn Lys Ser Leu Gly Gln Phe Asn Leu Glu Gly Ile Glu Pro
    450                 455                 460

Ala Gln Arg Gly Thr Pro Gln Ile Glu Val Thr Phe Asp Ile Asp Ala
465                 470                 475                 480

Asp Gly Ile Leu His Val Thr Ala Lys Asp Lys Asn Thr Gly Lys Glu
                485                 490                 495

Gln Lys Ile Thr Ile Lys Ala Ser Ser Gly Leu Ser Asp Glu Glu Val
            500                 505                 510

Glu Gln Met Val Arg Asp Ala Glu Ala Asn Ala Asp Ala Asp Ala Lys
        515                 520                 525

Phe Glu Glu Leu Val Thr Ala Arg Asn Gln Ala Asp Gly Met Ile His
    530                 535                 540

Ala Thr Arg Lys Gln Val Glu Glu Ala Gly Glu Glu Leu Pro Ser Glu
545                 550                 555                 560

Asp Lys Glu Lys Ile Glu Ala Ala Leu Thr Glu Leu Glu Glu Ala Val
                565                 570                 575

Lys Gly Asp Asp Lys Glu Val Ile Glu Ala Lys Thr Gln Ala Leu Met
            580                 585                 590

Glu Ala Ser Ala Lys Leu Met Glu Ile Ala Gln Ala Lys Glu Gln Ala
        595                 600                 605

Gln Ser Ala Pro Glu Gly Ala Gln Glu Ala Asp Ala Ala Pro Ala Asp
    610                 615                 620

Asp Val Val Asp Ala Glu Phe Glu Glu Val Lys Asp Lys Lys
625                 630                 635

<210> SEQ ID NO 21
<211> LENGTH: 1220
```

-continued

```
<212> TYPE: DNA
<213> ORGANISM: Artificial Sequence
<220> FEATURE:
<223> OTHER INFORMATION: tyrS hybrid
<220> FEATURE:
<221> NAME/KEY: CDS
<222> LOCATION: (11)..(1207)

<400> SEQUENCE: 21
tataaatata atg tcg agc ttt aac caa gca ttc gcc gaa cta aaa cgc          49
           Met Ser Ser Phe Asn Gln Ala Phe Ala Glu Leu Lys Arg
           1               5                   10 gga gca gaa gaa ata tta gta gaa gaa gaa tta tta aca aag ctt aag         97
Gly Ala Glu Glu Ile Leu Val Glu Glu Glu Leu Leu Thr Lys Leu Lys
15                  20                  25 aca ggt aag ccg cta aaa atc aaa gcg ggt ttt gat cct act gcg cct        145
Thr Gly Lys Pro Leu Lys Ile Lys Ala Gly Phe Asp Pro Thr Ala Pro
30                  35                  40                  45 gac tta cat tta ggc cac acg gta tta att aac aag ctt cgt caa ttc        193
Asp Leu His Leu Gly His Thr Val Leu Ile Asn Lys Leu Arg Gln Phe
                50                  55                  60 caa caa tta ggt cat gaa gtt att ttc ttg att ggt gac ttc acc gga        241
Gln Gln Leu Gly His Glu Val Ile Phe Leu Ile Gly Asp Phe Thr Gly
            65                  70                  75 atg att ggt gat cca acg ggt aaa aat gtg acg cgt aag gca ctc act        289
Met Ile Gly Asp Pro Thr Gly Lys Asn Val Thr Arg Lys Ala Leu Thr
    80                  85                  90 aaa gaa gac gta tta gcc aat gct gaa acg tat aaa gag caa gtc ttt        337
Lys Glu Asp Val Leu Ala Asn Ala Glu Thr Tyr Lys Glu Gln Val Phe
95                  100                 105 aaa ata tta gat ccc gct aaa aca acc gtt gcc ttt aac tct act tgg        385
Lys Ile Leu Asp Pro Ala Lys Thr Thr Val Ala Phe Asn Ser Thr Trp
110                 115                 120                 125 atg gat aaa tta ggc gcg gca ggt atg tta caa ctt gcc tct cgt caa        433
Met Asp Lys Leu Gly Ala Ala Gly Met Leu Gln Leu Ala Ser Arg Gln
                130                 135                 140 acg gtt gcc cgt atg atg gag cgt gac gac ttt aaa aaa cgt tat gct        481
Thr Val Ala Arg Met Met Glu Arg Asp Asp Phe Lys Lys Arg Tyr Ala
            145                 150                 155 aac ggc cag gcc att gct att cat gag ttt atg tac cct tta gta caa        529
Asn Gly Gln Ala Ile Ala Ile His Glu Phe Met Tyr Pro Leu Val Gln
        160                 165                 170 ggt tgg gat tca gtt gcg ctt gag gct gat gtt gag ctg ggt ggt acc        577
Gly Trp Asp Ser Val Ala Leu Glu Ala Asp Val Glu Leu Gly Gly Thr
    175                 180                 185 gac caa aag ttt aat tta tta atg ggt cgt gag tta caa aaa tct gaa        625
Asp Gln Lys Phe Asn Leu Leu Met Gly Arg Glu Leu Gln Lys Ser Glu
190                 195                 200                 205 ggc cag cgt cca caa aca gta tta atg atg cca tta ctt gaa ggc cta        673
Gly Gln Arg Pro Gln Thr Val Leu Met Met Pro Leu Leu Glu Gly Leu
                210                 215                 220 gat ggc gtt cag aaa atg tct aag tca tta ggc aac tac att ggc att        721
Asp Gly Val Gln Lys Met Ser Lys Ser Leu Gly Asn Tyr Ile Gly Ile
            225                 230                 235 act gat acg cct acc gac atg ttt ggc aaa ata atg tca att tca gat        769
Thr Asp Thr Pro Thr Asp Met Phe Gly Lys Ile Met Ser Ile Ser Asp
        240                 245                 250 gta tta atg tgg cgt tac tac gag tta ctt agc ttt aaa ccg ctt gaa        817
Val Leu Met Trp Arg Tyr Tyr Glu Leu Leu Ser Phe Lys Pro Leu Glu
    255                 260                 265 gaa att gaa ggt tat aaa acc gag ata gaa aat ggc aaa aat cct cgt        865
```

```
Glu Ile Glu Gly Tyr Lys Thr Glu Ile Glu Asn Gly Lys Asn Pro Arg
270                 275                 280                 285 gat gtt aaa att gat tta gcc aaa gaa ttg att gct cgt ttt cat gat      913
Asp Val Lys Ile Asp Leu Ala Lys Glu Leu Ile Ala Arg Phe His Asp
                290                 295                 300 gaa gct gct gca caa gct gcc cat gat gaa ttc atc aat cgt ttc caa      961
Glu Ala Ala Ala Gln Ala Ala His Asp Glu Phe Ile Asn Arg Phe Gln
            305                 310                 315 aaa ggt gcg tta cct gat gat atg ccg gaa tta acg att acc act gaa     1009
Lys Gly Ala Leu Pro Asp Asp Met Pro Glu Leu Thr Ile Thr Thr Glu
        320                 325                 330 aat ggt gaa ata gcc att gct aac ttg ctt aaa gat gca gga tta gtc     1057
Asn Gly Glu Ile Ala Ile Ala Asn Leu Leu Lys Asp Ala Gly Leu Val
    335                 340                 345 ggt agt act tct gat gcc ttt aga atg atc aaa caa ggg gcg gct aaa     1105
Gly Ser Thr Ser Asp Ala Phe Arg Met Ile Lys Gln Gly Ala Ala Lys
350                 355                 360                 365 att gat agc gaa aaa gta act gac cgt agc tta gtt att agc gct ggc     1153
Ile Asp Ser Glu Lys Val Thr Asp Arg Ser Leu Val Ile Ser Ala Gly
                370                 375                 380 acg acg gca gtt tat caa gtc ggc aaa cgt aaa ttt gct cgt att acc     1201
Thr Thr Ala Val Tyr Gln Val Gly Lys Arg Lys Phe Ala Arg Ile Thr
            385                 390                 395 ata aaa taaggggttg taa                                              1220
Ile Lys <210> SEQ ID NO 22
<211> LENGTH: 399
<212> TYPE: PRT
<213> ORGANISM: Artificial Sequence
<220> FEATURE:
<223> OTHER INFORMATION: Synthetic Construct

<400> SEQUENCE: 22

Met Ser Ser Phe Asn Gln Ala Phe Ala Glu Leu Lys Arg Gly Ala Glu
1               5                   10                  15

Glu Ile Leu Val Glu Glu Glu Leu Leu Thr Lys Leu Lys Thr Gly Lys
                20                  25                  30

Pro Leu Lys Ile Lys Ala Gly Phe Asp Pro Thr Ala Pro Asp Leu His
            35                  40                  45

Leu Gly His Thr Val Leu Ile Asn Lys Leu Arg Gln Phe Gln Gln Leu
        50                  55                  60

Gly His Glu Val Ile Phe Leu Ile Gly Asp Phe Thr Gly Met Ile Gly
65                  70                  75                  80

Asp Pro Thr Gly Lys Asn Val Thr Arg Lys Ala Leu Thr Lys Glu Asp
                85                  90                  95

Val Leu Ala Asn Ala Glu Thr Tyr Lys Glu Gln Val Phe Lys Ile Leu
            100                 105                 110

Asp Pro Ala Lys Thr Thr Val Ala Phe Asn Ser Thr Trp Met Asp Lys
        115                 120                 125

Leu Gly Ala Ala Gly Met Leu Gln Leu Ala Ser Arg Gln Thr Val Ala
130                 135                 140

Arg Met Met Glu Arg Asp Asp Phe Lys Lys Arg Tyr Ala Asn Gly Gln
145                 150                 155                 160

Ala Ile Ala Ile His Glu Phe Met Tyr Pro Leu Val Gln Gly Trp Asp
                165                 170                 175

Ser Val Ala Leu Glu Ala Asp Val Glu Leu Gly Gly Thr Asp Gln Lys
            180                 185                 190
```

```
Phe Asn Leu Leu Met Gly Arg Glu Leu Gln Lys Ser Glu Gly Gln Arg
            195                 200                 205
Pro Gln Thr Val Leu Met Met Pro Leu Leu Glu Gly Leu Asp Gly Val
    210                 215                 220
Gln Lys Met Ser Lys Ser Leu Gly Asn Tyr Ile Gly Ile Thr Asp Thr
225                 230                 235                 240
Pro Thr Asp Met Phe Gly Lys Ile Met Ser Ile Ser Asp Val Leu Met
                245                 250                 255
Trp Arg Tyr Tyr Glu Leu Leu Ser Phe Lys Pro Leu Glu Glu Ile Glu
            260                 265                 270
Gly Tyr Lys Thr Glu Ile Glu Asn Gly Lys Asn Pro Arg Asp Val Lys
        275                 280                 285
Ile Asp Leu Ala Lys Glu Leu Ile Ala Arg Phe His Asp Glu Ala Ala
    290                 295                 300
Ala Gln Ala Ala His Asp Glu Phe Ile Asn Arg Phe Gln Lys Gly Ala
305                 310                 315                 320
Leu Pro Asp Asp Met Pro Glu Leu Thr Ile Thr Thr Glu Asn Gly Glu
                325                 330                 335
Ile Ala Ile Ala Asn Leu Leu Lys Asp Ala Gly Leu Val Gly Ser Thr
            340                 345                 350
Ser Asp Ala Phe Arg Met Ile Lys Gln Gly Ala Ala Lys Ile Asp Ser
        355                 360                 365
Glu Lys Val Thr Asp Arg Ser Leu Val Ile Ser Ala Gly Thr Thr Ala
    370                 375                 380
Val Tyr Gln Val Gly Lys Arg Lys Phe Ala Arg Ile Thr Ile Lys
385                 390                 395

<210> SEQ ID NO 23
<211> LENGTH: 741
<212> TYPE: DNA
<213> ORGANISM: Artificial Sequence
<220> FEATURE:
<223> OTHER INFORMATION: cmk hybrid
<220> FEATURE:
<221> NAME/KEY: CDS
<222> LOCATION: (51)..(731)

<400> SEQUENCE: 23
aagtctagaa gatgtcgaaa aacttgtaca gtttatgcag gaatttgaga atg aac      56
                                                         Met Asn
                                                           1 aat agc aca cca gtt ata acc att gat ggc cca agt ggg gct ggt aaa    104
Asn Ser Thr Pro Val Ile Thr Ile Asp Gly Pro Ser Gly Ala Gly Lys
        5                  10                  15 gga acc gtt gca agg ata gtt gcg gac caa tta ggt tgg cac ctt ctt    152
Gly Thr Val Ala Arg Ile Val Ala Asp Gln Leu Gly Trp His Leu Leu
     20                  25                  30 gac agt ggg gct att tac cgc gtc tta gct gtt gcc att caa cat cac    200
Asp Ser Gly Ala Ile Tyr Arg Val Leu Ala Val Ala Ile Gln His His
 35                  40                  45                  50 caa ctt tca tta gat gat gaa gag cct ctt atc cct atg gct gca cat    248
Gln Leu Ser Leu Asp Asp Glu Glu Pro Leu Ile Pro Met Ala Ala His
                 55                  60                  65 tta gat gtt caa ttt gaa att aat agt caa ggt gaa gct aaa gtt att    296
Leu Asp Val Gln Phe Glu Ile Asn Ser Gln Gly Glu Ala Lys Val Ile
             70                  75                  80 tta gaa ggt gaa aat gtt act gaa att att cgt act gaa gaa gtt ggc    344
Leu Glu Gly Glu Asn Val Thr Glu Ile Ile Arg Thr Glu Glu Val Gly
```

```
gga tta gca tcg aaa gta gca gca ttt cca cgt gtt aga gaa gcg cta      392
Gly Leu Ala Ser Lys Val Ala Ala Phe Pro Arg Val Arg Glu Ala Leu
        100                 105                 110 tta cga aga caa cgt gca ttt agc gtt agc cct ggc tta att gca gat      440
Leu Arg Arg Gln Arg Ala Phe Ser Val Ser Pro Gly Leu Ile Ala Asp
115                 120                 125                 130 ggt cgc gac atg gga acc gtt gtt ttt ccg aaa gct cca gta aaa ata      488
Gly Arg Asp Met Gly Thr Val Val Phe Pro Lys Ala Pro Val Lys Ile
                    135                 140                 145 ttt tta act gct agt gct gaa gaa cga gct gac cga aga ttt aat cag      536
Phe Leu Thr Ala Ser Ala Glu Glu Arg Ala Asp Arg Arg Phe Asn Gln
                150                 155                 160 ttg aaa gaa aaa gga att gat gtt aac atc ggg cgc ctt ttg gat gac      584
Leu Lys Glu Lys Gly Ile Asp Val Asn Ile Gly Arg Leu Leu Asp Asp
            165                 170                 175 ata cgt caa cga gat gag cga gat caa aac cgc aag gta gct cct ctt      632
Ile Arg Gln Arg Asp Glu Arg Asp Gln Asn Arg Lys Val Ala Pro Leu
        180                 185                 190 atc ccg gca gaa gga gcg tta act att gat tct act gat att tct att      680
Ile Pro Ala Glu Gly Ala Leu Thr Ile Asp Ser Thr Asp Ile Ser Ile
195                 200                 205                 210 aca gaa gtc gtc aat aaa atc ctt atg ttt gcc aat ggc aaa tta acg      728
Thr Glu Val Val Asn Lys Ile Leu Met Phe Ala Asn Gly Lys Leu Thr
                    215                 220                 225 tag atattttagc                                                       741
```

<210> SEQ ID NO 24
<211> LENGTH: 226
<212> TYPE: PRT
<213> ORGANISM: Artificial Sequence
<220> FEATURE:
<223> OTHER INFORMATION: Synthetic Construct

<400> SEQUENCE: 24

```
Met Asn Asn Ser Thr Pro Val Ile Thr Ile Asp Gly Pro Ser Gly Ala
1               5                   10                  15

Gly Lys Gly Thr Val Ala Arg Ile Val Ala Asp Gln Leu Gly Trp His
            20                  25                  30

Leu Leu Asp Ser Gly Ala Ile Tyr Arg Val Leu Ala Val Ala Ile Gln
        35                  40                  45

His His Gln Leu Ser Leu Asp Asp Glu Glu Pro Leu Ile Pro Met Ala
    50                  55                  60

Ala His Leu Asp Val Gln Phe Glu Ile Asn Ser Gln Gly Glu Ala Lys
65                  70                  75                  80

Val Ile Leu Glu Gly Glu Asn Val Thr Glu Ile Ile Arg Thr Glu Glu
                85                  90                  95

Val Gly Gly Leu Ala Ser Lys Val Ala Ala Phe Pro Arg Val Arg Glu
            100                 105                 110

Ala Leu Leu Arg Arg Gln Arg Ala Phe Ser Val Ser Pro Gly Leu Ile
        115                 120                 125

Ala Asp Gly Arg Asp Met Gly Thr Val Val Phe Pro Lys Ala Pro Val
    130                 135                 140

Lys Ile Phe Leu Thr Ala Ser Ala Glu Glu Arg Ala Asp Arg Arg Phe
145                 150                 155                 160

Asn Gln Leu Lys Glu Lys Gly Ile Asp Val Asn Ile Gly Arg Leu Leu
                165                 170                 175
```

```
Asp Asp Ile Arg Gln Arg Asp Glu Arg Asp Gln Asn Arg Lys Val Ala
            180                 185                 190

Pro Leu Ile Pro Ala Glu Gly Ala Leu Thr Ile Asp Ser Thr Asp Ile
        195                 200                 205

Ser Ile Thr Glu Val Val Asn Lys Ile Leu Met Phe Ala Asn Gly Lys
    210                 215                 220

Leu Thr
225

<210> SEQ ID NO 25
<211> LENGTH: 1937
<212> TYPE: DNA
<213> ORGANISM: Artificial Sequence
<220> FEATURE:
<223> OTHER INFORMATION: dnaKsf hybrid
<220> FEATURE:
<221> NAME/KEY: CDS
<222> LOCATION: (11)..(1927)

<400> SEQUENCE: 25
```

| | | | | | | | | | | | | | | | | |
|---|---|---|---|---|---|---|---|---|---|---|---|---|---|---|---|---|
| ggagaatcaa | atg | gga | aaa | att | att | ggt | atc | gat | tta | ggc | aca | aca | aac | | | 49 |
| | Met | Gly | Lys | Ile | Ile | Gly | Ile | Asp | Leu | Gly | Thr | Thr | Asn | | | |
| | 1 | | | 5 | | | | | 10 | | | | | | | |
| tcg | tgt | gta | gca | gtc | ctt | gat | ggc | ggc | aaa | gca | cgc | gta | att | gaa | aac | 97 |
| Ser | Cys | Val | Ala | Val | Leu | Asp | Gly | Gly | Lys | Ala | Arg | Val | Ile | Glu | Asn | |
| | 15 | | | | 20 | | | | | 25 | | | | | | |
| gca | gag | ggt | gat | cgc | aca | acc | cca | tca | att | atc | gct | tat | acc | gat | gat | 145 |
| Ala | Glu | Gly | Asp | Arg | Thr | Thr | Pro | Ser | Ile | Ile | Ala | Tyr | Thr | Asp | Asp | |
| 30 | | | | | 35 | | | | | 40 | | | | | 45 | |
| gaa | att | att | gta | ggc | cag | cca | gca | aag | cgt | cag | gct | gta | acc | aac | cca | 193 |
| Glu | Ile | Ile | Val | Gly | Gln | Pro | Ala | Lys | Arg | Gln | Ala | Val | Thr | Asn | Pro | |
| | | | | 50 | | | | | 55 | | | | | 60 | | |
| aca | aac | aca | ttc | ttt | gcc | atc | aag | cgt | tta | atc | ggt | cgt | cgt | ttt | aaa | 241 |
| Thr | Asn | Thr | Phe | Phe | Ala | Ile | Lys | Arg | Leu | Ile | Gly | Arg | Arg | Phe | Lys | |
| | | | 65 | | | | | 70 | | | | | 75 | | | |
| gat | gac | gaa | gtt | caa | cgt | gat | gtg | aac | atc | atg | cca | ttc | aaa | att | atc | 289 |
| Asp | Asp | Glu | Val | Gln | Arg | Asp | Val | Asn | Ile | Met | Pro | Phe | Lys | Ile | Ile | |
| | | 80 | | | | | 85 | | | | | 90 | | | | |
| gca | gct | gat | aat | ggt | gat | gca | tgg | gtt | gag | tca | cgt | ggt | aac | aaa | atg | 337 |
| Ala | Ala | Asp | Asn | Gly | Asp | Ala | Trp | Val | Glu | Ser | Arg | Gly | Asn | Lys | Met | |
| | 95 | | | | | 100 | | | | | 105 | | | | | |
| gca | cca | cca | caa | gtt | tca | gct | gaa | atc | ttg | aaa | aag | atg | aaa | aag | act | 385 |
| Ala | Pro | Pro | Gln | Val | Ser | Ala | Glu | Ile | Leu | Lys | Lys | Met | Lys | Lys | Thr | |
| 110 | | | | | 115 | | | | | 120 | | | | | 125 | |
| gct | gaa | gac | ttt | tta | ggt | gaa | gaa | gtg | act | gaa | gcg | gtt | att | acc | gtt | 433 |
| Ala | Glu | Asp | Phe | Leu | Gly | Glu | Glu | Val | Thr | Glu | Ala | Val | Ile | Thr | Val | |
| | | | | 130 | | | | | 135 | | | | | 140 | | |
| cct | gct | tac | ttt | aac | gat | tca | caa | cgt | caa | gcc | act | aaa | gat | gct | ggt | 481 |
| Pro | Ala | Tyr | Phe | Asn | Asp | Ser | Gln | Arg | Gln | Ala | Thr | Lys | Asp | Ala | Gly | |
| | | | 145 | | | | | 150 | | | | | 155 | | | |
| cgt | atc | gca | ggt | ctt | gat | gtt | aag | cgt | att | atc | aac | gaa | cct | act | gct | 529 |
| Arg | Ile | Ala | Gly | Leu | Asp | Val | Lys | Arg | Ile | Ile | Asn | Glu | Pro | Thr | Ala | |
| | | 160 | | | | | 165 | | | | | 170 | | | | |
| gct | gca | ctt | gca | tac | ggt | atc | gac | aag | aaa | caa | ggc | gac | aac | att | gtt | 577 |
| Ala | Ala | Leu | Ala | Tyr | Gly | Ile | Asp | Lys | Lys | Gln | Gly | Asp | Asn | Ile | Val | |
| | 175 | | | | | 180 | | | | | 185 | | | | | |
| gct | gta | tac | gat | tta | ggt | ggt | ggt | aca | ttc | gat | atc | tct | atc | atc | gaa | 625 |
| Ala | Val | Tyr | Asp | Leu | Gly | Gly | Gly | Thr | Phe | Asp | Ile | Ser | Ile | Ile | Glu | |
| 190 | | | | | 195 | | | | | 200 | | | | | 205 | |
| att | gac | agc | aac | gat | ggt | gac | caa | aca | ttt | gaa | gta | cta | gca | acc | aat | 673 |
| Ile | Asp | Ser | Asn | Asp | Gly | Asp | Gln | Thr | Phe | Glu | Val | Leu | Ala | Thr | Asn | |

|     |     |
| --- | --- |
| ggt gat act cac tta ggt ggt gaa gac ttt gat aac cgt atg att aac<br>Gly Asp Thr His Leu Gly Gly Glu Asp Phe Asp Asn Arg Met Ile Asn<br>225 230 235 | 721 |
| tat tta gct gat gaa ttc aaa aaa gac caa ggc tta gat ctt cgt aga<br>Tyr Leu Ala Asp Glu Phe Lys Lys Asp Gln Gly Leu Asp Leu Arg Arg<br>240 245 250 | 769 |
| gat cct tta gca atg caa cgt ttg aaa gaa gcc gct gaa aaa gca aaa<br>Asp Pro Leu Ala Met Gln Arg Leu Lys Glu Ala Ala Glu Lys Ala Lys<br>255 260 265 | 817 |
| atc gag ctt tca agc act aac cac act gaa gtt aac ttg cct tac atc<br>Ile Glu Leu Ser Ser Thr Asn His Thr Glu Val Asn Leu Pro Tyr Ile<br>270 275 280 285 | 865 |
| act gct gat gca tca ggt cct aag cat tta gtg gtt aaa att act cgt<br>Thr Ala Asp Ala Ser Gly Pro Lys His Leu Val Val Lys Ile Thr Arg<br>290 295 300 | 913 |
| gct aag tta gag tca tta gtt gaa gat tta att caa cgt act cta gag<br>Ala Lys Leu Glu Ser Leu Val Glu Asp Leu Ile Gln Arg Thr Leu Glu<br>305 310 315 | 961 |
| ccg ctt aaa gtt gca cta gct gat gct gat tta tca ata tca gat atc<br>Pro Leu Lys Val Ala Leu Ala Asp Ala Asp Leu Ser Ile Ser Asp Ile<br>320 325 330 | 1009 |
| aat gaa gtg att ctt gtg ggt ggt cag act cgt atg cct aaa gta caa<br>Asn Glu Val Ile Leu Val Gly Gly Gln Thr Arg Met Pro Lys Val Gln<br>335 340 345 | 1057 |
| gaa gca gtc act aac ttc ttt ggc aaa gag cct cgt aaa gat gtt aac<br>Glu Ala Val Thr Asn Phe Phe Gly Lys Glu Pro Arg Lys Asp Val Asn<br>350 355 360 365 | 1105 |
| cct gat gaa gcg gtt gct gtt ggt gcg gcg att cag gct ggc gta ctt<br>Pro Asp Glu Ala Val Ala Val Gly Ala Ala Ile Gln Ala Gly Val Leu<br>370 375 380 | 1153 |
| tct ggt gaa gtg aaa gac gta ctt cta ctt gac gtt acc cca cta tct<br>Ser Gly Glu Val Lys Asp Val Leu Leu Leu Asp Val Thr Pro Leu Ser<br>385 390 395 | 1201 |
| ctt ggt att gaa acc atg ggc agt gtg atg aca aag ctt atc gag aag<br>Leu Gly Ile Glu Thr Met Gly Ser Val Met Thr Lys Leu Ile Glu Lys<br>400 405 410 | 1249 |
| aac acc act atc ccg act aaa gct cag caa gta ttc tca aca gct gac<br>Asn Thr Thr Ile Pro Thr Lys Ala Gln Gln Val Phe Ser Thr Ala Asp<br>415 420 425 | 1297 |
| gac aac caa agt gcc gtg act att cac gta ctt caa ggt gaa cgt aag<br>Asp Asn Gln Ser Ala Val Thr Ile His Val Leu Gln Gly Glu Arg Lys<br>430 435 440 445 | 1345 |
| caa gcg agt gct aac aag tca tta ggt caa ttt aac ctt gaa ggt att<br>Gln Ala Ser Ala Asn Lys Ser Leu Gly Gln Phe Asn Leu Glu Gly Ile<br>450 455 460 | 1393 |
| gag cca gca cca cgt ggc caa cca cag gtt gaa gtg atg ttc gac att<br>Glu Pro Ala Pro Arg Gly Gln Pro Gln Val Glu Val Met Phe Asp Ile<br>465 470 475 | 1441 |
| gat gct gat ggt atc tta cat gtg tct gca aca gac aag aaa aca ggt<br>Asp Ala Asp Gly Ile Leu His Val Ser Ala Thr Asp Lys Lys Thr Gly<br>480 485 490 | 1489 |
| aag aaa caa aac att act atc aaa gcc tct tca ggt tta tct gat gaa<br>Lys Lys Gln Asn Ile Thr Ile Lys Ala Ser Ser Gly Leu Ser Asp Glu<br>495 500 505 | 1537 |
| gaa gtt gaa caa atg gta cgt gat gca gaa gct cat gct gat gaa gat<br>Glu Val Glu Gln Met Val Arg Asp Ala Glu Ala His Ala Asp Glu Asp<br>510 515 520 525 | 1585 |
| gct aaa ttt gaa gag tta gtt aaa gcg cgt aat caa gca gat ggt tta<br> | 1633 |

```
Ala Lys Phe Glu Glu Leu Val Lys Ala Arg Asn Gln Ala Asp Gly Leu
                530                 535                 540 gct cat tca act aaa aaa caa gtt gaa gaa gct ggc gat gca cta gct      1681
Ala His Ser Thr Lys Lys Gln Val Glu Glu Ala Gly Asp Ala Leu Ala
            545                 550                 555 agt gac gaa aaa gaa aag att gaa gca gca atc gca act tta gaa act      1729
Ser Asp Glu Lys Glu Lys Ile Glu Ala Ala Ile Ala Thr Leu Glu Thr
        560                 565                 570 gcc ata aaa ggc aaa gat aaa gaa gcc att gat aca gca act caa gcg      1777
Ala Ile Lys Gly Lys Asp Lys Glu Ala Ile Asp Thr Ala Thr Gln Ala
    575                 580                 585 cta atc gaa gcg tct gct aag tta atg gaa att gct caa gct aaa gct      1825
Leu Ile Glu Ala Ser Ala Lys Leu Met Glu Ile Ala Gln Ala Lys Ala
590                 595                 600                 605 caa ggt gaa gca gaa ggt caa gcg cac gat gct ggc caa gaa aag cct      1873
Gln Gly Glu Ala Glu Gly Gln Ala His Asp Ala Gly Gln Glu Lys Pro
                610                 615                 620 gct gat gat gtt gtt gat gct gag ttc gaa gaa gtt aaa gac gac aaa      1921
Ala Asp Asp Val Val Asp Ala Glu Phe Glu Glu Val Lys Asp Asp Lys
            625                 630                 635 aaa taa ataatctttt                                                    1937
Lys

<210> SEQ ID NO 26
<211> LENGTH: 638
<212> TYPE: PRT
<213> ORGANISM: Artificial Sequence
<220> FEATURE:
<223> OTHER INFORMATION: Synthetic Construct

<400> SEQUENCE: 26

Met Gly Lys Ile Ile Gly Ile Asp Leu Gly Thr Thr Asn Ser Cys Val
1               5                   10                  15

Ala Val Leu Asp Gly Gly Lys Ala Arg Val Ile Glu Asn Ala Glu Gly
            20                  25                  30

Asp Arg Thr Thr Pro Ser Ile Ile Ala Tyr Thr Asp Glu Ile Ile
        35                  40                  45

Val Gly Gln Pro Ala Lys Arg Gln Ala Val Thr Asn Pro Thr Asn Thr
    50                  55                  60

Phe Phe Ala Ile Lys Arg Leu Ile Gly Arg Arg Phe Lys Asp Asp Glu
65                  70                  75                  80

Val Gln Arg Asp Val Asn Ile Met Pro Phe Lys Ile Ala Ala Asp
                85                  90                  95

Asn Gly Asp Ala Trp Val Glu Ser Arg Gly Asn Lys Met Ala Pro Pro
            100                 105                 110

Gln Val Ser Ala Glu Ile Leu Lys Lys Met Lys Lys Thr Ala Glu Asp
        115                 120                 125

Phe Leu Gly Glu Glu Val Thr Glu Ala Val Ile Thr Val Pro Ala Tyr
    130                 135                 140

Phe Asn Asp Ser Gln Arg Gln Ala Thr Lys Asp Ala Gly Arg Ile Ala
145                 150                 155                 160

Gly Leu Asp Val Lys Arg Ile Ile Asn Glu Pro Thr Ala Ala Leu
                165                 170                 175

Ala Tyr Gly Ile Asp Lys Lys Gln Gly Asp Asn Ile Val Ala Val Tyr
            180                 185                 190

Asp Leu Gly Gly Gly Thr Phe Asp Ile Ser Ile Ile Glu Ile Asp Ser
        195                 200                 205
```

Asn Asp Gly Asp Gln Thr Phe Glu Val Leu Ala Thr Asn Gly Asp Thr
210                 215                 220

His Leu Gly Gly Glu Asp Phe Asp Asn Arg Met Ile Asn Tyr Leu Ala
225                 230                 235                 240

Asp Glu Phe Lys Lys Asp Gln Gly Leu Asp Leu Arg Arg Asp Pro Leu
                245                 250                 255

Ala Met Gln Arg Leu Lys Glu Ala Ala Glu Lys Ala Lys Ile Glu Leu
                260                 265                 270

Ser Ser Thr Asn His Thr Glu Val Asn Leu Pro Tyr Ile Thr Ala Asp
            275                 280                 285

Ala Ser Gly Pro Lys His Leu Val Val Lys Ile Thr Arg Ala Lys Leu
290                 295                 300

Glu Ser Leu Val Glu Asp Leu Ile Gln Arg Thr Leu Glu Pro Leu Lys
305                 310                 315                 320

Val Ala Leu Ala Asp Ala Asp Leu Ser Ile Ser Asp Ile Asn Glu Val
                325                 330                 335

Ile Leu Val Gly Gly Gln Thr Arg Met Pro Lys Val Gln Glu Ala Val
            340                 345                 350

Thr Asn Phe Phe Gly Lys Glu Pro Arg Lys Asp Val Asn Pro Asp Glu
            355                 360                 365

Ala Val Ala Val Gly Ala Ala Ile Gln Ala Gly Val Leu Ser Gly Glu
370                 375                 380

Val Lys Asp Val Leu Leu Leu Asp Val Thr Pro Leu Ser Leu Gly Ile
385                 390                 395                 400

Glu Thr Met Gly Ser Val Met Thr Lys Leu Ile Glu Lys Asn Thr Thr
                405                 410                 415

Ile Pro Thr Lys Ala Gln Gln Val Phe Ser Thr Ala Asp Asp Asn Gln
                420                 425                 430

Ser Ala Val Thr Ile His Val Leu Gln Gly Glu Arg Lys Gln Ala Ser
            435                 440                 445

Ala Asn Lys Ser Leu Gly Gln Phe Asn Leu Glu Gly Ile Glu Pro Ala
            450                 455                 460

Pro Arg Gly Gln Pro Gln Val Glu Val Met Phe Asp Ile Asp Ala Asp
465                 470                 475                 480

Gly Ile Leu His Val Ser Ala Thr Asp Lys Lys Thr Gly Lys Lys Gln
                485                 490                 495

Asn Ile Thr Ile Lys Ala Ser Ser Gly Leu Ser Asp Glu Glu Val Glu
            500                 505                 510

Gln Met Val Arg Asp Ala Glu Ala His Ala Asp Glu Asp Ala Lys Phe
            515                 520                 525

Glu Glu Leu Val Lys Ala Arg Asn Gln Ala Asp Gly Leu Ala His Ser
530                 535                 540

Thr Lys Lys Gln Val Glu Ala Gly Asp Ala Leu Ala Ser Asp Glu
545                 550                 555                 560

Lys Glu Lys Ile Glu Ala Ala Ile Ala Thr Leu Glu Thr Ala Ile Lys
                565                 570                 575

Gly Lys Asp Lys Glu Ala Ile Asp Thr Ala Thr Gln Ala Leu Ile Glu
                580                 585                 590

Ala Ser Ala Lys Leu Met Glu Ile Ala Gln Ala Lys Ala Gln Gly Glu
            595                 600                 605

Ala Glu Gly Gln Ala His Asp Ala Gly Gln Glu Lys Pro Ala Asp Asp
610                 615                 620

Val Val Asp Ala Glu Phe Glu Glu Val Lys Asp Asp Lys Lys

```
<210> SEQ ID NO 27
<211> LENGTH: 1175
<212> TYPE: DNA
<213> ORGANISM: Artificial Sequence
<220> FEATURE:
<223> OTHER INFORMATION: ftsZ hybrid
<220> FEATURE:
<221> NAME/KEY: CDS
<222> LOCATION: (1)..(1155)

<400> SEQUENCE: 27
```

| | | | | | | | | | | | | | | | | |
|---|---|---|---|---|---|---|---|---|---|---|---|---|---|---|---|---|
| atg | ttt | gat | ttt | aac | gat | tca | atg | gtt | tca | aat | gcc | ata | att | aaa | gtt | 48 |
| Met | Phe | Asp | Phe | Asn | Asp | Ser | Met | Val | Ser | Asn | Ala | Ile | Ile | Lys | Val | |
| 1 | | | | 5 | | | | | 10 | | | | | 15 | | |
| gtc | ggt | gtt | ggt | ggc | ggt | ggc | ggt | aat | gct | gta | caa | cat | atg | tgt | gaa | 96 |
| Val | Gly | Val | Gly | Gly | Gly | Gly | Gly | Asn | Ala | Val | Gln | His | Met | Cys | Glu | |
| | | | 20 | | | | | 25 | | | | | 30 | | | |
| gaa | gtt | tct | gat | gtt | gag | ttt | ttt | gcc | cta | aat | aca | gat | ggt | caa | gca | 144 |
| Glu | Val | Ser | Asp | Val | Glu | Phe | Phe | Ala | Leu | Asn | Thr | Asp | Gly | Gln | Ala | |
| | | 35 | | | | | 40 | | | | | 45 | | | | |
| tta | tca | aaa | tca | aaa | gtt | caa | aat | ata | tta | caa | att | ggt | aca | aac | cta | 192 |
| Leu | Ser | Lys | Ser | Lys | Val | Gln | Asn | Ile | Leu | Gln | Ile | Gly | Thr | Asn | Leu | |
| | 50 | | | | | 55 | | | | | 60 | | | | | |
| aca | aaa | ggt | tta | ggt | gct | ggt | gcg | aat | cct | gaa | att | ggt | aag | aga | gct | 240 |
| Thr | Lys | Gly | Leu | Gly | Ala | Gly | Ala | Asn | Pro | Glu | Ile | Gly | Lys | Arg | Ala | |
| 65 | | | | | 70 | | | | | 75 | | | | | 80 | |
| gca | act | gaa | gat | aga | gcg | aaa | atc | gag | caa | ctt | tta | gag | ggt | gct | gat | 288 |
| Ala | Thr | Glu | Asp | Arg | Ala | Lys | Ile | Glu | Gln | Leu | Leu | Glu | Gly | Ala | Asp | |
| | | | | 85 | | | | | 90 | | | | | 95 | | |
| atg | gtt | ttc | atc | act | gct | ggt | atg | ggt | ggt | gga | aca | ggt | aca | ggt | gga | 336 |
| Met | Val | Phe | Ile | Thr | Ala | Gly | Met | Gly | Gly | Gly | Thr | Gly | Thr | Gly | Gly | |
| | | | 100 | | | | | 105 | | | | | 110 | | | |
| gct | cct | gta | gtt | gca | gaa | gtt | gca | aaa | gag | atg | ggt | ata | ctt | aca | gta | 384 |
| Ala | Pro | Val | Val | Ala | Glu | Val | Ala | Lys | Glu | Met | Gly | Ile | Leu | Thr | Val | |
| | | 115 | | | | | 120 | | | | | 125 | | | | |
| gct | gta | gtt | act | aag | cct | ttc | cct | ttt | gaa | gga | cca | aga | aga | atg | aaa | 432 |
| Ala | Val | Val | Thr | Lys | Pro | Phe | Pro | Phe | Glu | Gly | Pro | Arg | Arg | Met | Lys | |
| | 130 | | | | | 135 | | | | | 140 | | | | | |
| gca | gca | gag | caa | ggt | att | gag | ttt | tta | tct | aaa | agt | gtt | gat | tca | ctg | 480 |
| Ala | Ala | Glu | Gln | Gly | Ile | Glu | Phe | Leu | Ser | Lys | Ser | Val | Asp | Ser | Leu | |
| 145 | | | | | 150 | | | | | 155 | | | | | 160 | |
| att | act | att | cct | aac | gaa | aag | tta | ctg | aaa | gta | ctt | ggc | cct | gga | aca | 528 |
| Ile | Thr | Ile | Pro | Asn | Glu | Lys | Leu | Leu | Lys | Val | Leu | Gly | Pro | Gly | Thr | |
| | | | | 165 | | | | | 170 | | | | | 175 | | |
| agc | tta | tta | gat | gcc | ttt | aaa | gca | gca | aat | aac | gtg | cta | ctt | ggc | gcc | 576 |
| Ser | Leu | Leu | Asp | Ala | Phe | Lys | Ala | Ala | Asn | Asn | Val | Leu | Leu | Gly | Ala | |
| | | | 180 | | | | | 185 | | | | | 190 | | | |
| gtt | cag | ggt | att | gca | gaa | tta | att | act | cgt | cct | ggt | ttg | ata | aat | gtc | 624 |
| Val | Gln | Gly | Ile | Ala | Glu | Leu | Ile | Thr | Arg | Pro | Gly | Leu | Ile | Asn | Val | |
| | | 195 | | | | | 200 | | | | | 205 | | | | |
| gat | ttt | gct | gat | gta | cgt | acc | gtt | atg | tct | gag | atg | ggt | act | gcc | atg | 672 |
| Asp | Phe | Ala | Asp | Val | Arg | Thr | Val | Met | Ser | Glu | Met | Gly | Thr | Ala | Met | |
| | 210 | | | | | 215 | | | | | 220 | | | | | |
| atg | ggt | tct | ggt | act | gct | tct | ggc | gat | gat | aga | gca | caa | gaa | gct | gct | 720 |
| Met | Gly | Ser | Gly | Thr | Ala | Ser | Gly | Asp | Asp | Arg | Ala | Gln | Glu | Ala | Ala | |
| 225 | | | | | 230 | | | | | 235 | | | | | 240 | |
| gat | gct | gct | att | tca | agt | cct | tta | tta | gag | gat | gtg | gat | tta | gct | ggt | 768 |
| Asp | Ala | Ala | Ile | Ser | Ser | Pro | Leu | Leu | Glu | Asp | Val | Asp | Leu | Ala | Gly | |
| | | | | 245 | | | | | 250 | | | | | 255 | | |

```
gca cgc ggg atc tta gtt aat att acc gca ggt atg gat att agt atc    816
Ala Arg Gly Ile Leu Val Asn Ile Thr Ala Gly Met Asp Ile Ser Ile
            260                 265                 270 gat gag ttt gaa act gtt ggt aat gcc gtt aaa gct ttc gct tct gaa    864
Asp Glu Phe Glu Thr Val Gly Asn Ala Val Lys Ala Phe Ala Ser Glu
        275                 280                 285 aat gcg act gtt gtt gtt ggt gct gtt att gat atg gat atg aca gat    912
Asn Ala Thr Val Val Val Gly Ala Val Ile Asp Met Asp Met Thr Asp
    290                 295                 300 gag ctt cgt gtg act gtt gtt gct acg ggt att ggc gct gaa agt aag    960
Glu Leu Arg Val Thr Val Val Ala Thr Gly Ile Gly Ala Glu Ser Lys
305                 310                 315                 320 cct gat att acg tta gta aat cct atg cca atg gct gaa gca aaa gtt   1008
Pro Asp Ile Thr Leu Val Asn Pro Met Pro Met Ala Glu Ala Lys Val
            325                 330                 335 gtc ggt ggg gat tat aca cca gct gca cca cag gca aat tta gcg act   1056
Val Gly Gly Asp Tyr Thr Pro Ala Ala Pro Gln Ala Asn Leu Ala Thr
        340                 345                 350 gaa gca ata gct atg act gat agc aat gcg cag aaa gca gca gca acc   1104
Glu Ala Ile Ala Met Thr Asp Ser Asn Ala Gln Lys Ala Ala Ala Thr
    355                 360                 365 gac tta gat act tat tta gat att cct gct ttt tta cgt aag caa gcg   1152
Asp Leu Asp Thr Tyr Leu Asp Ile Pro Ala Phe Leu Arg Lys Gln Ala
370                 375                 380 gat taataaaaac caaattaag                                           1175
Asp
385

<210> SEQ ID NO 28
<211> LENGTH: 385
<212> TYPE: PRT
<213> ORGANISM: Artificial Sequence
<220> FEATURE:
<223> OTHER INFORMATION: Synthetic Construct

<400> SEQUENCE: 28

Met Phe Asp Phe Asn Asp Ser Met Val Ser Asn Ala Ile Ile Lys Val
1               5                   10                  15

Val Gly Val Gly Gly Gly Gly Asn Ala Val Gln His Met Cys Glu
            20                  25                  30

Glu Val Ser Asp Val Glu Phe Phe Ala Leu Asn Thr Asp Gly Gln Ala
        35                  40                  45

Leu Ser Lys Ser Lys Val Gln Asn Ile Leu Gln Ile Gly Thr Asn Leu
    50                  55                  60

Thr Lys Gly Leu Gly Ala Gly Ala Asn Pro Glu Ile Gly Lys Arg Ala
65                  70                  75                  80

Ala Thr Glu Asp Arg Ala Lys Ile Glu Gln Leu Leu Glu Gly Ala Asp
                85                  90                  95

Met Val Phe Ile Thr Ala Gly Met Gly Gly Gly Thr Gly Thr Gly Gly
            100                 105                 110

Ala Pro Val Val Ala Glu Val Ala Lys Glu Met Gly Ile Leu Thr Val
        115                 120                 125

Ala Val Val Thr Lys Pro Phe Pro Phe Glu Gly Pro Arg Arg Met Lys
    130                 135                 140

Ala Ala Glu Gln Gly Ile Glu Phe Leu Ser Lys Ser Val Asp Ser Leu
145                 150                 155                 160

Ile Thr Ile Pro Asn Glu Lys Leu Leu Lys Val Leu Gly Pro Gly Thr
                165                 170                 175
```

```
Ser Leu Leu Asp Ala Phe Lys Ala Ala Asn Asn Val Leu Leu Gly Ala
            180             185                 190

Val Gln Gly Ile Ala Glu Leu Ile Thr Arg Pro Gly Leu Ile Asn Val
        195             200                 205

Asp Phe Ala Asp Val Arg Thr Val Met Ser Glu Met Gly Thr Ala Met
    210             215             220

Met Gly Ser Gly Thr Ala Ser Gly Asp Asp Arg Ala Gln Glu Ala Ala
225             230             235                 240

Asp Ala Ala Ile Ser Ser Pro Leu Leu Glu Asp Val Asp Leu Ala Gly
                245             250             255

Ala Arg Gly Ile Leu Val Asn Ile Thr Ala Gly Met Asp Ile Ser Ile
            260             265             270

Asp Glu Phe Glu Thr Val Gly Asn Ala Val Lys Ala Phe Ala Ser Glu
        275             280             285

Asn Ala Thr Val Val Val Gly Ala Val Ile Asp Met Asp Met Thr Asp
    290             295             300

Glu Leu Arg Val Thr Val Val Ala Thr Gly Ile Gly Ala Glu Ser Lys
305             310             315                 320

Pro Asp Ile Thr Leu Val Asn Pro Met Pro Met Ala Glu Ala Lys Val
            325             330             335

Val Gly Gly Asp Tyr Thr Pro Ala Ala Pro Gln Ala Asn Leu Ala Thr
            340             345             350

Glu Ala Ile Ala Met Thr Asp Ser Asn Ala Gln Lys Ala Ala Ala Thr
            355             360             365

Asp Leu Asp Thr Tyr Leu Asp Ile Pro Ala Phe Leu Arg Lys Gln Ala
    370             375             380

Asp
385
```